United States Patent
Maguire

(10) Patent No.: US 7,671,043 B2
(45) Date of Patent: Mar. 2, 2010

(54) CYCLOALKYLAMINO ACID DERIVATIVES

(75) Inventor: Robert John Maguire, East Lyme, CT (US)

(73) Assignee: Pfizer Inc, New York, NY (US)

( * ) Notice: Subject to any disclaimer, the term of this patent is extended or adjusted under 35 U.S.C. 154(b) by 107 days.

(21) Appl. No.: 11/746,314

(22) Filed: May 9, 2007

(65) Prior Publication Data

US 2007/0270438 A1 Nov. 22, 2007

Related U.S. Application Data

(60) Provisional application No. 60/799,211, filed on May 9, 2006.

(51) Int. Cl.
*A61K 31/42* (2006.01)
*A61K 31/192* (2006.01)
*A61K 31/195* (2006.01)
*A61K 31/137* (2006.01)

(52) U.S. Cl. ............... 514/137; 514/568; 514/646; 562/400; 564/305

(58) Field of Classification Search ............... 514/364, 514/255.05, 340; 544/367; 546/269.4
See application file for complete search history.

(56) References Cited

U.S. PATENT DOCUMENTS

| 5,399,578 | A | 3/1995 | Buhlmayer |
| 5,965,592 | A | 10/1999 | Buhlmayer |
| 2004/0122066 | A1 | 6/2004 | Yoshioka et al. |
| 2004/0235794 | A1 | 11/2004 | Nakade et al. |
| 2005/0070506 | A1 | 3/2005 | Doherty et al. |
| 2005/0215531 | A1 | 9/2005 | Baumruker et al. |
| 2005/0245575 | A1 | 11/2005 | Chen et al. |

FOREIGN PATENT DOCUMENTS

| JP | 4-235149 A1 | 8/1992 |
| WO | WO2004/035538 | 4/2004 |
| WO | WO2004/052880 | 6/2004 |
| WO | WO2004/091610 | 10/2004 |
| WO | WO2005/011609 | 2/2005 |
| WO | WO2005/058848 | 6/2005 |
| WO | WO2005/097800 | 10/2005 |

OTHER PUBLICATIONS

Cited ref-STN-search-11746314.*
Cited ref_S1P receptor_EDG1_Wikipedia.*
U.S. Appl. No. 12/266,997, not published, but filed by the same assigee.*
Kuang, R., et al., "Preparation of Substituted 2-quinolyl-oxazoles And Their Heterocyclic Analogs Useful As pde4 Inhibitors," XP002448639, retrieved from STN Database accession No. 2005:1289687, RN: 871014-25-4P abstract.
Lee, M., et al., "Vascular Endothelial Cell Adherens Junction Assembly And Morphogenesis Induced By Sphingosine-1-Phosphaate," Cell, 1999, 301-312, vol. 99.
Li, Z., "Discovery Of Potent 3,6-Diphenyl-1,2,4-Oxadiazole Sphingosine-1-Phospate-1 (S1P$_1$) Receptor Agonists With Exceptional Selectivity Against S1P$_2$ and S1P$_3$," Journal of Medicinal Chemistry, 2005, 6169-6173, vol. 48, No. 20.
Paik, J., et al., "Sphingozine 1-Phosphate-induced Endothelial Cell Migration Requires The Expression Of EDG-1 And EDG-3 Recepotrs And Rho-dependent Activation Of $\alpha_v\beta_3$ and $\beta_1$-contianing Integrins," The Journal of Biological Chemistry., 2001, 11830-11837, vol. 276, No. 15.
Yan, L., et al., "2-Aryl(pyrrolidin-4-yl)acetic Acids Are Potent Agonists Of Sphingozine-1-Phosphate (SIP) Receptors," Bioorganic & Medicinal Chemistry Letters, 2006, 3564-3568, vol. 16, No. 13.

* cited by examiner

*Primary Examiner*—Kamal A Saeed
*Assistant Examiner*—Yong Chu
(74) *Attorney, Agent, or Firm*—Keith D. Hutchinson; Jeffrey H. Tidwell

(57) ABSTRACT

The invention relates to compounds of formula I

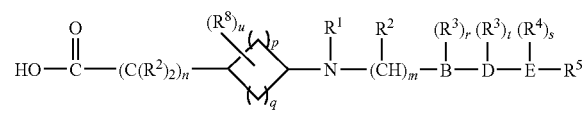

and to pharmaceutically acceptable salts, prodrugs, solvates or hydrates thereof; wherein B, D, E, R$^1$, R$^2$, R$^3$, R$^4$, R$^5$, R$^8$, m, n, p, q, r, s, t and u are as defined herein. This invention also relates to a method of using such compounds in the treatment of hyperproliferative diseases and autoimmune diseases in mammals, especially humans, and to pharmaceutical compositions containing such compounds.

5 Claims, No Drawings

CYCLOALKYLAMINO ACID DERIVATIVES

CROSS-REFERENCE TO RELATED APPLICATIONS

This application claims the benefit of U.S. Provisional Application Ser. No. 60/799,211, filed May 9, 2006, which is incorporated herein by reference in its entirety.

BACKGROUND OF THE INVENTION

This invention relates to novel carboxycycloalkylamino derivatives. The carboxycycloalkylamino derivatives of the present invention are modulators of the sphingosine-1-phosphate (S1P) receptors and have a number of therapeutic applications, particularly in the treatment of hyperproliferative and autoimmune diseases, in mammals, especially humans, and to pharmaceutical compositions containing such compounds.

The S1P receptors 1-5 constitute a family of seven-transmembrane G-protein coupled receptors. These receptors, referred to as S1P1 to S1P5, are activated via binding by sphingosine-1-phosphate, which is produced by the sphingosine kinase phosphorylation of sphingosine. S1P receptors are cell surface receptors involved in a variety of cellular processes, including cell proliferation and differentiation, cell survival, and cell migration. S1P is found in plasma and a variety of other tissues and exerts autocrine and paracrine effects.

Recent studies indicate that S1P binds to the S1P1 receptor to promote tumor angiogenesis by supporting the migration, proliferation and survival of endothelial cells (ECs) as they form new vessels within tumors (tumor angiogenesis) (Lee et al., *Cell.* 99:301-312 (1999) Paik et al., *J. Biol. Chem.* 276: 11830-11837 (2001)). Because S1P is required for optimal activity of multiple proangiogenic factors, modulating S1P1 activation may affect angiogenesis, proliferation, and interfere with tumor neovascularization, vessel maintenance and vascular permeability.

Other diseases or conditions that may be treated with the compounds of the present invention include organ transplant rejection and inflammatory diseases, which are believed to proceed via modulating the S1P receptors.

Thus, the identification of compounds which modulate the activity of the S1P1 receptor to regulate and modulate abnormal or inappropriate cell proliferation, differentiation, or metabolism is therefore desirable.

SUMMARY OF THE INVENTION

The present invention related to a compound of the formula I

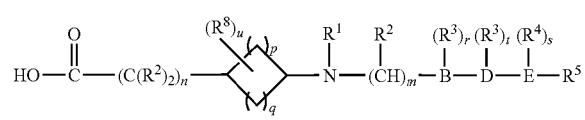

or the pharmaceutically acceptable salts thereof;

wherein B is selected from the group consisting of phenyl and a (5 to 6-membered)-heteroaryl ring;

D is selected from the group consisting of phenyl and a (5 to 6-membered)-heteroaryl ring;

E is selected from the group consisting of phenyl and a (5 to 6-membered)-heteroaryl ring;

$R^1$ is a radical selected from the group consisting of hydrogen, $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7-SO_2-$, $R^7-C(O)-$, $R^7O-C(O)-$, and $(R^7)_2N-C(O)-$;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7-SO_2-$, $R^7-C(O)-$, $R^7O-C(O)-$, and $(R^7)_2N-C(O)-R^1$ radicals may optionally be substituted by one to three moieties independently selected from the group consisting of hydrogen, hydroxy, halogen, $-CN$, $(C_1-C_6)$alkyl-, $(C_1-C_6)$alkoxy-, perhalo$(C_1-C_6)$alkyl-, $(C_3-C_7)$cycloalkyl-, $(C_2-C_9)$heterocyclyl-, $(C_6-C_{10})$aryl-, and $(C_1-C_{12})$heteroaryl-;

each $R^2$ is a radical independently selected from the group consisting of hydrogen, hydroxy, halogen, $-CN$, $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, and $(C_1-C_{12})$heteroaryl-;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, and $(C_1-C_{12})$heteroaryl-$R^2$ radicals may optionally be substituted by one to three moieties independently selected from the group consisting of hydrogen, hydroxy, halogen, $-CN$, $(C_1-C_6)$alkyl-, perhalo$(C_1-C_4)$alkyl-, perhalo$(C_1-C_4)$alkoxy-, $(C_3-C_7)$cycloalkyl-, $(C_2-C_8)$heterocyclyl-, $(C_6-C_{10})$aryl-, and $(C_1-C_{12})$heteroaryl-;

each $R^3$ is a radical independently selected from the group consisting of hydrogen, halogen, hydroxy, $-CN$, $(C_1-C_6)$alkyl-, $(C_2-C_6)$alkenyl-, $(C_2-C_6)$alkynyl-, $(C_3-C_7)$cycloalkyl-, $(C_1-C_6)$alkoxy-, perhalo$(C_1-C_6)$alkyl-, and perhalo$(C_1-C_6)$alkoxy-;

each $R^4$ is a radical independently selected from the group consisting of hydrogen, halogen, hydroxy, $-CN$, $-N(R^6)_2$, $(C_1-C_6)$alkyl-, $(C_2-C_6)$alkenyl-, $(C_3-C_6)$alkynyl-, $(C_1-C_6)$alkoxy-, perhalo$(C_1-C_6)$alkyl-, $(C_1-C_6)$alkyl-$S(O)_k-$, $R^{10}C(O)N(R^{10})-$, $(R^{10})_2NC(O)-$, $R^{10}C(O)-$, $R^{10}C(O)-$, $(R^{10})_2NC(O)N(R^{10})-$, $(R^{10})_2NS(O)-$, $(R^{10})_2NS(O)_2-$, $(C_3-C_7)$cycloalkyl-, $(C_6-C_{10})$aryl-, $(C_2-C_9)$heterocyclyl-, and $(C_1-C_{12})$heteroaryl-;

wherein each of said $(C_1-C_6)$alkyl-, $(C_2-C_6)$alkenyl-, $(C_3-C_6)$alkynyl-, $(C_1-C_5)$alkoxy-, $(C_1-C_6)$-alkyl-$S(O)_k-$, $R^{10}C(O)N(R^{10})-$, $(R^{10})_2NC(O)-$, $R^{10}C(O)-$, $R^{10}OC(O)-$, $(R^{10})_2NC(O)N(R^{10})-$, $(R^{10})_2NS(O)-$, $(R^{10})_2NS(O)_2-$, $(C_3-C_7)$cycloalkyl-, $(C_6-C_{10})$aryl-, $(C_2-C_9)$heterocyclyl-, and $(C_1-C_{12})$heteroaryl-$R^4$ radicals may optionally be substituted from one to five moieties independently selected from the group consisting of halogen, hydroxy, $-CN$, $(C_1-C_6)$alkyl-, $(C_3-C_7)$cycloalkyl, $-(C_1-C_6)$alkoxy and -perhalo$(C_1-C_6)$alkoxy;

$R^5$ is a radical selected from the group consisting of hydrogen, halogen, $-CN$, $(C_1-C_{10})$alkyl-, $(C_1-C_6)$alkoxy-, $(C_2-C_{10})$alkenyl-, $(C_2-C_{10})$alkynyl-, $(C_3-C_7)$cycloalkyl-, $(C_6-C_{10})$aryl-, $(C_2-C_9)$heterocyclyl-, $(C_1-C_{12})$heteroaryl-, $(C_3-C_7)$cycloalkyl-$O-$, $(C_6-C_{10})$aryl-$O-$, $(C_2-C_9)$heterocyclyl-$O-$, $(C_1-C_{12})$heteroaryl-$O-$, $R^7-S-$, $R^7-SO-$, $R^7-SO_2-$, $R^7-O(O)-$, $R^7-C(O)-O-$, $R^7O-C(O)-$, and $(R^7)_2N-C(O)-$;

wherein each of said $(C_1-C_{10})$alkyl-, $(C_1-C_6)$alkoxy- and $(C_2-C_{10})$alkynyl-$R^5$ radicals may optionally be substituted with from one to five moieties independently selected from the group consisting of halogen, hydroxy, $-CN$, $(C_1-C_6)$alkyl-, $(C_3-C_7)$cycloalkyl-, $(C_6-C_{10})$aryl-, $(C_1-C_6)$alkoxy-, $(C_2-C_9)$heterocyclyl-, and $(C_1-C_{12})$heteroaryl-;

wherein each of said $(C_3-C_7)$cycloalkyl- and $(C_3-C_7)$cycloalkyl-$O-R^5$ radicals may optionally be substituted with from one to five moieties independently selected from the group consisting of halogen, hydroxy, —CN, $(C_1-C_6)$alkyl-, $(C_6-C_{10})$aryl-, $(C_1-C_6)$alkoxy-, $(C_2-C_9)$heterocyclyl-, and $(C_1-C_{12})$heteroaryl-;

wherein each of said $(C_6-C_{10})$aryl-, $(C_2-C_9)$heterocyclyl-, $(C_1-C_{12})$heteroaryl-, $(C_6-C_{10})$aryl-O—, $(C_2-C_9)$heterocyclyl-O—, and $(C_1-C_{12})$heteroaryl-O—$R^5$ radicals may optionally be substituted with from one to five moieties independently selected from the group consisting of halogen, hydroxy, —CN, $(C_1-C_6)$alkyl-, and $(C_1-C_6)$alkoxy-;

wherein each of said $R^7$—S—, $R^7$—SO—, $R^7$—$SO_2$—, $R^7$—C(O)—, $R^7$—C(O)—O—, $R^7O$—C(O)—, and $(R^7)_2$N—C(O)—$R^5$ radicals may optionally be substituted with from one to five moieties independently selected from the group consisting of halogen, hydroxy, —CN, $(C_1-C_6)$alkyl-, $(C_3-C_7)$cycloalkyl, and $(C_1-C_6)$alkoxy-;

wherein each of aforesaid $(C_1-C_6)$alkyl-, $(C_1-C_6)$alkoxy-, $(C_6-C_{10})$aryl-, $(C_1-C_6)$alkoxy-, $(C_2-C_9)$heterocyclyl-, and $(C_1-C_{12})$heteroaryl-moieties for each of aforesaid $R^5$ radicals may optionally be substituted with one to five halogen groups;

optionally said $R^5$ radical and one $R^4$ radical or two $R^4$ radicals may be taken together with E to form an (8 to 10-membered)-fused bicyclic ring optionally containing 1 to 4 heteroatoms selected from the group consisting of O, S, or $N(R^6)$;

wherein said (8 to 10-membered)-fused bicyclic ring is additionally optionally substituted with one to two oxo (=O) groups;

each $R^6$ is a bond or a radical independently selected from the group consisting of hydrogen, $(C_1-C_6)$alkyl-, —CN, and perhalo$(C_1-C_6)$alkyl-;

each $R^7$ is a radical independently selected from the group consisting of hydrogen, —CN, $(C_1-C_6)$alkyl-, perhalo$(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, and $(C_1-C_{12})$heteroaryl-;

each $R^8$ is a radical independently selected from the group consisting of hydrogen, hydroxy, halogen, —CN, —$NH(R^9)$, $(C_1-C_6)$alkyl-, perhalo$(C_1-C_6)$alkyl- and $(C_1-C_6)$alkoxy-;

wherein each of said $(C_1-C_6)$alkyl- and $(C_1-C_6)$alkoxy-$R^8$ radicals is optionally substituted from one to five moieties selected from the group consisting of perhalo$(C_1-C_6)$alkyl-, —$O(R^9)$ and —$N(R^9)_2$;

each $R^9$ is a radical independently selected from the group consisting of hydrogen, $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7$—S—, $R^7$—SO—, $R^7$—$SO_2$—, $R^7$—C(O)—, $R^7$—C(O)—O—, $R^7O$—C(O)—, and $(R^7)_2$N—C(O)—;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-$R^9$ radicals is optionally substituted by one to three moieties independently selected from the group consisting of hydrogen, hydroxy, halogen, —CN, $(C_1-C_6)$alkyl-, $(C_1-C_6)$alkoxy-, perhalo$(C_1-C_6)$alkyl-, $(C_3-C_7)$cycloalkyl-, $(C_2-C_9)$heterocyclyl-, $(C_6-C_{10})$aryl-, and $(C_1-C_{12})$heteroaryl-;

each $R^{10}$ is a radical selected from the group consisting of hydrogen and $(C_1-C_6)$alkyl-;

k is an integer from 0 to 2;

m and n are each independently an integer from 0 to 3;

p is an integer from 1 to 2;

q is an integer from 0 to 2; and r, s, t and u are each independently an integer from 0 to 4.

As used herein, the phrase "compound of formula I" and "pharmaceutically acceptable salts" includes prodrugs, metabolites, solvates or hydrates thereof.

More specifically, the present invention includes pharmaceutically acceptable acid addition salts of compounds of the formula I. The acids which are used to prepare the pharmaceutically acceptable acid addition salts of the aforementioned base compounds of this invention are those which form non-toxic acid addition salts, i.e. salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also includes base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

All references to compounds of formula I, unless otherwise specified, include references to salts, solvates, multi-component complexes and liquid crystals thereof and to solvates, multi-component complexes and liquid crystals of salts thereof.

As indicated, so-called 'prodrugs' of the compounds of formula I are also within the scope of the invention. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula I with certain moieties known to those skilled in the art as 'pro-moieties' as described, for example, in *Design of Prodrugs* by H. Bundgaard (Elsevier, 1985).

Some examples of prodrugs in accordance with the invention include (i) where the compound of formula I contains a carboxylic acid functionality (—COOH), an ester thereof, for example, a compound wherein the hydrogen of the carboxylic acid functionality of the compound of formula I is replaced by (C$_1$-C$_8$) alkyl;

(ii) where the compound of formula I contains an alcohol functionality (—OH), an ether thereof, for example, a compound wherein the hydrogen of the alcohol functionality of the compound of formula I is replaced by (C$_1$-C$_6$)alkanoyloxymethyl; and (iii) where the compound of formula I contains a primary or secondary amino functionality (—NH$_2$ or —NHR where R≠H), an amide thereof, for example, a compound wherein, as the case may be, one or both hydrogens of the amino functionality of the compound of formula I is/are replaced by (C$_1$-C$_{10}$)alkanoyl.

Further examples of replacement groups in accordance with the foregoing examples and examples of other prodrug types may be found in the aforementioned references.

Moreover, certain compounds of formula I may themselves act as prodrugs of other compounds of formula I.

Also included within the scope of the invention are metabolites of compounds of formula I, that is, compounds formed in vivo upon administration of the drug. Some examples of metabolites in accordance with the invention include (i) where the compound of formula I contains a methyl group, an hydroxymethyl derivative thereof (—CH$_3$→—CH$_2$OH);

(ii) where the compound of formula I contains an alkoxy group, an hydroxy derivative thereof (—OR→—OH);

(iii) where the compound of formula I contains a tertiary amino group, a secondary amino derivative thereof (—NR$^1$R$^2$→—NHR$^1$ or —NHR$^2$);

(iv) where the compound of formula I contains a secondary amino group, a primary derivative thereof (—NHR$^1$→—NH$_2$);

(v) where the compound of formula I contains a phenyl moiety, a phenol derivative thereof (—Ph→—PhOH);

(vi) where the compound of formula I contains an amide group, a carboxylic acid derivative thereof (—CONH$_2$→—COOH); and (vii) where the compound of formula I contains an additional O-glucuronic acid substituent and wherein any nitrogen atom in the compound of formula I is bonded to an oxygen atom to form an N-oxide.

Compounds of formula I can exist as two or more stereoisomers. The compounds of formula I may include, but is not limited to, the following stereoisomers, wherein p and q are the same integer:

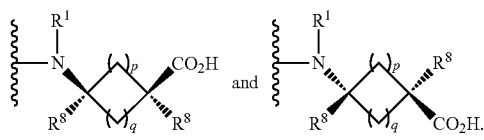

Additionally, the compounds of formula I may include, but are not limited to, the following stereoisomers, wherein p and q are different integers:

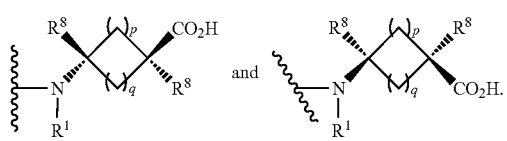

Further, one skilled in the art would appreciate that additional stereoisomeric forms of compounds of formula I may be formed by the introduction of substitution on the cycloalkyl ring.

Additionally, where a compound of formula I contains an alkenyl or alkenylene group, geometric cis/trans (or Z/E) isomers are possible.

Where structural isomers are readily interconvertible tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl) having the indicated number of carbon atoms. The phrase "each of said alkyl" as used herein refers to any of the preceding alkyl moieties within a group such alkoxy, alkenyl or alkylamino. Preferred alkyls include ($C_1$-$C_4$)alkyl, most preferably methyl.

As used herein, the term "cycloalkyl" refers to a mono- or bi-cyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.) having the indicated number of carbon atoms.

As used herein, the term "halogen" includes fluoro, chloro, bromo or iodo or fluoride, chloride, bromide or iodide.

As used herein, the term "alkenyl" means straight or branched chain unsaturated radicals having the indicated number of carbon atoms, including, but not limited to ethenyl, 1-propenyl, 2-propenyl (allyl), iso-propenyl, 2-methyl-1-propenyl, 1-butenyl, 2-butenyl, and the like.

As used herein, the term "alkynyl" is used herein to mean straight or branched hydrocarbon chain radicals having the indicated number of carbon atoms and having one triple bond including, but not limited to, ethynyl, propynyl, butynyl, and the like.

As used herein, the term "phenyl" means a phenyl radical. Also, the term "aryl" refers to a mono- or bi-cyclic aromatic group having the indicated number of carbon atoms.

As used herein, the term "heteroaryl" refers to an aromatic or partially saturated monocyclic or bicyclic ring system, having the indicated number of carbon atoms (e.g., ($C_1$-$C_{12}$) heteroaryl-), or having an indicated number of members (e.g., (5 to 6-membered)-heteroaryl ring or (8 to 10-membered)-fused bicyclic ring), and containing at least one heteroatom selected from O, S and N in the ring. A preferred group of heteroaryls is for example pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl, 1-oxa-2,4-diazolyl, 1-oxa-2,5-diazolyl, 1-oxa-3,5-diazolyl), thiadiazolyl (e.g., 1,3,4-thiadiazolyl), tetrazole, quinolyl, isoquinolyl, benzothienyl, benzofuryl, indolyl, and the like.

The term "heterocyclic" as used herein refers to a cyclic group having the indicated number of carbon atoms (e.g., ($C_2$-$C_9$)heterocyclyl-) and 1-4 hetero atoms selected from N, O, or S. Examples of such rings include mono- or bi-cyclic saturated or partially saturated ring systems such as tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, 1,2,5-oxathiazin-4-yl and the like. Examples of bicyclic saturated or partially saturated ring systems include indolinyl, 3H-indolyl, 2,3-dihydrobenzofuran, 1,2,3,4-tetrahydroquinolinyl, and 1,2,3,4-tetrahydroisoquinolinyl.

As used herein, the term "oxo" is used to mean a double bonded oxygen (=O) radical, for example, where the bond partner is a carbon atom, the radical can be thought as a carbonyl group.

An embodiment of the present invention includes those compounds of formula I, wherein B is phenyl and r is an integer from 0 to 4.

Another embodiment of the present invention includes those compounds of formula I, wherein B is a 5-membered-heteroaryl ring and r is an integer from 0 to 4.

A further embodiment of the present invention includes those compounds of formula I, wherein B is a 6-membered-heteroaryl ring and r is an integer from 0 to 4.

A further embodiment of the present invention includes those compounds of formula I, wherein D is a 5-membered-heteroaryl ring and t is an integer from 0 to 4.

A further embodiment of the present invention includes those compounds of formula I, wherein D is a 6-membered-heteroaryl ring and t is an integer from 0 to 4.

A further embodiment of the present invention includes those compounds of formula I, wherein E is phenyl and s is an integer from 0 to 4.

A further embodiment of the present invention includes those compounds of formula I, wherein E is a 5-membered-heteroaryl ring and s is an integer from 0 to 4.

A further embodiment of the present invention includes those compounds of formula I, wherein E is a 6-membered-heteroaryl ring and s is an integer from 0 to 4.

A further embodiment of the present invention includes those compounds of formula I, wherein $R^1$ is a radical selected from the group consisting of hydrogen, —CN, ($C_1$-$C_6$)alkyl-, ($C_2$-$C_6$)alkenyl-, and ($C_2$-$C_6$)alkynyl-, wherein each of said ($C_1$-$C_6$)alkyl-, ($C_2$-$C_6$)alkenyl-, and ($C_2$-$C_6$) alkynyl-$R^1$ radicals is optionally substituted by one to three moieties independently selected from the group consisting of hydrogen, hydroxy, halogen, ($C_1$-$C_6$)alkyl-, ($C_1$-$C_6$)alkoxy-, perhalo($C_1$-$C_6$)alkyl-, ($C_3$-$C_7$)cycloalkyl-, ($C_2$-$C_9$)heterocyclyl-, ($C_6$-$C_{10}$)aryl-, and ($C_1$-$C_{12}$)heteroaryl-.

Other embodiments of the compounds of formula I include those wherein $R^1$ is a radical selected from the group consisting of ($C_3$-$C_7$)cycloalkyl-, ($C_2$-$C_9$)heterocyclyl-, ($C_6$-$C_{10}$) aryl-, and ($C_1$-$C_{12}$)heteroaryl-, wherein each of said ($C_3$-$C_7$) cycloalkyl-, ($C_2$-$C_9$)heterocyclyl-, ($C_6$-$C_{10}$)aryl-, and ($C_1$-$C_{12}$)heteroaryl-$R^1$ radicals is optionally substituted by one to three moieties independently selected from the group consisting of hydrogen, hydroxy, halogen, ($C_1$-$C_6$)alkyl-, ($C_1$-$C_6$) alkoxy-, perhalo($C_1$-$C_6$)alkyl-, ($C_3$-$C_7$)cycloalkyl-, ($C_2$-$C_9$) heterocyclyl-, ($C_6$-$C_{10}$)aryl-, and ($C_1$-$C_{12}$)heteroaryl-.

Other embodiments of the compounds of formula I include those wherein $R^1$ is a radical selected from the group consisting of $R^7$—$SO_2$—, $R^7$—C(O)—, $R^7O$—C(O)—, and $(R^7)_2$ N—C(O)—, wherein each of said $R^7$—$SO_2$—, $R^7$—C (O)—, $R^7O$—C(O)—, and $(R^7)_2N$—C(O)—$R^1$ radicals is optionally substituted by one to three moieties independently selected from the group consisting of hydrogen, hydroxy, halogen, —CN, $(C_1-C_6)$alkyl-, $(C_1-C_6)$alkoxy-, perhalo$(C_1-C_6)$alkyl-, $(C_3-C_7)$cycloalkyl-, $(C_2-C_9)$heterocyclyl-, $(C_6-C_{10})$aryl-, and $(C_1-C_{12})$heteroaryl-.

Other embodiments of the compounds of formula I include those wherein $R^5$ is a radical independently selected from the group consisting of hydrogen, halogen, and —CN.

Other embodiments of the compounds of formula I include those wherein $R^5$ is a radical independently selected from the group consisting of $(C_1-C_{10})$alkyl-, $(C_1-C_6)$alkoxy-, $(C_2-C_{10})$alkenyl-, and $(C_2-C_{10})$alkynyl-, wherein each of said $(C_1-C_{10})$alkyl-, $(C_1-C_6)$alkoxy-, $(C_2-C_{10})$alkenyl-, and $(C_2-C_{10})$alkynyl-$R^5$ radicals is optionally substituted from one to five moieties independently selected from the group consisting of halogen, hydroxy, —CN, $(C_1-C_6)$alkyl-, $(C_3-C_7)$cycloalkyl-, $(C_6-C_{10})$aryl-, $(C_1-C_6)$alkoxy-, $(C_2-C_9)$heterocyclyl-, and $(C_1-C_{12})$heteroaryl-.

Other embodiments of the compounds of formula I include those wherein $R^5$ is selected from the group consisting of $(C_3-C_7)$cycloalkyl- and $(C_3-C_7)$cycloalkyl-O—, wherein each of said $(C_3-C_7)$cycloalkyl- and $(C_3-C_7)$cycloalkyl-O—$R^5$ radicals is optionally substituted from one to five moieties independently selected from the group consisting of halogen, hydroxy, —CN, $(C_1-C_6)$alkyl-, $(C_6-C_{10})$aryl-, $(C_1-C_6)$alkoxy-, $(C_2-C_9)$heterocyclyl-, and $(C_1-C_{12})$heteroaryl-.

Other embodiments of the compounds of formula I include those wherein $R^5$ is selected from the group consisting of $(C_6-C_{10})$aryl-, $(C_2-C_9)$heterocyclyl-, $(C_1-C_{12})$heteroaryl-, $(C_6-C_{10})$aryl-O—, $(C_2-C_9)$heterocyclyl-O—, and $(C_1-C_{12})$heteroaryl-O—, wherein each of said $(C_6-C_{10})$aryl-, $(C_2-C_9)$heterocyclyl-, $(C_1-C_{12})$heteroaryl-, $(C_6-C_{10})$aryl-O—, $(C_2-C_9)$heterocyclyl-O—, and $(C_1-C_{12})$heteroaryl-O—$R^5$ radicals is optionally substituted from one to five moieties independently selected from the group consisting of halogen, hydroxy, —CN, $(C_1-C_6)$alkyl-, and $(C_1-C_6)$alkoxy-.

Other embodiments of the compounds of formula I include those wherein $R^5$ is selected from the group consisting of $R^7$—S—, $R^7$—SO—, $R^7$—$SO_2$—, $R^7$—C(O)—, $R^7$—C(O)—O—, $R^7O$—C(O)—, and $(R^7)_2N$—C(O)—, wherein each of said $R^7$—S—, $R^7$—SO—, $R^7$—$SO_2$—, $R^7$—C(O)—, $R^7$—C(O)—O—, $R^7O$—C(O)—, and $(R^7)_2N$—C(O)—$R^5$ radicals is optionally substituted from one to five moieties independently selected from the group consisting of halogen, hydroxy, —CN, $(C_1-C_6)$alkyl-, $(C_3-C_7)$cycloalkyl, $(C_1-C_6)$alkoxy- and perhalo$(C_1-C_6)$alkoxy-.

Other embodiments of the compounds of formula I include those wherein each of aforesaid $(C_1-C_6)$alkyl-, $(C_1-C_6)$alkoxy-, $(C_6-C_{10})$aryl-, $(C_1-C_6)$alkoxy-, $(C_2-C_9)$heterocyclyl-, and $(C_1-C_{12})$heteroaryl-moieties for each of aforesaid $R^5$ radicals may optionally be substituted with one to five halogen groups.

Other embodiments of the compounds of formula I include those wherein said $R^5$ and one $R^4$ radical or two $R^4$ radicals are taken together with E to form an (8 to 10-membered)-fused bicyclic ring, optionally containing 1 to 4 heteroatoms selected from the group consisting of O, S, or $N(R^6)$.

Other embodiments of the compounds of formula I include those wherein said (8 to 10-membered)-fused bicyclic ring contains at least one oxygen atom.

Other embodiments of the compounds of formula I include those wherein said (B to 10-membered)-fused bicyclic ring is additionally optionally substituted with one to two oxo (=O) groups.

Other embodiments of the compounds of formula I include those wherein each $R^2$ is a radical independently selected from the group consisting of hydrogen, hydroxy, halogen, —CN, $(C_1-C_6)$alkyl-, $(C_2-C_6)$alkenyl-, and $(C_2-C_6)$alkynyl-, wherein each of said $(C_1-C_6)$alkyl-, $(C_2-C_6)$alkenyl-, and $(C_2-C_6)$alkynyl-$R^2$ radicals is optionally substituted by one to three moieties independently selected from the group consisting of hydrogen, hydroxy, $(C_1-C_6)$alkyl-, halogen, perhalo$(C_1-C_4)$alkyl-, perhalo$(C_1-C_4)$alkoxy-, $(C_3-C_7)$cycloalkyl-, $(C_2-C_9)$heterocyclyl-, $(C_6-C_{10})$aryl-, and $(C_1-C_{12})$heteroaryl-.

Other embodiments of the compounds of formula I include those wherein each $R^2$ is a radical independently selected from the group consisting of $(C_3-C_7)$cycloalkyl-, $(C_2-C_9)$heterocyclyl-, $(C_6-C_{10})$aryl-, and $(C_1-C_{12})$heteroaryl-, wherein each of said $(C_3-C_7)$cycloalkyl-, $(C_2-C_9)$heterocyclyl-, $(C_6-C_{10})$aryl-, and $(C_1-C_{12})$heteroaryl-$R^2$ radicals is optionally substituted by one to three moieties independently selected from the group consisting of hydrogen, hydroxy, halogen, —CN, $(C_1-C_6)$alkyl-, perhalo$(C_1-C_4)$alkyl-, perhalo$(C_1-C_4)$alkoxy-, $(C_3-C_7)$cycloalkyl-, $(C_2-C_9)$heterocyclyl-, $(C_6-C_{10})$aryl-, and $(C_1-C_{12})$heteroaryl-.

Other embodiments of the compounds of formula I include those wherein each $R^4$ is a radical independently selected from the group consisting of hydrogen, halogen, hydroxy, —CN, —$N(R^6)_2$, $(C_1-C_6)$alkyl-, $(C_2-C_6)$alkenyl-, $(C_3-C_6)$alkynyl-, $(C_1-C_6)$alkoxy-, perhalo$(C_1-C_6)$alkyl-, $(C_1-C_6)$alkyl-$S(O)_k$—, $R^{10}C(O)N(R^{10})$—, $(R^{10})_2NC(O)$—, $R^{10}C(O)$—, $R^{10}OC(O)$—, $(R^{10})_2NC(O)N(R^{10})$—, $(R^{10})_2NS(O)$—, $(R^{10})_2NS(O)_2$—, wherein is each of said —$N(R^6)_2$, $(C_1-C_6)$alkyl-, $(C_2-C_6)$alkenyl-, $(C_3-C_6)$alkynyl-, $(C_1-C_6)$alkoxy-, perhalo$(C_1-C_6)$alkyl-, $(C_1-C_6)$alkyl-$S(O)_k$—, $R^{10}C(O)N(R^{10})$—, $(R^{10})_2NC(O)$—, $R^{10}C(O)$—, $R^{10}OC(O)$—, $(R^{10})_2NC(O)N(R^{10})$—, $(R^{10})_2NS(O)$—, $(R^{10})_2NS(O)_2$—$R^4$ radicals is optionally substituted from one to five moieties independently selected from the group consisting of halogen, hydroxy, —CN, $(C_1-C_6)$alkyl-, $(C_3-C_7)$cycloalkyl, $(C_1-C_6)$alkoxy- and perhalo$(C_1-C_6)$alkoxy-.

Other embodiments of the compounds of formula I include those wherein each $R^4$ is a radical independently selected from the group consisting of $(C_3-C_7)$cycloalkyl-, $(C_1-C_{10})$aryl-, $(C_2-C_9)$heterocyclyl-, and $(C_1-C_{12})$heteroaryl-, wherein each of said $(C_3-C_7)$cycloalkyl-, $(C_6-C_{10})$aryl-, $(C_2-C_9)$heterocyclyl-, and $(C_1-C_{12})$heteroaryl-$R^4$ radicals is optionally substituted from one to five moieties independently selected from the group consisting of halogen, hydroxy, —CN, $(C_1-C_6)$alkyl-, $(C_3-C_7)$cycloalkyl, $(C_1-C_6)$alkoxy- and perhalo$(C_1-C_6)$alkoxy-.

Other embodiments of the present invention include each of the aforesaid embodiments, wherein m is an integer from 0 to 2.

Other embodiments of the present invention include each of the aforesaid embodiments, wherein m is 0.

Other embodiments of the present invention include each of the aforesaid embodiments, wherein m is 1.

Other embodiments of the present invention include each of the aforesaid embodiments, wherein m is 2.

Other embodiments of the present invention include each of the aforesaid embodiments, wherein n is 0.

Other embodiments of the present invention include each of the aforesaid embodiments, wherein p is 1 and q is 1.

A more preferred embodiment of each of the aforesaid embodiments of the present invention includes compounds wherein formula I is represented by formula Ia:

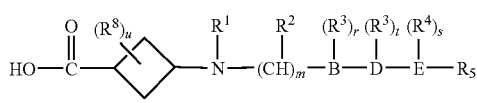

Ia

Other embodiments of the compounds of formula Ia include those wherein D is a 5-membered-heteroaryl ring and m is 1.

Other embodiments of the compounds of formula Ia include those wherein D is a 6-membered-heteroaryl ring and m is 1.

Other embodiments of the compounds of formula Ia include those wherein D contains at least one nitrogen atom.

Other embodiments of the compounds of formula Ia include those wherein D contains at least one oxygen atom.

Other embodiments of the compounds of formula Ia include those wherein D contains at least one sulfur atom.

Other embodiments of the compounds of formula Ia include those wherein D is selected from the group consisting of pyridyl, pyrazinyl, pyrimidinyl, pyridazinyl, imidazolyl, pyrrolyl, oxazolyl, thiazolyl, pyrazolyl, tetrazolyl, triazolyl, and oxadiazolyl.

Other embodiments of the compounds of formula Ia include those wherein B is phenyl.

Other embodiments of the compounds of formula Ia include those wherein B is a 6-membered-heteroaryl ring.

Other embodiments of the compounds of formula Ia include those wherein B contains at least one nitrogen atom.

Other embodiments of the compounds of formula Ia include those wherein B is selected from the group consisting of phenyl, pyridyl, pyrazinyl, pyrimidinyl, pyridazinyl, imidazolyl, pyrrolyl, oxazolyl, thiazolyl, pyrazolyl, tetrazolyl, triazolyl, and oxadiazolyl.

Other embodiments of the compounds of formula Ia include those wherein E is phenyl.

Other embodiments of the compounds of formula Ia include those wherein E is a 6-membered-heteroaryl ring.

Other embodiments of the compounds of formula Ia include those wherein E is a 5-membered-heteroaryl ring.

Other embodiments of the compounds of formula Ia include those wherein E is selected from the group consisting of phenyl, pyridyl, pyrazinyl, pyrimidinyl, pyridazinyl, imidazolyl, pyrrolyl, oxazolyl, thiazolyl, pyrazolyl, tetrazolyl, triazolyl, and oxadiazolyl.

Other embodiments of the compounds of formula Ia include those wherein $R^5$ is a radical independently selected from the group consisting of $(C_1-C_{10})$alkyl- and $(C_1-C_6)$alkoxy-, optionally substituted from one to five moieties independently selected from the group consisting of halogen, hydroxy, perhalo$(C_1-C_6)$alkyl-, $(C_3-C_7)$cycloalkyl-, $(C_6-C_{10})$aryl-, $(C_1-C_6)$alkoxy-, $(C_2-C_9)$heterocyclyl-, and $(C_1-C_{12})$heteroaryl-.

Other embodiments of the compounds of formula Ia include those wherein $R^5$ is a radical independently selected from the group consisting of $(C_1-C_{10})$alkyl- and $(C_1-C_6)$alkoxy-, wherein each of said $(C_1-C_{10})$alkyl- and $(C_1-C_6)$alkoxy-$R^5$ radicals is optionally substituted from one to five moieties independently selected from the group consisting of halogen, hydroxy, perhalo$(C_1-C_6)$alkyl-, $(C_3-C_7)$cycloalkyl-, $(C_6-C_{10})$aryl-, $(C_1-C_6)$alkoxy-, $(C_2-C_9)$heterocyclyl-, and $(C_1-C_{12})$heteroaryl-.

Other embodiments of the compounds of formula Ia include those wherein $R^5$ is selected from the group consisting of $(C_6-C_{10})$aryl-, $(C_2-C_9)$heterocyclyl-, and $(C_1-C_{12})$heteroaryl-, wherein each of said $(C_6-C_{10})$aryl-, $(C_2-C_9)$heterocyclyl-, and $(C_1-C_{12})$heteroaryl-$R^5$ radicals is optionally substituted from one to five moieties independently selected from the group consisting of halogen, hydroxy, $(C_1-C_6)$alkyl-, and $(C_1-C_6)$alkoxy-.

Other embodiments of the compounds of formula Ia include those wherein $R^5$ is selected from the group consisting of $R^7$—S—, $R^7$—SO—, $R^7$—$SO_2$—, $R^7$—C(O)—, $R^7$—C(O)—O—, $R^7$O—C(O)—, and $(R^7)_2N$—C(O)—, wherein each of said $R^7$—S—, $R^7$—SO—, $R^7$—$SO_2$—, $R^7$—C(O)—, $R^7$—C(O)—O—$R^7$O—C(O)—, and $(R^7)_2N$—C(O)—, $R^5$ radicals is optionally substituted from one to five moieties independently selected from the group consisting of halogen, hydroxy, —CN, $(C_1-C_6)$alkyl-, $(C_3-C_7)$cycloalkyl, $(C_1-C_6)$alkoxy- and perhalo$(C_1-C_6)$alkoxy-.

Other embodiments of the compounds of formula Ia include those wherein $R^5$ and one $R^4$ radical or two $R^4$ radicals are taken together to form an (8 to 10-membered)-fused bicyclic ring optionally containing 1 to 4 heteroatoms selected from the group consisting of O, S, or $N(R^6)$.

Other embodiments of the compounds of formula Ia include those wherein said (8 to 10-membered)-fused bicyclic ring is additionally optionally substituted with one to two oxo (=O) groups.

Other embodiments of the compounds of formula Ia include those wherein each $R^4$ is independently selected from the group consisting of hydrogen, halogen, hydroxy, —CN, —$N(R^6)_2$, $(C_1-C_6)$alkyl-, $(C_2-C_6)$alkenyl-, $(C_3-C_6)$alkynyl-, $(C_1-C_6)$alkoxy-, and perhalo$(C_1-C_6)$alkyl-.

Other embodiments of the compounds of formula Ia include those wherein $R^1$ is a radical selected from the group consisting of $(C_1-C_6)$alkyl-, $(C_2-C_6)$alkenyl-, and $(C_2-C_6)$alkynyl-.

Other embodiments of the compounds of formula Ia include those wherein $R^1$ is a radical selected from the group consisting of $(C_3-C_7)$cycloalkyl-, $(C_2-C_9)$heterocyclyl-, $(C_6-C_{10})$aryl-, and $(C_1-C_{12})$heteroaryl-.

Other embodiments of the compounds of formula Ia include those wherein $R^1$ is a radical selected from the group consisting of $R^7$—$SO_2$—, $R^7$—C(O)—, $R^7$O—C(O)—, and $(R^7)_2N$—C(O)—.

Other embodiments of the compounds of formula Ia include those wherein each of $R^1$ and $R^2$ are hydrogen and m is 1.

Other embodiments of the compounds of formula Ia include those wherein $R^8$ is hydrogen and u is 1.

Other embodiments of the compounds of formula Ia include those wherein $R^1$ is selected from the group consisting of hydrogen and $(C_1-C_6)$alkyl-, $R^2$ is hydrogen, D is oxadiazole, $R^8$ is hydrogen, and m is 1.

Other embodiments of the compounds of formula Ia include those wherein B is phenyl, D is a 5-membered-heteroaryl ring, E is phenyl and m is 1.

Other embodiments of the compounds of formula Ia include those wherein B is a 6-membered-heteroaryl ring, D is a 5-membered-heteroaryl ring, E is phenyl and m is 1.

Other embodiments of the compounds of formula Ia include those wherein B is phenyl, D is a 5-membered-heteroaryl ring, E is a 6-membered-heteroaryl ring, and m is 1.

Specific embodiments of the present invention includes
3-({5-[5-(4-Isobutyl-phenyl)-[1,2,4]oxadiazol-3-yl]-pyrazin-2-ylmethyl}-amino)-cis-cyclobutanecarboxylic acid;
3-({5-[3-(4-Isobutyl-phenyl)-[1,2,4]oxadiazole-5-yl]-pyridin-2-ylmethyl}-amino)-cis-cyclobutanecarboxylic acid,
3-({5-[5-(4-Isobutyl-phenyl)-[1,2,4]oxadiazol-3-yl]-pyridin-2-ylmethyl}-amino)-cis-cyclobutanecarboxylic acid;

3-({5-[5-(4-Isobutyl-phenyl)-[1,3,4]oxadiazol-2-yl]-pyridin-2-ylmethyl}-amino)-cis-cyclobutanecarboxylic acid;
cis-3-({4-[3-(4-Isobutylphenyl)-1,2,4-oxadiazol-5-yl]benzyl}amino)cyclobutanecarboxylic acid;
3-{4-[5-(4-Isobutyl-phenyl)-[1,2,4]oxadiazole-3-yl]-benzylamino}-cis-cyclobutanecarboxylic acid;
cis-3-({4-[5-(4-Isobutylphenyl)-1,3,4-oxadiazol-2-yl]benzyl}amino)cyclobutanecarboxylic acid;
3-{methyl[4-(5-(4-Isobutyl-phenyl)-[1,2,4]oxadiazole-3-yl)-benzyl]amino}-cis-cyclobutanecarboxylic acid;
3-{4-[5-(4-Propyl-phenyl)-[1,2,4]oxadiazol-3-yl]-benzylamino}-cis-cyclobutanecarboxylic acid;
3-{4-[5-(3-Ethyl-phenyl)-[1,2,4]oxadiazol-3-yl]-benzylamino}-cis-cyclobutanecarboxylic acid;
3-{4-[5-(2-Ethyl-phenyl)-[1,2,4]oxadiazol-3-yl]-benzylamino}-cis-cyclobutanecarboxylic acid;
3-{3-[5-(4-Propyl-phenyl)-[1,2,4]oxadiazol-3-yl]-benzylamino}-cis-cyclobutanecarboxylic acid;
3-{3-[5-(4-Ethyl-phenyl)-[1,2,4]oxadiazol-3-yl]-benzylamino}-cis-cyclobutanecarboxylic acid;
3-{4-[5-(4-isopropoxy-phenyl)-[1,2,4]oxadiazol-3-yl]-benzylamino}-cis-cyclobutanecarboxylic acid hydrochloride;
3-[({4-[5-(4-Isobutyl-phenyl)-[1,2,4]oxadiazol-3-yl]-3-methyl-phenyl}methyl)-amino]-cis-cyclobutanecarboxylic acid; and
3-{3-[5-(4-Isobutyl-phenyl)-[1,2,4]oxadiazole-3-yl]-benzylamino}-cis-cyclobutanecarboxylic acid, hydrochloride.

Specific embodiments of the present invention includes
3-{4-[5(4-Isobutyl-phenyl)-[1,2,4]oxadiazole-3-yl]-benzylamino}-trans-cyclobutanecarboxylic acid;
3-[4-(5-p-Tolyl-[1,2,4]oxadiazol-3-yl)-benzylamino]-cis-cyclobutanecarboxylic acid;
3-{4-[5-(4-Ethyl-phenyl)-[1,2,4]oxadiazol-3-yl]-benzylamino}-cis-cyclobutanecarboxylic acid;
3-[4-(5-o-Tolyl-[1,2,4]oxadiazol-3-yl)-benzylamino]-cis-cyclobutanecarboxylic acid;
3-{3-[5-(3-Ethyl-phenyl)-[1,2,4]oxadiazol-3-yl]-benzylamino}-cis-cyclobutanecarboxylic acid;
3-{3-[5-(4-Isobutyl-phenyl)-[1,2,4]oxadiazol-3-yl]-benzylamino}-cis-cyclobutanecarboxylic acid;
3-[3-(5-p-Tolyl-[1,2,4]oxadiazol-3-yl)-benzylamino]-cis-cyclobutanecarboxylic acid;
3-[2-(5-p-Tolyl-[1,2,4]oxadiazol-3-yl)-benzylamino]-cis-cyclobutanecarboxylic acid;
3-{2-[5-(4-Propyl-phenyl)-[1,2,4]oxadiazol-3-yl]-benzylamino}-cis-cyclobutanecarboxylic acid;
3-{4-[5-(4-Trifluoromethoxy-phenyl)-[1,2,4]oxadiazol-3-yl]-benzylamino}-cis-cyclobutanecarboxylic acid; and
3-(4-{5-[6-(2,2,2-Trifluoro-ethoxy)-pyridin-3-yl]-[1,2,4]oxadiazol-3-yl}-benzylamino)-cis-cyclobutanecarboxylic acid.

Specific embodiments of the present invention includes (phenyl)-[1,2,4]oxadiazole-3-yl]-benzylamino}-cyclobutanecarboxylic acids of the following individual compounds of formula I:
3-[4-(5-p-Tolyl-[1,2,4]oxadiazol-3-yl)-benzylamino]-cyclobutanecarboxylic acid;
3-{4-[5-(4-Ethyl-phenyl)-[1,2,4]oxadiazol-3-yl]-benzylamino}-cyclobutanecarboxylic acid;
3-{4-[5-(4-Propyl-phenyl)-[1,2,4]oxadiazol-3-yl]-benzylamino}-cyclobutanecarboxylic acid;
3-[4-(5-o-Tolyl-[1,2,4]oxadiazol-3-yl)-benzylamino]-cyclobutanecarboxylic acid;
3-{4-[5-(2-Ethyl-phenyl)-[1,2,4]oxadiazol-3-yl]-benzylamino}-cyclobutanecarboxylic acid;
3-{3-[5-(2-Ethyl-phenyl)-[1,2,4]oxadiazol-3-yl]-benzylamino}-cyclobutanecarboxylic acid;
3-[3-(5-o-Tolyl-[1,2,4]oxadiazol-3-yl)-benzylamino]-cyclobutanecarboxylic acid;
3-{3-[5-(3-Ethyl-phenyl)-[1,2,4]oxadiazol-3-yl]-benzylamino}-cyclobutanecarboxylic acid;
3-{3-[5-(4-Isobutyl-phenyl)-[1,2,4]oxadiazol-3-yl]-benzylamino}-cyclobutanecarboxylic acid;
3-{3-[5-(4-Propyl-phenyl)-[1,2,4]oxadiazol-3-yl]-benzylamino}-cyclobutanecarboxylic acid;
3-{3-[5-(4-Ethyl-phenyl)-[1,2,4]oxadiazol-3-yl]-benzylamino}-cyclobutanecarboxylic acid;
3-[3-(5-p-Tolyl-[1,2,4]oxadiazol-3-yl)-benzylamino]-cyclobutanecarboxylic acid;
3-[2-(5-p-Tolyl-[1,2,4]oxadiazol-3-yl)-benzylamino]-cyclobutanecarboxylic acid;
3-{2-[5-(4-Propyl-phenyl)-[1,2,4]oxadiazol-3-yl]-benzylamino}-cyclobutanecarboxylic acid;
3-[2-(5-m-Tolyl-[1,2,4]oxadiazol-3-yl)-benzylamino]-cyclobutanecarboxylic acid;
3-[2-(5-o-Tolyl-[1,2,4]oxadiazol-3-yl)-benzylamino]-cyclobutanecarboxylic acid;
3-{4-[5-(6-Trifluoromethyl-pyridin-3-yl)-[1,2,4]oxadiazol-3-yl]-benzylamino}-cyclobutanecarboxylic acid;
3-{4-[5-(4-Trifluoromethoxy-phenyl)-[1,2,4]oxadiazol-3-yl]-benzylamino}-cyclobutanecarboxylic acid;
3-{4-[5-(4-isopropoxy-phenyl)-[1,2,4]oxadiazol-3-yl]-benzylamino}-cyclobutanecarboxylic acid, and
cis-3-({4-[3-(4-Isobutylphenyl)-1,2,4-oxadiazol-5-yl]benzyl}amino)cyclobutane carboxylic acid.
3-{4-[5(4-Isobutyl-phenyl)-[1,2,4]oxadiazole-3-yl]-benzylamino}-cis-cyclobutanecarboxylic acid;

Specific embodiments of the present invention includes (phenyl)-[1,2,4]oxadiazole-5-yl]-pyridin-2-ylmethyl}-amino)-cyclobutanecarboxylic acids of the following individual compounds of formula I:
3-({5-[3-(4-Isobutyl-phenyl)-[1,2,4]oxadiazole-5-yl]-pyridin-2-ylmethyl}-amino)-cis-cyclobutanecarboxylic acid;
3-{5-[5-(4-Isobutyl-phenyl)-[1,2,4]oxadiazol-3-yl]-pyridin-2-ylamino}-cyclobutanecarboxylic acid; and
3-({5-[5-(4-Isobutyl-phenyl)-[1,2,4]oxadiazol-3-yl]-pyridin-2-ylmethyl}-amino)-cyclobutanecarboxylic acid.

Other specific embodiments of the present invention include pyrazinyl compounds of formula I, for example:
3-({5-[5-(4-Isobutyl-phenyl)-[1,2,4]oxadiazol-3-yl]-pyrazin-2-ylmethyl}-amino)-cyclobutanecarboxylic acid.

Other "B" species of the present invention include, for example:
3-({6-[5-(4-Isobutyl-phenyl)-[1,2,4]oxadiazol-3-yl]-5-methyl-pyridin-3-ylmethyl}-amino)-cyclobutanecarboxylic acid;
3-({5-[5-(4-Isobutyl-phenyl)-[1,2,4]oxadiazol-3-yl]-4-methyl-pyridin-2-ylmethyl}-amino)-cyclobutanecarboxylic acid;
3-({5-[5-(4-Isobutyl-phenyl)-[1,2,4]oxadiazol-3-yl]-6-methyl-pyridin-2-ylmethyl}-amino)-cyclobutanecarboxylic acid;
3-({5-[5-(4-Isobutyl-phenyl)-[1,2,4]oxadiazol-3-yl]-6-methyl-pyrazin-2-ylmethyl}-amino)-cyclobutanecarboxylic acid;
3-({5-[5-(4-Isobutyl-phenyl)-[1,3,4]oxadiazol-2-yl]-pyridin-2-ylmethyl}-amino)-cyclobutanecarboxylic acid; and
3-({2-[5-(4-Isobutyl-phenyl)-[1,2,4]oxadiazol-3-yl]-pyrimidin-5-ylmethyl}-amino)-cyclobutanecarboxylic acid.

Other "E" species of the present invention include, for example:
3-{4-[5-(5-Isobutyl-thiophen-2-yl)-[1,2,4]oxadiazol-3-yl]-benzylamino}-cyclobutanecarboxylic acid; and 3-{4-[5-(5-Chloro-6-isopropoxy-pyridin-3-yl)-[1,2,4]oxadiazol-3-yl]-3-methyl-benzylamino}-cyclobutanecarboxylic acid.

Other "D" species of the present invention include, for example: 3-{4-[2-(4-Propyl-phenyl)-pyridin-4-yl]-benzylamino}-cyclobutanecarboxylic acid; and
3-[(5-{2-[4-(1,1,2,2,2-Pentafluoro-ethoxy)-phenyl]-thiazol-5-yl}-pyridin-2-ylmethyl)-amino]-cyclobutanecarboxylic acid.

A specific embodiment of the $R^1$ compounds of the present invention includes the compounds:
3-{4-[5(4-Isobutyl-phenyl)-[1,2,4]oxadiazole-3-yl]-benzyl}-methyl-amino)-cis-cyclobutanecarboxylic acid;
3-(Acetyl-{4-[5-(4-isobutyl-phenyl)-[1,2,4]oxadiazol-3-yl]-benzyl}-amino)-cyclobutanecarboxylic acid;
3-(Ethoxycarbonyl-{4-[5-(4-isobutyl-phenyl)-[1,2,4]oxadiazol-3-yl]-benzyl}-amino)-cyclobutanecarboxylic acid;
3-(3-Ethyl-1-{4-[5-(4-isobutyl-phenyl)-[1,2,4]oxadiazol-3-yl]-benzyl}-ureido)-cyclobutanecarboxylic acid;
3-({4-[3-(4-Benzyl-5-trifluoromethyl-thiophen-2-yl)-[1,2,4]oxadiazol-5-yl]-benzyl}-phenylmethanesulfonylamino)-cyclobutanecarboxylic acid;
3-({4-[5-(4-Isobutyl-phenyl)-[1,2,4]oxadiazol-3-yl]-benzyl}-methanesulfonyl-amino)-cyclobutanecarboxylic acid;
3-(Cyclobutyl-{4-[5-(4-isopropoxy-phenyl)-[1,2,4]oxadiazol-3-yl]-benzyl}-amino)-cyclobutanecarboxylic acid; and
3-(Cyclopropylmethyl-{4-[5-(6-ethyl-pyridin-3-yl)-[1,3,4]oxadiazol-2-yl]-benzyl}-amino)-cyclobutanecarboxylic acid.

A specific embodiment of the $R^2$ compounds of the present invention includes the compound:
(1-{4-[5-(4-Isobutyl-phenyl)-[1,2,4]oxadiazol-3-yl]-phenyl}-ethylamino)-cyclobutanecarboxylic acid.

A specific embodiment of the $R^3$ compounds of the present invention includes the compounds:
3-{4-[5-(4-Isopropoxy-phenyl)-[1,3,4]oxadiazol-2-yl]-3-methyl-benzylamino}-cyclobutanecarboxylic acid;
3-{4-[3-(4-Isopropoxy-phenyl)-[1,2,4]oxadiazol-5-yl]-3-methyl-benzylamino}-cyclobutanecarboxylic acid;
3-{3-Chloro-4-[5-(4-isopropoxy-phenyl)-[1,2,4]oxadiazol-3-yl]-benzylamino}-cyclobutanecarboxylic acid;
3-{3-Cyano-4-[5-(4-isobutyl-phenyl)-[1,2,4]oxadiazol-3-yl]-benzylamino}-cyclobutanecarboxylic acid; and
3-[({4-[5-(4-Isobutyl-phenyl)-[1,2,4]oxadiazol-3-yl]-3-methyl-phenyl}methyl)-amino]-cyclobutanecarboxylic acid.

A specific embodiment of the $R^4$ compounds of the present invention includes the compound:
3-{4-[5-(4-Butyryl-3-methyl-phenyl)-[1,2,4]oxadiazol-3-yl]-benzylamino}-cyclobutanecarboxylic acid.

A specific embodiment of the $R^5$ compounds of the present invention includes the compounds:
3-[4-(5-Biphenyl-4-yl-[1,2,4]oxadiazol-3-yl)-benzylamino]-cyclobutanecarboxylic acid;
3-{4-[5-(4-Isopropyl-phenyl)-[1,2,4]oxadiazol-3-yl]-benzylamino}-cyclobutanecarboxylic acid;
3-{4-[5-(4-Tert-butyl-phenyl)-[1,2,4]oxadiazol-3-yl]-benzylamino}-cyclobutanecarboxylic acid;
3-{4-[5-(4-Trifluoromethyl-phenyl)-[1,2,4]oxadiazol-3-yl]-benzylamino}-cyclobutanecarboxylic acid;
3-{4-[5-(4-Ethylsulfanyl-phenyl)-[1,2,4]oxadiazol-3-yl]-benzylamino}-cyclobutanecarboxylic acid;
3-{4-[5-(4-Benzoyl-phenyl)-[1,2,4]oxadiazol-3-yl]-benzylamino}-cyclobutanecarboxylic acid;
3-{4-[5-(3-Chloro-4-methyl-phenyl)-[1,2,4]oxadiazol-3-yl]-benzylamino}-cyclobutanecarboxylic acid;
3-(4-{5-[4-(2,2,2-Trifluoro-acetyl)-phenyl]-[1,2,4]oxadiazol-3-yl}-benzylamino)-cyclobutanecarboxylic acid;
3-(4-{5-[4-(1-Cyano-cyclopentyl)-phenyl]-[1,2,4]oxadiazol-3-yl}-benzylamino)-cyclobutanecarboxylic acid;
3-({5-[3-(4-Pyrrolidin-1-yl-phenyl)-[1,2,4]oxadiazol-5-yl]-pyrazin-2-ylmethyl}-amino)-cyclobutanecarboxylic acid;
3-(Methyl-{5-[6-(4-Trifluoromethoxy-phenyl)-pyrazin-2-yl]-pyridin-2-ylmethyl}-amino)-cyclobutanecarboxylic acid; and
3-{4-[5-(4-Cyclohexyloxy-phenyl)-[1,3,4]oxadiazol-2-yl]-benzylamino}-cyclobutanecarboxylic acid.

A specific embodiment of the compounds of the present invention wherein $R^5$ and one $R^4$ radical or two $R^4$ radicals may be taken together with E to form an (8 to 10-membered)-fused bicyclic ring includes the compounds:
3-{4-[5-(5,6,7,8-Tetrahydro-naphthalen-2-yl)-[1,2,4]oxadiazol-3-yl]-benzylamino}-cyclobutanecarboxylic acid;
3-{4-[5-(3-Oxo-indan-5-yl)-[1,2,4]oxadiazol-3-yl]-benzylamino}-cyclobutanecarboxylic acid; and
3-({6-[3-(2,2-Dimethyl-benzo[1,3]dioxol-5-yl)-[1,2,4]oxadiazol-5-yl]-pyridin-3-ylmethyl}-amino)-cyclobutanecarboxylic acid.

A specific embodiment of the $R^8$ compounds of the present invention includes the compound 3-{4-[5-(4-Isobutyl-phenyl)-[1,2,4]oxadiazol-3-yl]-benzylamino}-2,2-dimethyl-cyclobutanecarboxylic acid.

A specific embodiment of the compounds of the present invention where m is zero (0) is 3-{4-[5-(4-Isobutyl-phenyl)-[1,2,4]oxadiazol-3-yl]-phenylamino}-cyclobutanecarboxylic acid.

A specific embodiment of the compounds of the present invention where m is 2 is 3-(2-{4-[5-(4-Isobutyl-phenyl)-[1,2,4]oxadiazol-3-yl]-phenyl}-ethylamino)-cyclobutanecarboxylic acid.

Each of the aforesaid species of the invention includes the pharmaceutically acceptable salts, prodrugs, hydrates or solvates of the aforementioned compound.

This invention also relates to a method for the treatment of abnormal cell growth in a mammal, preferably a human, comprising administering to said mammal an amount of a compound of the Formula I, or a pharmaceutically acceptable salt thereof (including hydrates, solvates and polymorphs of said compound of Formula I or pharmaceutically acceptable salts thereof), that is effective in treating abnormal cell growth.

In one embodiment of this method, the abnormal cell growth is cancer, including, but not limited to, mesothelioma, hepatobilliary cancers (hepatic and billiary duct), a primary or secondary CNS tumor, a primary or secondary brain tumor (including pituitary tumors, astrocytomas, meningiomas and medulloblastomas), lung cancer (NSCLC and SCLC), bone cancer, pancreatic cancer, skin cancer, cancer of the head or neck, cutaneous or intraocular melanoma, ovarian cancer, colon cancer, rectal cancer, liver cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, gastrointestinal stromal tumor (GIST), pancreatic endocrine tumors (such as pheochromocytoma, insulinoma, vasoactive intestinal peptide tumor, islet cell tumor and glucagonoma), carcinoid tumors, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, tumors of the blood vessels (including benign and malignant tumors such as hemangiomas, hemangiosarcomas, hemangioblastomas and lobular capillary hemangiomas) or a combination of one or more of the foregoing cancers.

Another more specific embodiment of the present invention is directed to a cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In another more specific embodiment of the present invention the cancer is selected from lung cancer (NSCLC and SCLC), breast cancer, ovarian cancer, colon cancer, rectal cancer, cancer of the anal region, or a combination of one or more of the foregoing cancers.

In another embodiment of the present invention, said abnormal cell growth is a benign proliferative disease, including, but not limited to, psoriasis, benign prostatic hypertrophy, restinosis, synovial proliferation disorder, retinopathy or other neovascular disorders of the eye, pulmonary hypertension from bone marrow for use in reconstituting normal cells of any tissue.

This invention also relates to a method for the treatment of abnormal cell growth in a mammal in need of such treatment, which comprises administering to said mammal an amount of a compound of Formula I (including hydrates, solvates and polymorphs of said compound of formula I or pharmaceutically acceptable salts thereof), in combination with one or more (preferable one to three) anti-cancer agents selected from the group consisting of traditional anticancer agents (such as DNA binding agents, mitotic inhibitors, alkylating agents, anti-metabolites, intercalating antibiotics, topoisomerase inhibitors and microtubulin inhibitors), statins, radiation, angiogenesis inhibitors, signal transduction inhibitors, cell cycle inhibitors, telomerase inhibitors, biological response modifiers (such as antibodies, immunotherapy and peptide mimics), anti-hormones, anti-androgens, gene silencing agents, gene activating agents and anti-vascular agents, wherein the amounts of the compound of Formula I together with the amounts of the combination anticancer agents is effective in treating abnormal cell growth.

The invention also relates to a method for the treatment of a hyperproliferative disorder in a mammal in need of such treatment, comprising administering to said mammal an amount of a compound of Formula I (including hydrates, solvates and polymorphs of said compound of Formula I or pharmaceutically acceptable salts thereof), in combination with an anti-cancer agent selected from the group consisting of traditional anticancer agents (such as DNA binding agents, mitotic inhibitors, alkylating agents, anti-metabolites, intercalating antibiotics, topoisomerase inhibitors and microtubulin inhibitors), statins, radiation, angiogenesis inhibitors, signal transduction inhibitors, cell cycle inhibitors, telomerase inhibitors, biological response modifiers (such as antibodies, immunotherapy and peptide mimics), hormones, anti-hormones, anti-androgens, gene silencing agents, gene activating agents and anti-vascular agents, wherein the amounts of the compound of Formula I together with the amounts of the combination anticancer agents is effective in treating said hyperproliferative disorder.

This invention also relates to a pharmaceutical composition comprising an amount of a compound of the Formula I, as defined above (including hydrates, solvates and polymorphs of said compound of Formula I or pharmaceutically acceptable salts thereof), and a pharmaceutically acceptable carrier.

The invention also relates to a pharmaceutical composition which comprises an amount of a compound of Formula I, as defined above (including hydrates, solvates and polymorphs of said compound of formula I or pharmaceutically acceptable salts thereof), in combination with one or more (preferably one to three) anti-cancer agent selected from the group consisting of traditional anticancer agents (such as DNA binding agents, mitotic inhibitors, alkylating agents, anti-metabolites, intercalating antibiotics, topoisomerase inhibitors and microtubulin inhibitors), statins, radiation, angiogenesis inhibitors, signal transduction inhibitors, cell cycle inhibitors, telomerase inhibitors, biological response modifiers, hormones, anti-hormones, anti-androgens gene silencing agents, gene activating agents and anti-vascular agents and a pharmaceutically acceptable carrier, wherein the amounts of the compound of Formula I and the combination anti-cancer agents when taken as a whole is therapeutically effective for treating said abnormal cell growth.

In one embodiment of the present invention the anti-cancer agent used in conjunction with a compound of Formula I and pharmaceutical compositions described herein is an anti-angiogenesis agent.

A more specific embodiment of the present invention includes combinations of the compounds of Formula I with anti-angiogenesis agents selected from VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors.

Preferred VEGF inhibitors, include for example, Avastin (bevacizumab), an anti-VEGF monoclonal antibody of Genentech, Inc. of South San Francisco, Calif.

Additional VEGF signaling agents include CP-547,632 (Pfizer Inc., NY, USA), AG13736 (Pfizer Inc.), Vandetanib (Zactima), sorafenib (Bayer/Onyx), AEE788 (Novartis), AZD-2171, VEGF Trap (Regeneron/Aventis), vatalanib (also known as PTK-787, ZK-222584: Novartis & Schering AG as described in U.S. Pat. No. 6,258,812), Macugen (pegaptanib octasodium, NX-1838, EYE-001, Pfizer Inc./Gilead/Eyetech), IM862 (Cytran Inc. of Kirkland, Wash., USA); Neovastat (Aeterna); and Angiozyme (a synthetic ribozyme that cleaves mRNA producing VEGF1) and combinations thereof. VEGF inhibitors useful in the practice of the present invention are disclosed in U.S. Pat. Nos. 6,534,524 and 6,235,764, both of which are incorporated in their entirety for all purposed.

Particularly preferred VEGFR inhibitors include CP-547,632, AG-13736, AG-28262, Vatalanib, sorafenib, Macugen and combinations thereof.

Additional VEGFR inhibitors are described in, for example in U.S. Pat. No. 6,492,383, issued Dec. 10, 2002, U.S. Pat. No. 6,235,764 issued May 22, 2001, U.S. Pat. No. 6,177,401 issued Jan. 23, 2001, U.S. Pat. No. 6,395,734 issued May 28, 2002, U.S. Pat. No. 6,534,524 (discloses AG13736) issued Mar. 18, 2003, U.S. Pat. No. 5,834,504 issued Nov. 10, 1998, U.S. Pat. No. 6,316,429 issued Nov. 13, 2001, U.S. Pat. No. 5,883,113 issued Mar. 16, 1999, U.S. Pat. No. 5,886,020 issued Mar. 23, 1999, U.S. Pat. No. 5,792,783 issued Aug. 11, 1998, U.S. Pat. No. 6,653,308 issued Nov. 25, 2003, WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety.

PDGFr inhibitors include but not limited to those disclosed in International Patent Publication number WO 01/40217, published Jun. 7, 2001 and International Patent Publication number WO 2004/020431, published Mar. 11, 2004, the contents of which are incorporated in their entirety for all purposes.

Preferred PDGFr inhibitors include Pfizer's CP-673,451 and CP-868,596 and their pharmaceutically acceptable salts.

TIE-2 inhibitors include GlaxoSmithKline's benzimidazoles and pyridines including GW-697465A such as described in International Patent Publications WO 02/044156 published Jun. 6, 2002, WO 03/066601 published Aug. 14, 2003, WO 03/074515 published Sep. 12, 2003, WO 03/022852 published Mar. 20, 2003 and WO 01/37835 published May 31, 2001. Other TIE-2 inhibitors include Regeneron's biologicals such as those described in International Patent Publication WO 09/611,269 published Apr. 18, 1996, Amgen's AMG-386, and Abbott's pyrrolopyrimidines such as A-422885 and BSF-466895 described in International Patent Publications WO 09/955,335, WO 09/917,770, WO 00/075139, WO 00/027822, WO 00/017203 and WO 00/017202.

In another more specific embodiment of the present invention the anti-cancer agent used in conjunction with a compound of Formula I and pharmaceutical compositions described herein is where the anti-angiogenesis agent is a protein kinase C β such as enzastaurin, midostaurin, perifosine, staurosporine derivative (such as RO0318425, RO317549, RO318830 or RO318220 (Roche)), teprenone (Selbex) and UCN-01 (Kyowa Hakko)

Examples of useful COX-II inhibitors which can be used in conjunction with a compound of Formula I and pharmaceutical compositions described herein include CELEBREX™ (celecoxib), parecoxib, deracoxib, ABT-963, COX-189 (Lumiracoxib), BMS 347070, RS 57067, NS-398, Bextra (valdecoxib), Vioxx (rofecoxib), SD-8381, 4-methyl-2-(3,4-dimethylphenyl)-1-(4-sulfamoyl-phenyl)-1H-pyrrole, 2-(4-ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-II inhibitors are disclosed in U.S. patent application Ser. Nos. 10/801,446 and 10/801,429, the contents of which are incorporated in their entirety for all purposes.

In one specific embodiment of particular interest the anti-tumor agent is celecoxib as disclosed in U.S. Pat. No. 5,466,823, the contents of which are incorporated by reference in its entirety for all purposes.

In another embodiment the anti-tumor agent is deracoxib as disclosed in U.S. Pat. No. 5,521,207, the contents of which are incorporated by reference in its entirety for all purposes.

Other useful anti-angiogenic inhibitors used in conjunction with a compound of Formula I and pharmaceutical compositions described herein include aspirin, and non-steroidal anti-inflammatory drugs (NSAIDs) which nonselectively inhibit the enzymes that make prostaglandins (cyclooxygenase I and II), resulting in lower levels of prostaglandins. Such agents include, but are not limited to, Aposyn (exisulind), Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof.

Preferred nonselective cyclooxygenase inhibitors include ibuprofen (Motrin), nuprin, naproxen (Aleve), indomethacin (Indocin), nabumetone (Relafen) and combinations thereof.

MMP inhibitors include ABT-510 (Abbott), ABT 518 (Abbott), Apratastat (Amgen), AZD 8955 (AstraZeneca), Neovostat (AE-941), COL 3 (CollaGenex Pharmaceuticals), doxycycline hyclate, MPC 2130 (Myriad) and PCK 3145 (Procyon).

Other anti-angiogenic compounds include acitretin, angiostatin, aplidine, cilengtide, COL-3, combretastatin A-4, endostatin, fenretinide, halofuginone, Panzem (2-methoxyestradiol), rebimastat, removab, Revlimid, squalamine, thalidomide, ukrain, Vitaxin (alpha-v/beta-3 integrin), and zoledronic acid.

In another embodiment the anti-cancer agent is a so called signal transduction inhibitor. Such inhibitors include small molecules, antibodies, and antisense molecules. Signal transduction inhibitors include kinase inhibitors, such as tyrosine kinase inhibitors, serine/threonine kinase inhibitors. Such inhibitors may be antibodies or small molecule inhibitors. More specifically signal transduction inhibitors include farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors and inhibitors of the WNT pathway and so called multi-targeted kinase inhibitors.

In another embodiment the anti-cancer signal transduction inhibitor is a farnesyl protein transferase inhibitor. Farnesyl protein transferase inhibitors include the compounds disclosed and claimed in U.S. Pat. No. 6,194,438, issued Feb. 27, 2002; U.S. Pat. No. 6,258,824, issued Jul. 10, 2001; U.S. Pat. No. 6,586,447, issued Jul. 1, 2003; U.S. Pat. No. 6,071,935, issued Jun. 6, 2000; and U.S. Pat. No. 6,150,377, issued Nov. 21, 2000. Other farnesyl protein transferase inhibitors include AZD-3409 (AstraZeneca), BMS-214662 (Bristol-Myers Squibb), Lonafarnib (Sarasar) and RPR-115135 (Sanofi-Aventis). Each of the foregoing patent applications and provisional patent applications is herein incorporated by reference in their entirety.

In another embodiment the anti-cancer signal transduction inhibitor is a GARF inhibitor. Preferred GARF inhibitors (glycinamide ribonucleotide formyltransferse inhibitors) include Pfizer's AG-2037 (pelitrexol) and its pharmaceutically acceptable salts. GARF inhibitors useful in the practice of the present invention are disclosed in U.S. Pat. No. 5,608,082 which is incorporated in its entirety for all purposed.

In another embodiment the anti-cancer signal transduction inhibitors used in conjunction with a compound of Formula I and pharmaceutical compositions described herein include ErbB-1 (EGFr) inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), Matuzumab (Merck AG), Nimotuzumab, Panitumumab (Abgenix/Amgen), Vandetanib, hR3 (York Medical and Center for Molecular Immunology), TP-38 (IVAX), EGFR fusion protein, EGF-vaccine, anti-EGFr immunoliposomes (Hermes Biosciences Inc.) and combinations thereof.

Preferred EGFr inhibitors include Iressa (gefitinib), Erbitux, Tarceva and combinations thereof.

In another embodiment the anti-cancer signal transduction inhibitor is selected from pan erb receptor inhibitors or ErbB2 receptor inhibitors, such as CP-724,714, PF-299804, CI-1033 (canertinib, Pfizer, Inc.), Herceptin (trastuzumab, Genentech Inc.), Omnitarg (2C4, pertuzumab, Genentech Inc.), AEE-788 (Novartis), GW-572016 (lapatinib, GlaxoSmithKline), Pelitinib (HKI-272), BMS-599626, PKI-166 (Novartis), dHER2 (HER2 Vaccine, Corixa and GlaxoSmithKline), Osidem (IDM-1), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin, TAK-165, CP-724,714, ABX-EGF, HER3 and combinations thereof.

Preferred pan erb receptor inhibitors include GW572016, PF-299804, Pelitinib, and Omnitarg and combinations thereof.

Additional erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Pat. Nos. 6,465,449, and 6,284,764, and International Application No. WO 2001/98277 each of which are herein incorporated by reference in their entirety.

Various other compounds, such as styrene derivatives, have also been shown to possess tyrosine kinase inhibitory properties, and some of tyrosine kinase inhibitors have been identified as erbB2 receptor inhibitors. Other erbB2 Inhibitors are described in European patent publications EP 566,226 A1 (published Oct. 20, 1993), EP 602,851 A1 (published Jun. 22, 1994), EP 635,507 A1 (published Jan. 25, 1995), EP 635,498 A1 (published Jan. 25, 1995), and EP 520,722 A1 (published Dec. 30, 1992). These publications refer to certain bicyclic derivatives, in particular quinazoline derivatives possessing anti-cancer properties that result from their tyrosine kinase inhibitory properties. Also, World Patent Application WO 92/20642 (published Nov. 26, 1992), refers to certain bismono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

In another embodiment the anti-cancer signal transduction inhibitor is an IGF1R inhibitor. Specific IGF1R antibodies (such as CP-751871) that can be used in the present invention include those described in International Patent Application No. WO 2002/053596, which is herein incorporated by reference in its entirety.

In another embodiment the anti-cancer signal transduction inhibitor is a MEK inhibitor. MEK inhibitors include Pfizer's MEK1/2 inhibitor PD325901, Array Biopharma's MEK inhibitor ARRY-142886, and combinations thereof.

In another embodiment the anti-cancer signal transduction inhibitor is an mTOR inhibitor. mTOR inhibitors include everolimus (RAD001, Novartis), zotarolimus, temsirolimus (CCI-779, Wyeth), AP 23573 (Ariad), AP23675, Ap23841, TAFA 93, rapamycin (sirolimus) and combinations thereof.

In another embodiment the anti-cancer signal transduction inhibitor is an Aurora 2 inhibitor such as VX-680 and derivatives thereof (Vertex), R 763 and derivatives thereof (Rigel) and ZM 447-439 and AZD 1152 (AstraZeneca), or a Checkpoint kinase 1/2 inhibitors such as XL844 (Exilixis).

In another embodiment the anti-cancer signal transduction inhibitor is an Akt inhibitor (Protein Kinase B) such as API-2, perifosine and RX-0201.

Preferred multitargeted kinase inhibitors include Sutent, (SU-11248), described in U.S. Pat. No. 6,573,293 (Pfizer, Inc, NY, USA) and imatinib mesylate (Gleevec).

Additionally, other targeted anti-cancer agents include the raf inhibitors sorafenib (BAY-43-9006, Bayer/Onyx), GV-1002, ISIS-2503, LE-AON and GI-4000.

The invention also relates to the use of the compounds of the present invention together with cell cycle inhibitors such as the CDK2 inhibitors ABT-751 (Abbott), AZD-5438 (AstraZeneca), Alvocidib (flavopiridol, Aventis), BMS-387,032 (SNS 032 Bristol Myers), EM-1421 (Erimos), indisulam (Esai), seliciclib (Cyclacel), BIO 112 (One Bio), UCN-01 (Kyowa Hakko), and AT7519 (Astex Therapeutics) and Pfizer's multitargeted CDK inhibitors PD0332991 and AG24322.

The invention also relates to the use of the compounds of the present invention together with telomerase inhibitors such as transgenic B lymphocyte immunotherapy (Cosmo Bioscience), GRN 163L (Geron), GV1001 (Pharmexa), RO 254020 (and derivatives thereof), and diazaphilonic acid.

Biological response modifiers (such as antibodies, immunotherapeutics and peptide mimics), are agents that modulate defense mechanisms of living organisms or biological responses, such as survival, growth, or differentiation of tissue cells to direct them to have anti-tumor activity.

Immunologicals including interferons and numerous other immune enhancing agents that may be used in combination therapy with compounds of formula I, optionally with one or more other agent include, but are not limited to interferon alpha, interferon alpha-2a, interferon, alpha-2b, interferon beta, interferon gamma-1a, interferon gamma-1b (Actimmune), or interferon gamma-n1, PEG Intron A, and combinations thereof. Other agents include interleukin 2 agonists (such as aldesleukin, BAY-50-4798, Ceplene (histamine dihydrochloride), EMD-273063, MVA-HPV-IL2, HVA-Muc-1-IL2, interleukin 2, teceleukin and Virulizin), Ampligen, Canvaxin, CeaVac (CEA), denileukin, filgrastim, Gastrimmune (G17DT), gemtuzumab ozogamicin, Glutoxim (BAM-002), GMK vaccine (Progenics), Hsp 90 inhibitors (such as HspE7 from Stressgen, AG-858, KOS-953, MVJ-1-1 and STA-4783), imiquimod, krestin (polysaccharide K), lentinan, Melacine (Corixa), MelVax (mitumomab), molgramostim, Oncophage (HSPPC-96), OncoVAX (including OncoVAX-CL and OncoVAX-Pr), oregovomab, sargramostim, sizofuran, tasonermin, TheraCys, thymalfasin, pemtumomab (Y-muHMFG1), picibanil, Provenge (Dendreon), ubenimex, WF-10 (Immunokine), Z-100 (Ancer-20 from Zeria), Lenalidomide (REVIMID, Celegene), thalomid (Thalidomide), and combinations thereof.

Anti-cancer agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682,736. Additional, specific CTLA4 antibodies that can be used in the present invention include those described in U.S. Provisional Application 60/113,647 (filed Dec. 23, 1998), U.S. Pat. No. 6,682,736 both of which are herein incorporated by reference in their entirety.

In another embodiment of the present invention the anti-cancer agent used in conjunction with a compound of Formula I and pharmaceutical compositions described herein is a CD20 antagonist. Specific CD20 antibody antagonists that can be used in the present invention include rituximab (Rituxan), Zevalin (Ibritumomab tiuxetan), Bexxar (131-I-tositumomab), Belimumab (LymphoStat-B), HuMax-CD20 (HuMax, Genmab), R 1594 (Roche Genentech), TRU-015 (Trubion Pharmaceuticals) and Ocrelizumab (PRO 70769).

In another embodiment of the present invention the anti-cancer agent used in conjunction with a compound of Formula I and pharmaceutical compositions described herein is a CD40 antagonist. Specific CD40 antibody antagonists that can be used in the present invention include CP-870893, CE-35593 and those described in International Patent Application No. WO 2003/040170 which is herein incorporated by reference in its entirety. Other CD40 antagonists include ISF-154 (Ad-CD154, Tragen), toralizumab, CHIR 12.12 (Chiron), SGN 40 (Seattle Genetics) and ABI-793 (Novartis).

In another embodiment of the present invention the anti-cancer agent used in conjunction with a compound of Formula I and pharmaceutical compositions described herein is a hepatocyte growth factor receptor antagonist (HGFr or c-MET).

Immunosuppressant agents useful in combination with the compounds of Formula I include epratuzumab, alemtuzumab, daclizumab, lenograstim and pentostatin (Nipent or Coforin).

The invention also relates to the use of the compounds of Formula I together with hormonal, anti-hormonal, anti-androgenal therapeutic agents such as anti-estrogens including, but not limited to fulvestrant, toremifene, raloxifene, lasofoxifene, letrozole (Femara, Novartis), anti-androgens such as bicalutamide, finasteride, flutamide, mifepristone, nilutamide, Casodex® (4'-cyano-3-(4-fluorophenylsulphonyl)-2-hydroxy-2-methyl-3'-(trifluoromethyl)-propionanilide, bicalutamide) and combinations thereof.

The invention also contemplates the use of the compounds of the present invention together with hormonal therapy, including but not limited to, exemestane (Aromasin, Pfizer Inc.), Abarelix (Praecis), Trelstar, anastrozole (Arimidex, Astrazeneca), Atamestane (Biomed-777), Atrasentan (Xinlay), Bosentan, Casodex (AstraZeneca), doxercalciferol, fadrozole, formestane, gosrelin (Zoladex, AstraZeneca), Histrelin (histrelin acetate), letrozole, leuprorelin (Lupron or Leuplin, TAP/Abbott/Takeda), tamoxifen citrate (tamoxifen, Nolvadex, AstraZeneca), and combinations thereof.

The invention also contemplates the use of the compounds of the present invention together with gene silencing agents or gene activating agents such as histone deacetylase (HDAC) inhibitors such as suberolanilide hydroxamic acid (SAHA, Merck Inc./Aton Pharmaceuticals), depsipeptide (FR901228 or FK228), G2M-777, MS-275, pivaloyloxymethyl butyrate and PXD-101.

The invention also contemplates the use of the compounds of the present invention together with gene therapeutic agents such as Advexin (ING 201), TNFerade (GeneVec, a compound which express TNFalpha in response to radiotherapy), and RB94 (Baylor College of Medicine).

The invention also contemplates the use of the compounds of the present invention together with ribonucleases such as Onconase (ranpirnase).

The invention also contemplates the use of the compounds of the present invention together with antisense oligonucleotides such as bcl-2 antisense inhibitor Genasense (Oblimersen, Genta).

The invention also contemplates the use of the compounds of the present invention together with proteosomics such as PS-341 (MLN-341) and Velcade (bortezomib).

The invention also contemplates the use of the compounds of the present invention together with anti-vascular agents such as Combretastatin A4P (Oxigene).

The invention also contemplates the use of the compounds of the present invention together with traditional cytotoxic agents including DNA binding agents, mitotic inhibitors, alkylating agents, anti-metabolites, intercalating antibiotics, topoisomerase inhibitors and microtubulin inhibitors.

Topoisomerase I inhibitors useful in the combination embodiments of the present invention include 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, and combinations thereof.

Camptothecin derivatives are of particular interest in the combination embodiments of the invention and include camptothecin, 10-hydroxycamptothecin, 9-aminocamptothecin, irinotecan, SN-38, edotecarin, topotecan and combinations thereof.

A particularly preferred toposimerase I inhibitor is irinotecan HCl (Camptosar).

Topoisomerase II inhibitors useful in the combination embodiments of the present invention include aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, and Zinecard (dexrazoxane).

Particularly preferred toposimerase II inhibitors include epirubicin (Ellence), doxorubicin, daunorubicin, idarubicin and etoposide.

Alkylating agents that may be used in combination therapy with compounds of formula I, optionally with one or more other agents include, but are not limited to, nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, or satrplatin and combinations thereof.

Particularly preferred alkylating agents include Eloxatin (oxaliplatin).

Antimetabolites that may be used in combination therapy with compounds of formula I, optionally with one or more other agents include, but are not limited to dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda), cytosine arabinoside, Gemzar (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

In another embodiment the anti-cancer agent is a poly (ADP-ribose) polymerase-1 (PARP-1) inhibitor such as AG-014699, ABT-472, INO-1001, KU-0687 and GPI 18180.

Microtubulin inhibitors that may be used in combination therapy with compounds of formula I, optionally with one or more other agents include, but are not limited to ABI-007, Albendazole, Batabulin, CPH-82, EPO 906 (Novartis), discodermolide (XAA-296), Vinfunine and ZD-6126 (AstraZeneca).

Antibiotics that may be used in combination therapy with compounds of formula I, optionally with one or more other agent including, but are not limited to, intercalating antibiotics such as actinomycin D, bleomycin, mitomycin C, neocarzinostatin (Zinostatin), peplomycin, and combinations thereof.

Plant derived anti-tumor substances (also known as spindle inhibitors) that may be used in combination therapy with compounds of formula I, optionally with one or more other agent include, but are not limited to, mitotic inhibitors, for example vinblastine, vincristine, vindesine, vinorelbine (Navelbine), docetaxel (Taxotere), Ortataxel, paclitaxel (including Taxoprexin a DHA/paciltaxel conjugate) and combinations thereof.

Platinum-coordinated compounds include but are not limited to, cisplatin, carboplatin, nedaplatin, oxaliplatin (Eloxatin), Satraplatin (JM-216), and combinations thereof.

Particularly preferred cytotoxic agents include Camptosar, capecitabine (Xeloda), oxaliplatin (Eloxatin), Taxotere and combinations thereof.

Other antitumor agents include alitretinoin, I-asparaginase, AVE-8062 (Aventis), calcitriol (Vitamin D derivative), Canfosfamide (Telcyta, TLK-286), Cotara (131IchTNT 1/b), DMXAA (Antisoma), exisulind, ibandronic acid, Miltefosine, NBI-3001 (IL-4), pegaspargase, RSR13 (efaproxiral), Targretin (bexarotene), tazarotne (Vitamin A derivative), Tesmilifene (DPPE), Theratope, tretinoin, Trizaone (tirapazamine), Xcytrin (motexafin gadolinium) and Xyotax (polyglutamate paclitaxel), and combinations thereof.

In another embodiment of the present invention statins may be used in conjunction with a compound of Formula I and pharmaceutical compositions. Statins (HMG-CoA reducatase inhibitors) may be selected from the group consisting of Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovastatin and Niacin (Advicor, Kos Pharmaceuticals), derivatives and combinations thereof.

In a preferred embodiment the statin is selected from the group consisting of Atovorstatin and Lovastatin, derivatives and combinations thereof.

Other agents useful as anti-tumor agents include Caduet, Lipitor and torcetrapib.

Another embodiment of the present invention of particular interest relates to a method for the treatment of breast cancer in a human in need of such treatment, comprising administering to said human an amount of a compound of Formula I (including hydrates, solvates and polymorphs of said compound of Formula I or pharmaceutically acceptable salts thereof), in combination with one or more (preferably one to three) anti-cancer agents selected from the group consisting of trastuzumab (Herceptin), docetaxel (Taxotere), paclitaxel, capecitabine (Xeloda), gemcitabine (Gemzar), vinorelbine (Navelbine), exemestane (Aromasin), letrozole (Femara) and anastrozole (Arimidex).

Another embodiment of the present invention of particular interest relates to a method for the treatment of colorectal cancer in a human in need of such treatment, comprising administering to said human an amount of a compound of Formula I (including hydrates, solvates and polymorphs of said compound of Formula I or pharmaceutically acceptable salts thereof), in combination with one or more (preferably one to three) anti-cancer agents selected from the group consisting of capecitabine (Xeloda), irinotecan HCl (Camptosar), bevacizumab (Avastin), cetuximab (Erbitux), oxaliplatin (Eloxatin), premetrexed disodium (Alimta), vatalanib (PTK-787), Sutent, AG-13736, SU-14843, PD-325901, Tarceva, Iressa, Pelitinib, Lapatinib, Mapatumumab, Gleevec, BMS 184476, CCI 779, ISIS 2503, ONYX 015 and Flavopyridol, wherein the amounts of the compound of Formula I together with the amounts of the combination anticancer agents is effective in treating colorectal cancer.

Another embodiment of the present invention of particular interest relates to a method for the treatment of renal cell carcinoma in a human in need of such treatment, comprising administering to said human an amount of a compound of Formula I (including hydrates, solvates and polymorphs of said compound of Formula I or pharmaceutically acceptable salts thereof), in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the compound of Formula I together with the amounts of the combination anticancer agents is effective in treating renal cell carcinoma.

Another embodiment of the present invention of particular interest relates to a method for the treatment of melanoma in a human in need of such treatment, comprising administering to said human an amount of a compound of Formula I (including hydrates, solvates and polymorphs of said compound of Formula I or pharmaceutically acceptable salts thereof), in combination with one or more (preferably one to three) anti-cancer agents selected from the group consisting of interferon alpha, interleukin-2, temozolomide, docetaxel (Taxotere), paclitaxel, DTIC, PD-325901, Axitinib, bevacizumab (Avastin), thalidomide, sorafanib, vatalanib (PTK-787), Sutent, CpG-7909, AG-13736, Iressa, Lapatinib and Gleevec, wherein the amounts of the compound of Formula I together with the amounts of the combination anticancer agents is effective in treating melanoma.

Another embodiment of the present invention of particular interest relates to a method for the treatment of Lung cancer in a human in need of such treatment, comprising administering to said human an amount of a compound of Formula I (including hydrates, solvates and polymorphs of said compound of Formula I or pharmaceutically acceptable salts thereof), in combination with one or more (preferably one to three) anticancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, and Paraplatin (carboplatin), wherein the amounts of the compound of Formula I together with the amounts of the combination anticancer agents is effective in treating Lung cancer.

In one preferred embodiment radiation can be used in conjunction with a compound of Formula I and pharmaceutical compositions described herein. Radiation may be administered in a variety of fashions. For example, radiation may be electromagnetic or particulate in nature. Electromagnetic radiation useful in the practice of this invention includes, but is not limited, to x-rays and gamma rays. In a preferable embodiment, supervoltage x-rays (x-rays>=4 MeV) may be used in the practice of this invention. Particulate radiation useful in the practice of this invention includes, but is not limited to, electron beams, protons beams, neutron beams, alpha particles, and negative pi mesons. The radiation may be delivered using conventional radiological treatment apparatus and methods, and by intraoperative and stereotactic methods. Additional discussion regarding radiation treatments suitable for use in the practice of this invention may be found throughout Steven A. Leibel et al., Textbook of Radiation Oncology (1998) (publ. W.B. Saunders Company), and particularly in Chapters 13 and 14. Radiation may also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods may be used in the practice of this invention.

The amount of radiation delivered to the desired treatment volume may be variable. In a preferable embodiment, radiation may be administered in amount effective to cause the arrest or regression of the cancer, in combination with a compound of Formula I and pharmaceutical compositions described herein.

In a more preferable embodiment, radiation is administered in at least about 1 Gray (Gy) fractions at least once every other day to a treatment volume, still more preferably radiation is administered in at least about 2 Gray (Gy) fractions at least once per day to a treatment volume, even more preferably radiation is administered in at least about 2 Gray (Gy) fractions at least once per day to a treatment volume for five consecutive days per week.

In a more preferable embodiment, radiation is administered in 3 Gy fractions every other day, three times per week to a treatment volume.

In yet another more preferable embodiment, a total of at least about 20 Gy, still more preferably at least about 30 Gy, most preferably at least about 60 Gy of radiation is administered to a host in need thereof.

In one more preferred embodiment of the present invention 14 GY radiation is administered.

In another more preferred embodiment of the present invention 10 GY radiation is administered.

In another more preferred embodiment of the present invention 7 GY radiation is administered.

In a most preferable embodiment, radiation is administered to the whole brain of a host, wherein the host is being treated for metastatic cancer.

Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

This invention also relates to a method for the treatment of a disease or condition selected from the group consisting of autoimmune diseases (such as rheumatoid arthritis, juvenile arthritis, type I diabetes, lupus, systemic lupus erythematosus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), chronic obstructive pulmonary disease, infection associated with inflammation (such as viral inflammation (including influenza and hepatitis) and Guillian-Barre syndrome syndrome), chronic bronchitis, xenotransplantation, transplantation tissue rejection (chronic and acute), organ transplant rejection (chronic and acute), atherosclerosis, restenosis (including, but not limited to, restenosis following balloon and/or stent insertion), granulomatous diseases (including sarcoidosis, leprosy and tuberculosis), scleroderma, ulcerative colitis, Crohn's disease, and Alzheimer's disease, in a mammal, preferably a human, comprising administering to said mammal an amount of a compound of the Formula I, or a pharmaceutically acceptable salt thereof (including hydrates, solvates and polymorphs of said compound of Formula I or pharmaceutically acceptable salts thereof), that is effective in treating the disease or condition.

In one embodiment of this method, the disease or condition is selected from the group consisting of rheumatoid arthritis, juvenile arthritis, psoriasis, systemic lupus erythematosus, and osteoarthritis.

In another more specific embodiment of this method, the disease or condition is selected from the group consisting of rheumatoid arthritis and osteoarthritis.

In another embodiment of this method, the disease or condition is selected from the group consisting of chronic obstructive pulmonary disease, asthma acute respiratory distress syndrome, atherosclerosis, multiple sclerosis, and scleroderma.

Another embodiment of the invention is a method for preparing the compounds of formula I

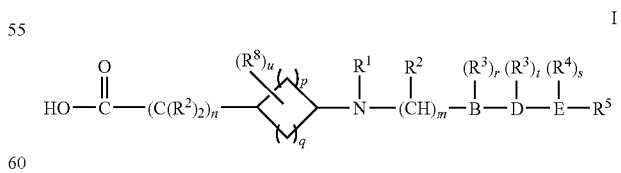

I and the pharmaceutically acceptable salts thereof, wherein B is selected from the group consisting of phenyl and a (5 to 6-membered)-heteroaryl ring;

D is selected from the group consisting of phenyl and a (5 to 6-membered)-heteroaryl ring;

E is selected from the group consisting of phenyl and a (5 to 6-membered)-heteroaryl ring;

$R^1$ is a radical selected from the group consisting of hydrogen, $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7$—$SO_2$—, $R^7$—C(O)—, $R^7O$—C(O)—, and $(R^7)_2N$—C(O)—;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7$—$SO_2$—, $R^7$—C(O)—, $R^7O$—C(O)—, and $(R^7)_2N$—C(O)—$R^1$ radicals may optionally be substituted by one to three moieties independently selected from the group consisting of hydrogen, hydroxy, halogen, —CN, $(C_1-C_6)$alkyl-, $(C_1-C_6)$alkoxy-, perhalo$(C_1-C_6)$alkyl-, $(C_3-C_7)$cycloalkyl-, $(C_2-C_9)$heterocyclyl-, $(C_6-C_{10})$aryl-, and $(C_1-C_{12})$heteroaryl-;

each $R^2$ is a radical independently selected from the group consisting of hydrogen, hydroxy, halogen, —CN, $(C_1-C_6)$alkyl-, $(C_2-C_6)$alkenyl-, $(C_2-C_{10})$alkynyl-, $(C_3-C_7)$cycloalkyl-, $(C_2-C_9)$heterocyclyl-, $(C_6-C_{10})$aryl-, and $(C_1-C_{12})$heteroaryl-;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, and $(C_1-C_{12})$heteroaryl-$R^2$ radicals may optionally be substituted by one to three moieties independently selected from the group consisting of hydrogen, hydroxy, halogen, —CN, $(C_1-C_6)$alkyl-, perhalo$(C_1-C_4)$alkyl-, perhalo$(C_1-C_4)$alkoxy-, $(C_3-C_7)$cycloalkyl-, $(C_2-C_9)$heterocyclyl-, $(C_6-C_{10})$aryl-, and $(C_1-C_{12})$heteroaryl-;

each $R^3$ is a radical independently selected from the group consisting of hydrogen, halogen, hydroxy, —CN, $(C_1-C_6)$alkyl-, $(C_2-C_6)$alkenyl-, $(C_2-C_6)$alkynyl-, $(C_3-C_7)$cycloalkyl-, $(C_1-C_6)$alkoxy-, perhalo$(C_1-C_6)$alkyl-, and perhalo$(C_1-C_6)$alkoxy-;

each $R^4$ is a radical independently selected from the group consisting of hydrogen, halogen, hydroxy, —CN, —N($R^6$)$_2$, $(C_1-C_6)$alkyl-, $(C_2-C_6)$alkenyl-, $(C_3-C_6)$alkynyl-, $(C_1-C_6)$alkoxy-, perhalo$(C_1-C_6)$alkyl-, $(C_1-C_6)$alkyl-S(O)$_k$—, $R^{10}$C(O)N($R^{10}$)—, $(R^{10})_2$NC(O)—, $R^{10}$C(O)—, $R^{10}$OC(O)—, $(R^{10})_2$NC(O)N($R^{10}$)—, $(R^{10})_2$NS(O)—, $(R^{10})_2$NS(O)$_2$—, $(C_3-C_7)$cycloalkyl-, $(C_6-C_{10})$aryl-, $(C_2-C_9)$heterocyclyl-, and $(C_1-C_{12})$heteroaryl-;

wherein each of said $(C_1-C_6)$alkyl-, $(C_2-C_6)$alkenyl-, $(C_3-C_6)$alkynyl-, $(C_1-C_6)$alkoxy-, $(C_1-C_6)$-alkyl-S(O)$_k$—, $R^{10}$C(O)N($R^{10}$)—, $(R^{10})_2$NC(O)—, $R^{10}$C(O)—, $R^{10}$OC(O)—, $(R^{10})_2$NC(O)N($R^{10}$)—, $(R^{10})_2$NS(O)—, $(R^{10})_2$NS(O)$_2$—, $(C_3-C_7)$cycloalkyl-, $(C_6-C_{10})$aryl-, $(C_2-C_9)$heterocyclyl-, and $(C_1-C_{12})$heteroaryl-$R^4$ radicals may optionally be substituted from one to five moieties independently selected from the group consisting of halogen, hydroxy, —CN, $(C_1-C_6)$alkyl-, $(C_3-C_7)$cycloalkyl, —$(C_1-C_6)$alkoxy and -perhalo$(C_1-C_6)$alkoxy;

$R^5$ is a radical selected from the group consisting of hydrogen, halogen, —CN, $(C_1-C_{10})$alkyl-, $(C_1-C_6)$alkoxy-, $(C_2-C_{10})$alkenyl-, $(C_2-C_{10})$alkynyl-, $(C_3-C_7)$cycloalkyl-, $(C_6-C_{10})$aryl-, $(C_2-C_9)$heterocyclyl-, $(C_1-C_{12})$heteroaryl-, $(C_3-C_7)$cycloalkyl-O—, $(C_6-C_{10})$aryl-O—, $(C_2-C_9)$heterocyclyl-O—, $(C_1-C_{12})$heteroaryl-O—, $R^7$—S—, $R^7$—SO—, $R^7$—$SO_2$—, $R^7$—C(O)—, $R^7$—C(O)—O—, $R^7O$—C(O)—, and $(R^7)_2N$—C(O)—;

wherein each of said $(C_1-C_{10})$alkyl-, $(C_1-C_6)$alkoxy- and $(C_2-C_{10})$alkynyl-$R^5$ radicals may optionally be substituted with from one to five moieties independently selected from the group consisting of halogen, hydroxy, —CN, $(C_1-C_6)$alkyl-, $(C_3-C_7)$cycloalkyl-, $(C_6-C_{10})$aryl-, $(C_1-C_6)$alkoxy-, $(C_2-C_9)$heterocyclyl-, and $(C_1-C_{12})$heteroaryl-;

wherein each of said $(C_3-C_7)$cycloalkyl- and $(C_3-C_7)$cycloalkyl-O—$R^5$ radicals may optionally be substituted with from one to five moieties independently selected from the group consisting of halogen, hydroxy, —CN, $(C_1-C_6)$alkyl-, $(C_6-C_{10})$aryl-, $(C_1-C_6)$alkoxy-, $(C_2-C_9)$heterocyclyl-, and $(C_1-C_{12})$heteroaryl-;

wherein each of said $(C_6-C_{10})$aryl-, $(C_2-C_9)$heterocyclyl-, $(C_1-C_{12})$heteroaryl-, $(C_6-C_{10})$aryl-O—, $(C_2-C_9)$heterocyclyl-O—, and $(C_1-C_{12})$heteroaryl-O—$R^5$ radicals may optionally be substituted with from one to five moieties independently selected from the group consisting of halogen, hydroxy, —CN, $(C_1-C_6)$alkyl-, and $(C_1-C_6)$alkoxy-;

wherein each of said $R^7$—S—, $R^7$—SO—, $R^7$—$SO_2$—, $R^7$—C(O)—, $R^7$—C(O)—O—, $R^7$—C(O)—, and $(R^7)_2N$—C(O)—$R^5$ radicals may optionally be substituted with from one to five moieties independently selected from the group consisting of halogen, hydroxy, —CN, $(C_1-C_6)$alkyl-, $(C_3-C_7)$cycloalkyl, and $(C_1-C_6)$alkoxy-;

wherein each of aforesaid $(C_1-C_6)$alkyl-, $(C_1-C_6)$alkoxy-, $(C_6-C_{10})$aryl-, $(C_1-C_6)$alkoxy-, $(C_2-C_9)$heterocyclyl-, and $(C_1-C_{12})$heteroaryl-moieties for each of aforesaid $R^5$ radicals may optionally be substituted with one to five halogen groups;

optionally said $R^5$ radical and one $R^4$ radical or two $R^4$ radicals may be taken together with E to form an (8 to 10-membered)-fused bicyclic ring optionally containing 1 to 4 heteroatoms selected from the group consisting of O, S, or N($R^6$);

wherein said (8 to 10-membered)-fused bicyclic ring is additionally optionally substituted with one to two oxo (=O) groups;

each $R^6$ is a bond or a radical independently selected from the group consisting of hydrogen, $(C_1-C_6)$alkyl-, —CN, and perhalo$(C_1-C_6)$alkyl-;

each $R^7$ is a radical independently selected from the group consisting of hydrogen, —CN, $(C_1-C_6)$alkyl-, perhalo$(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, and $(C_1-C_{12})$heteroaryl-;

each $R^8$ is a radical independently selected from the group consisting of hydrogen, hydroxy, halogen, —CN, —NH($R^9$), $(C_1-C_6)$alkyl-, perhalo$(C_1-C_6)$alkyl- and $(C_1-C_6)$alkoxy-;

wherein each of said $(C_1-C_6)$alkyl- and $(C_1-C_6)$alkoxy-$R^8$ radicals is optionally substituted from one to five moieties selected from the group consisting of perhalo$(C_1-C_6)$alkyl-, —O($R^9$) and —N($R^9$)$_2$;

each $R^9$ is a radical independently selected from the group consisting of hydrogen, $(C_1-C_6)$alkyl-, $(C_2-C_{10})$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-, $R^7$—S—, $R^7$—SO—, $R^7$—$SO_2$—, $R^7$—C(O)—, $R^7$—C(O)—O—, $R^7O$—C(O)—, and $(R^7)_2N$—C(O)—;

wherein each of said $(C_1-C_6)$alkyl-, $(C_2-C_6)$alkenyl-, $(C_2-C_6)$alkynyl-, $(C_3-C_7)$cycloalkyl-, $(C_2-C_9)$heterocyclyl-, $(C_6-C_{10})$aryl-, $(C_1-C_{12})$heteroaryl-$R^9$ radicals is optionally substituted by one to three moieties independently selected from the group consisting of hydrogen, hydroxy, halogen, —CN, $(C_1-C_6)$alkyl-, $(C_1-C_6)$alkoxy-, perhalo$(C_1-C_6)$alkyl-, $(C_3-C_7)$cycloalkyl-, $(C_2-C_9)$heterocyclyl-, $(C_6-C_{10})$aryl-, and $(C_1-C_{12})$heteroaryl-;

each $R^{10}$ is a radical selected from the group consisting of hydrogen and $(C_1-C_6)$alkyl-;

k is an integer from 0 to 2;

m and n are each independently an integer from 0 to 3;

p is an integer from 1 to 2;

q is an integer from 0 to 2; and r, s, t and u are each independently an integer from 0 to 4, which method comprises: hydrolysis of a compound of formula II

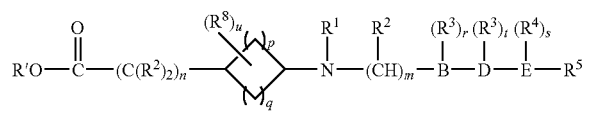

II wherein R' is $(C_1-C_4)$alkyl and B, D, E, $R^1$, $R^2$, $R^3$, $R^4$, $R^5$, $R^8$, m, n, p, q, r, s, t and u are as defined for formula I.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; and (4) any tumors that proliferate by receptor tyrosine kinases.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

DETAILED DESCRIPTION OF THE INVENTION

The compounds of the present invention (I and Ia) are readily prepared according to synthetic methods familiar to those skilled in the art. Scheme 1 illustrates a general synthetic sequence for preparing compounds of the present invention where, unless otherwise indicated, B, D, E, $R^1$, $R^2$, $R^3$, $R^4$, $R^5$, $R^6$, $R^7$, $R^8$, m, n, r, s, t, and u and structural formula I and Ia in the reaction schemes and discussion that follow are as defined above.

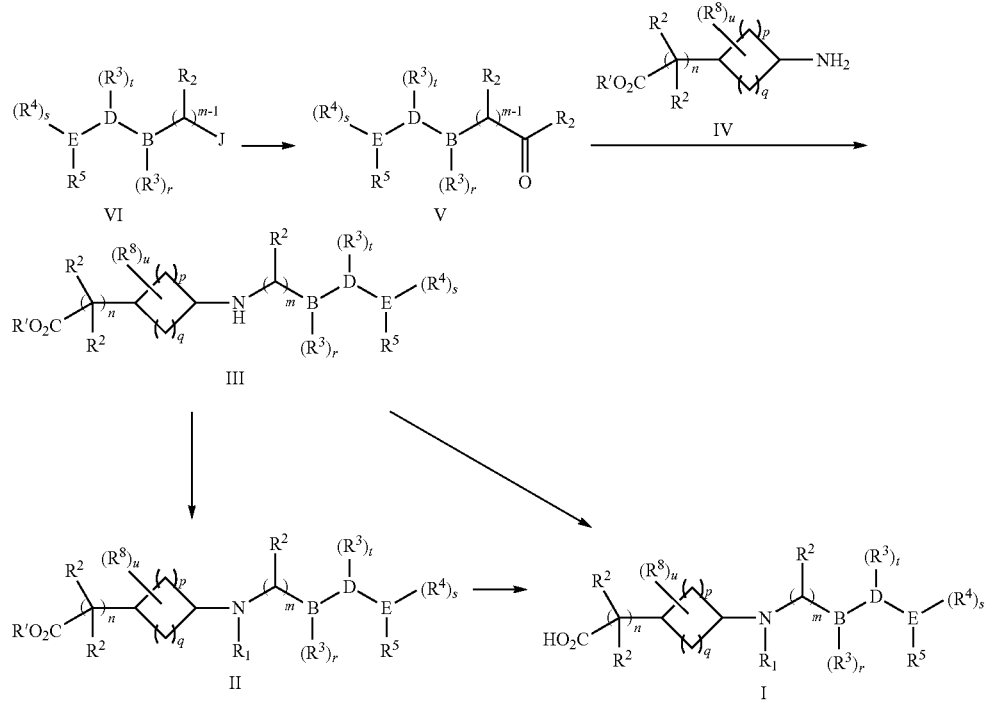

Scheme 1

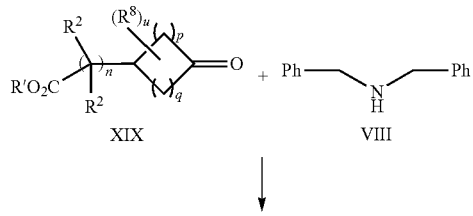

Scheme 2

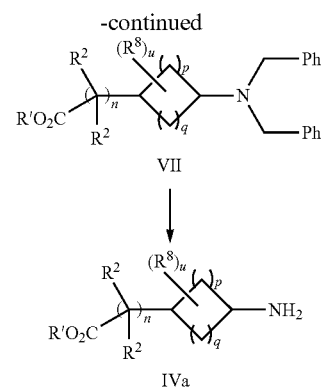

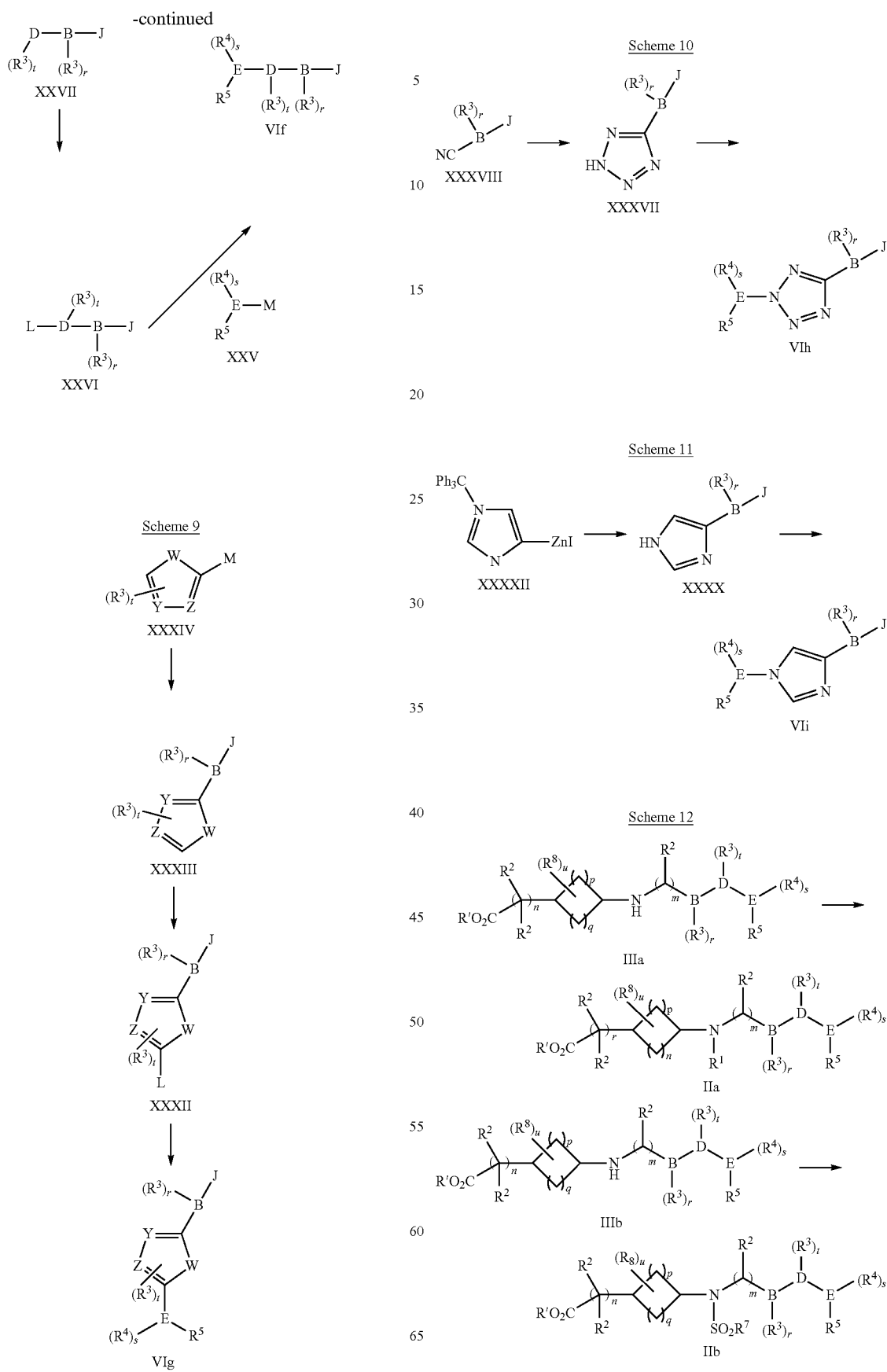

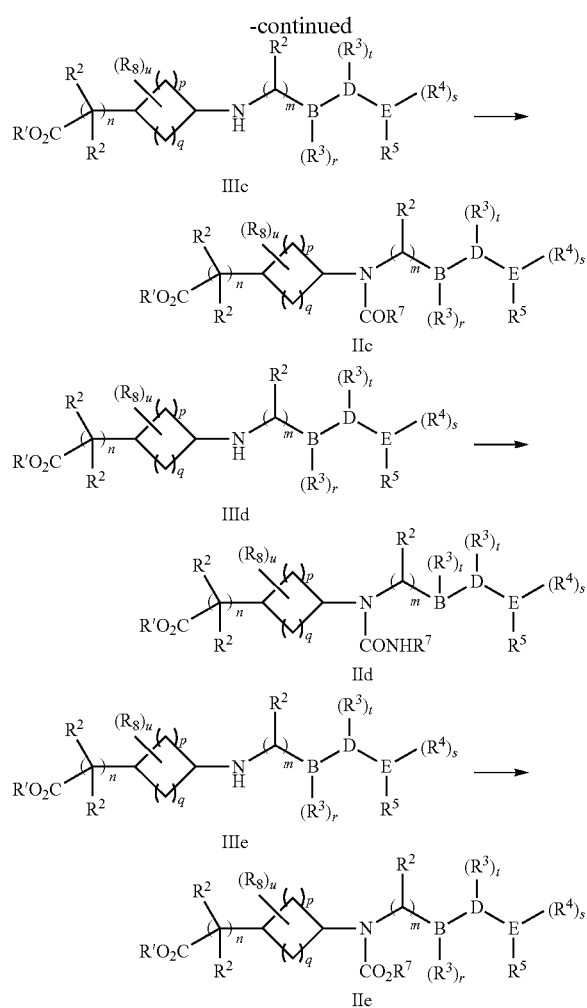

Scheme 1 illustrates a method of synthesizing compounds of formula I in a multistep synthesis from compounds of formula VI. Referring to Scheme I, compounds of formula I can be prepared from compounds of formula II, wherein R' is ($C_1$-$C_4$) alkyl, by hydrolysis. The hydrolysis is typically carried out using acidic or basic conditions, optionally in the presence of a suitable organic co-solvent, e.g., methanol, ethanol, tetrahydrofuran (THF) or dioxane. Suitable acids include hydrochloric acid or trifluoroacetic acid. Suitable bases include aqueous sodium, lithium or potassium hydroxide. Temperatures for the hydrolysis may range from about 0° C. to 150° C., more preferably about 22° C. The reaction may be performed in a microwave at or above atmospheric pressure.

Compounds of formula II, wherein $R^1$ is other than hydrogen, can be prepared by treating compounds of formula III with an appropriate alkylating or acylating agent in the presence of a suitable base such as triethylamine, diisopropylethylamine or pyridine and a suitable solvent, or mixture of solvents, such as dichloromethane, THF or dimethylformamide (DMF) at a temperature at or above 22° C. Suitable alkylating agents include alkyl halides and dimethylsulfate.

Alternatively, a compound of formula II can be prepared by a reductive amination by reaction of a compound of formula III with an appropriate aldehyde (e.g. formaldehyde) and an appropriate reducing agent in the presence of a suitable solvent or mixture of solvents at a temperature from about −10° C. to about 40° C., preferably 22° C. Suitable reducing agents include sodium cyanoborohydride, sodium triacetoxyborohydride, and sodium borohydride. Sodium triacetoxyborohydride is preferred. Suitable solvents include methanol, ethanol, dichloroethane, THF, methylene chloride and mixtures thereof, optionally in the presence of an acid or base, such as acetic acid or triethylamine, respectively.

Compounds of formula I, wherein $R^1$ is hydrogen, can be prepared directly from compounds of formula III, wherein R' is ($C_1$-$C_4$) alkyl, by hydrolysis. The conditions for the hydrolysis reaction are as described above for the synthesis of compounds of formula I from compounds of formula II described above.

Compounds of formula III, wherein m is 1 to 3, can be prepared by reductive amination by reacting a compound of formula V with a compound of formula IV. Reductive aminations are typically carried out with a suitable reducing agent in the presence of a suitable solvent or mixture of solvents at a temperature from about −10° C. to about 40° C., preferably 22° C. Suitable reducing agents include sodium cyanoborohydride, sodium triacetoxyborohydride, and sodium borohydride. Sodium triacetoxyborohydride is preferred. Suitable solvents include methanol, ethanol, dichloroethane, THF, methylene chloride and mixtures thereof, optionally in the presence of an acid or base, such as acetic acid or triethylamine, respectively.

Compounds of formula III, wherein m is zero (0), can be prepared by coupling of a compound of formula IV with a compound of formula VI',

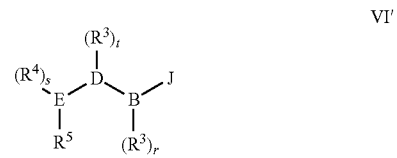

VI' wherein J is halogen. The coupling reaction is typically carried out using basic conditions (e.g. potassium phosphate) in the presence of a suitable organic solvent (e.g. dimethylsulfoxide). Temperatures for the reaction may range from about 22° C. to 200° C., more preferably about 200° C. The reaction may be performed in a microwave at or above atmospheric pressure. Compounds of formula VI' can be prepared by methods of Schemes 3, 4, 5, 6, 7, 8, 9, 10, and 11.

Compounds of formula V can be prepared from compounds of formula VI, wherein J is $CO_2R''$, $CHR^2OR'''$, acetal, hemiacetal, N-alkoxy-N-alkyl carboxamides or halogen, R'' is hydrogen, t-butyl, methyl or ethyl and R''' is H or an appropriate protecting group (see Greene & Wuts, eds., *Protecting Groups in Organic Synthesis*, John Wiley & Sons, Inc.). Specifically, compounds of formula V can be prepared from compounds of formula VI, wherein J is $CO_2R''$, via a two step process of reduction followed by oxidation, according to methods well know to those skilled in the art. The reduction step is affected with a suitable reducing agent in the presence of a suitable solvent or mixture of solvents at a temperature from about −78° C. to about 22° C. to reduce the ester to an intermediate alcohol. Reducing agents are well known to those skilled in the art. Suitable reducing agents included borane, diisobutylaluminum hydride or sodium borohydride or combinations thereof. Suitable solvents are THF, dichloromethane, dichloroethane, toluene or mixtures thereof, where the reducing agent is sodium borohydride, the preferred solvent is a protic solvent, such as methanol or ethanol.

The oxidation of the resulting alcohol from the reduction step to the corresponding carbonyl compound of formula V may be accomplished using a selective oxidizing agent such as pyridinium chlorochromate (PCC), Dess Martin reagent, Swern oxidation or manganese dioxide ($MnO_2$). References for such conversions are readily available (e.g., K. B. Wiberg, *Oxidation in Organic Chemistry*, Part A, Academic Press Inc, N.Y., 69-72 (1965)). Preferably, the oxidation reaction is conducted in a suitable solvent or solvent mixture such as methylene chloride. Suitable temperatures for the aforesaid reaction range from about −78° C. to about 22° C., preferably from about 20° C. to about 25° C. (i.e. room temperature) for Dess Martin and PCC oxidations. The reaction is complete within about 0.5 hours to about 24 hours.

Alternatively, compounds of formula VI wherein J is $CHR^2OR'''$, acetal, hemiacetal, or N-alkoxy-N-alkyl carboxamides can be converted to a compound of formula V by methods known by those skilled in the art (see Larock, *Comprehensive Organic Transformations, A Guide to Functional Group Preparations*, VCH Publishers, Inc.).

Alternatively, compounds of formula VI, wherein J is halogen, can be used to prepare a compound of formula V, wherein $R^2$ is H, via a metal catalyzed cross coupling reaction with cyamide, followed by reduction. Metal catalyzed cross coupling reactions are well known to those skilled in the art. One well known coupling method involves the coupling of compounds of formula VI, wherein J is halogen, e.g. Cl, in the presence of a suitable palladium (0) catalyst, a suitable metal, and a suitable solvent, or mixture of solvents, at a temperature of about 22° C. to about 80° C., preferably, 80° C. Suitable palladium (0) catalysts include tetrakis (triphenylphosphine) palladium (O) $(Pd(PPh_3)_4)$, tris(dibenzylideneacetone)dipalladium(O) $(Pd_2(dba)_3)$, di(dibenzylideneacetone) palladium (O) $(Pd(dba)_2)$, palladium acetate $(Pd(OAc)_2)$. Suitable metals include Mg, Zn, Zr and B. Zn is preferred. Suitable solvents include toluene, benzene, and DMF or an ethereal solvent, preferably dioxane. Such conditions are reviewed in Negishi, E-I; Liu, F. in *Metal-catalyzed Cross-coupling Reactions*; Deiderich, F; Stang, P. J. Eds; Wiley; New York, 1998, Chapter 1.

The resulting nitrile may then be reduced to the corresponding carbonyl compound of formula V. The reduction reaction conditions are affected with a suitable reducing agent in the presence of a suitable solvent or mixture of solvents at a temperature from about −78° C. to about 0° C. Reducing agents are well known to those skilled in the art. The following conditions are preferred: diisobutylaluminum hydride in dichloromethane at −78° C.

Alternatively, compounds of formula V can be prepared from the compounds of formula VI, wherein J is halogen by a metal-halogen exchange reaction using a strong base (e.g. n-BuLi, iPrMgBr and sec-BuLi) in the presence of an electrophile (e.g. DMF), and a suitable solvent, or mixture of solvents, at a temperature from about −78° C. to about 22° C., preferably −78° C. Suitable solvents include diethyl ether, toluene, benzene, or THF.

Compounds of the formula VI can be prepared by the methods of Schemes 3 through 11. Compounds of the formula IV can be prepared by the methods of Scheme 2.

Scheme 2 refers to the preparation of compounds of formula IV (IVa) which can be converted to a compound of formula I according to the method of Scheme I. Referring to Scheme 2, compounds of formula IVa, wherein R' is ($C_1$-$C_4$) alkyl or benzyl, can be prepared by hydrogenation of a tertiary amine of formula VII, wherein Ph is optionally substituted phenyl. Hydrogenation may be affected with hydrogen gas ($H_2$), using catalysts such as palladium on carbon (Pd/C), palladium hydroxide $(Pd(OH)_2)$ or platinum on carbon (Pt/C) in an appropriate solvent such as methanol, ethanol, THF, dioxane or ethyl acetate at or above atmospheric pressure and a temperature from about 10° C. to about 60° C., preferably 22° C. (see *Catalytic Hydrogenation in Organic Synthesis*, Paul Rylander, Academic Press Inc., San Diego, 31-63 (1979)). The following conditions are preferred: Pd on carbon at 25° C. and 50 psi of hydrogen gas pressure. This method also provides a means for introduction of hydrogen isotopes (i.e., deuterium, tritium) by replacing $^1H_2$ with $^2H_2$ or $^3H_2$ in the above procedure.

Compounds of formula VII can be prepared by reductive amination by reacting a compound of formula XIX with a compound of formula VIII. Reductive amination conditions are described above. Sodium triacetoxyborohydride as reducing agent and acetic acid as solvent are preferred. Compounds of formula VII (isomeric mixtures) can be separated to obtain stereoisomers by methods well known to those skilled in the art such as chromatography or recrystallization techniques, for example, chiral chromatography using a 2×25 cm Chiralpak AD-H preparatory HPLC column (UV detection @ 210 nM) with a 85:15 (vol:vol) mixture of heptane:ethanol as the mobile phase at a rate of 10 mL/min. Compounds of the formula VIII are commercially available or can be made by methods well know those so skilled in the art. Compounds of formula XIX can be made by methods well known to those skilled in the art (see *J. Org. Chem.* 1988 53, 3841-3843).

Scheme 3 refers to the preparation of a compound of formula VIa, wherein J is halogen, $CHR_2OR'''$ or $CO_2R''$, R''' is hydrogen or an appropriate protecting group and R'' is hydrogen, t-butyl, methyl or ethyl, which can be converted to a compound of formula I according to the method of Scheme I. Referring to Scheme 3, a compound of formula VIa can be prepared in a 2 step procedure by a coupling reaction of a compound of formula X with a compound of formula XI, followed by cyclization/dehydration using an appropriate dehydrating agent. The coupling reaction is typically carried out using a suitable coupling agent in the presence of a suitable solvent or mixture of solvents. Suitable coupling agents are 1,1'-carbonyldiimidizole, N,N'-dicyclohexylcarbodiimide, 1-(3-dimethylaminopropyl)-3-ethylcarbodiimide and 1-(hydroxyl)benzotrazole. Suitable solvents are acetonitrile, THF and DMF. Temperatures for the coupling reaction may be at or above 22° C., preferably 22° C. The dehydration reaction is typically carried out using a suitable base (e.g. tetra-n-butylammonium fluoride) in an appropriate solvent (e.g. THF) at or above 22° C. to obtain 1,2,4-oxadiazoles. Other methods to prepare 1,2,4-oxadiazoles are potentially pertinent to the present invention and are known to those skilled in the art and have been reviewed in the literature (see "1,2,3- and 1,2,4-oxadiazoles" in *Comprehensive Heterocyclic Chemistry*, Volume 6, Potts, K. T., Editor, Pergamon Press, 1984).

Many acids of formula X are available from commercial sources or by methods known to those skilled in the art (see Larock, *Comprehensive Organic Transformations, A Guide to Functional Group Preparations*, VCH publishers, Inc.).

Compounds of formula XI can be prepared from compounds of formula XII by reacting a hydroxylamine, such as hydroxylamine hydrochloride, and a suitable base in the presence of a suitable solvent or mixture of solvents. Suitable bases include sodium bicarbonate, triethylamine or diisopropylethylamine, preferably sodium bicarbonate. Suitable solvents include methanol, ethanol or DMF, preferably DMF.

The reaction is carried out at or above 22° C.

Compounds of the formula XII are commercially available or can be made by methods well know to those so skilled in the art.

Scheme 4 refers to an alternative preparation of a compound of formula VI (VIb) wherein J is halogen, $CHR_2OR'''$ or $CO_2R''$, $R'''$ is hydrogen or an appropriate protecting group and $R''$ is hydrogen, t-butyl, methyl or ethyl, which can be converted to a compound of formula I according to the method of Scheme 1. Referring to Scheme 4, compounds of formula VIb can be prepared in a 2 step procedure by a coupling reaction of a compound of formula XIII

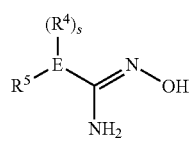
XIII with a compound of formula XIV, followed by cyclization/dehydration using an appropriate dehydrating agent. The coupling reaction is typically carried out using a suitable coupling agent, a suitable base in the presence of a suitable solvent or mixture of solvents. Suitable coupling agents are 1,1'-carbonyldiimidizole, N,N'-dicyclohexylcarbodiimide, 1-(3-dimethylaminopropyl)-3-ethylcarbodiimide and 1-(hydroxyl)benzotriazole. Suitable bases include triethylamine or diisopropylethylamine. Suitable solvents include dichloromethane, acetonitrile, THF and DMF. Temperatures for the coupling reaction may range from about at or above 22° C., preferably 22° C. The dehydration reaction is typically carried out using a suitable base (e.g. tetra-n-butylammonium fluoride) in an appropriate solvent (e.g. THF) at or above 22° C. to obtain 1,2,4-oxadiazoles.

Compounds of the formula XIII are commercially available or can be made by methods well know those so skilled in the art Scheme 5 refers to an alternative preparation of a compound of formula VI (VIc) wherein J is halogen, $CHR_2OR'''$ or $CO_2R''$, $R'''$ is hydrogen or an appropriate protecting group and $R''$ is hydrogen, t-butyl, methyl or ethyl, which can be converted to a compound of formula I according to the method of Scheme 1. Referring to Scheme 5, compounds of formula VIc can be prepared by a cyclization reaction from compounds of formula XV according to dehydration methods known to those skilled in the art to form 1,3,4-oxadiazoles. The cyclization reaction is typically carried out using a suitable dehydrating reagent agent, for example the Burgess reagent [(methoxycarbonylsulfamoyl)triethylammonium hydroxide], in the presence of a suitable solvent or mixture of solvents. Cyclization may require added base, in which case suitable bases including triethylamine, diisopropylethylamine, tetra-n-butylammonium fluoride or pyridine. Suitable solvents include dichloromethane, toluene, acetonitrile, THF, N-methylpyrrolidinone and DMF. Temperatures for the coupling reaction may range from about 0° C. to 150° C.

Compounds of formula XV can be prepared by a coupling reaction from compounds of formula XVII with a compound of formula

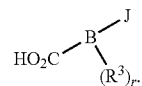
XVI

The coupling reaction is typically carried out using a suitable coupling agent, a suitable base in the presence of a suitable solvent or mixture of solvents. Suitable coupling agents are N,N-dimethyl(chlorosulphonyl)methaniminium chloride (see J. Chem. Research (S), 1991 9, 260.), 1,1'-carbonyldiimidizole, O-benzotriazol-1-yl-N,N,N',N'-tetramethyluronium hexafluorophosphate (HBTU), N,N'-dicyclohexylcarbodiimide, 1-(3-dimethylaminopropyl)-3-ethylcarbodiimide and 1-(hydroxyl)benzotriazole. Suitable bases include triethylamine, diisopropylethylamine or sodium bicarbonate. Suitable solvents include acetonitrile, dichloromethane, toluene, THF, N-methylpyrrolidinone and DMF. Temperatures for the coupling reaction may range from about at or above 0° C., preferably 22° C.

Compounds of formula XVII can be prepared from compounds of formula XVIII by an acylation reaction. Acylation of a compound of formula XVIII to obtain a compound of formula XVII is conducted with hydrazine and an activated carboxylic acid (e.g. 1,1'-carbonyldiimidizole, O-benzotriazol-1-yl-N,N,N',N'-tetramethyluronium hexafluorophosphate (HBTU), N,N'-dicyclohexylcarbodiimide, 1-(3-dimethylaminopropyl)-3-ethylcarbodiimide and 1-(hydroxyl)benzotriazole) in the presence of a base (if necessary), such as triethylamine, diisopropylethylamine or sodium bicarbonate, in a solvent, such as acetonitrile, dichloromethane, toluene, THF, N-methylpyrrolidinone and DMF, preferably DMF or mixtures thereof, for a time period of about 12 h, at a temperature at or above 22° C.

Compounds of the formulas XVI and XVIII are commercially available or can be made by methods well know those so skilled in the art Scheme 6 refers to an alternative preparation of a compound of formula VI (VId) wherein J is halogen, $CHR_2OR'''$ or $CO_2R''$, $R'''$ is hydrogen or an appropriate protecting group and $R''$ is hydrogen, t-butyl, methyl or ethyl, which can be converted to a compound of formula I according to the method of Scheme 1. Referring to Scheme 6, compounds of formula VId can be prepared from compounds of formula XIX by a cyclization reaction. The compound of formula XIX is treated with a suitable sulfur transfer agent in a suitable solvent, or mixture of solvents, at a temperature about 80° C. Suitable sulfur transfer agent includes Lawesson's reagent (2,4-bis(40methoxyphenyl)-1,3-dithia-2,4-diphosphetane-2, 4-disulfide), followed by heating with phosphorous pentasulfide. Suitable solvents include pyridine.

Compounds of formula XIX can be prepared by a coupling reaction from compounds of formula XX with compounds of formula XXVI

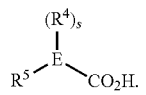
XXVI

The coupling reaction is carried out using a suitable coupling agent and a suitable base in the presence of a suitable solvent or mixture of solvents. Suitable coupling agents include 1,1'- carbonyldiimidizole, O-benzotriazol-1-yl-N,N,N',N'-tetramethyluronium hexafluorophosphate (HBTU), N,N'-dicyclohexylcarbodiimide, 1-(3-dimethylaminopropyl)-3-ethylcarbodiimide and 1-(hydroxyl)benzotriazole. Suitable bases (if necessary) include triethylamine, diisopropylethylamine or sodium bicarbonate. Suitable solvents include acetonitrile, dichloromethane, toluene, THF, N-methylpyrrolidinone and DMF. Temperatures for the coupling reaction may range from about at or above 0° C., preferably 22° C. Alternatively, compounds of formula XXVI can be converted to an acid chloride, acid anhydride, acyl imidazole by methods known to those skilled in the art, which may also be used in the presence of the aforementioned bases and solvents to obtain XIX.

Compounds of formula XX can be prepared by an acylation reaction of a compound of formula XXI with hydrazine by the method previously described in Scheme 4 or by methods well known to those so skilled in the art.

Scheme 7 refers to an alternative preparation of a compound of formula VI (VIe) wherein J is halogen, $CHR_2OR'''$ or $CO_2R''$, $R'''$ is hydrogen or an appropriate protecting group and $R''$ is hydrogen, t-butyl, methyl or ethyl, which can be converted to a compound of formula I according to the method of Scheme 1. Referring to Scheme 7, compounds of formula VIe can be prepared by a condensation reaction from a compound of formula XXIII with a compound of formula XXII,

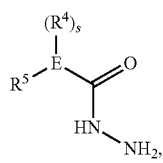

XXII according to methods known to those skilled in the art to form 1,2,4-triazoles (e.g. Tetrahedron Lett. 1987 28, 5133-516). The condensation reaction is typically carried out in an alcoholic solvent, such as ethanol.

Compounds of formula XXIII can be prepared by treating a compound of formula XXIV with chloromethylaluminum amide as described by Garigipati (e.g. *Tetrahedron Lett.* 1991 31, 1969-72).

Compounds XX, XXI, and XXII, and XXIV are commercially available or can be made by methods well know those so skilled in the art.

Scheme 8 refers to an alternative preparation of a compound of formula VI (VIf), wherein J is halogen, $CHR_2OR'''$ or $CO_2R''$, $R'''$ is H or an appropriate protecting group, and $R''$ is H, t-butyl, methyl or ethyl, which can be converted to a compound of formula I according to the method of Scheme 1. Referring to Scheme 8, a compound of formula VIf, can be prepared by a coupling reaction from a suitable organometallic reagent of the formula XXV wherein M is $B(OR)_2$, $B(OH)_2$, $SnR_3$, ZnA, MgA, Li with a compound of formula XXVI, wherein L is Cl, Br or I, in the presence of a suitable palladium (0) or nickel (0) catalyst, and a suitable solvent, or mixture of solvents, at a temperature at or above 22° C. Depending on the nature of XXVI and XXV, use of various ligands for palladium (0) or nickel (0) may be needed to affect the aforementioned transformations efficiently. Suitable ligands (e.g. triaryl phosphine ligand, tri(t-butyl)phosphine, 1,1-bis(diphenylphosphanyl)ferrocene (DPPF), 2,2'-bis(diphenylphosphanyl)-1,1'-binaphthyl (BINAP), tri(ortho-tolyl)phosphine, or PHANEPHOS) and/or palladium (0) or nickel (0) complexes include, but is not limited to, tris(dibenzylidene acetone)dipalladium(0) ($Pd_2(dba)_3$), di(dibenzylidene acetone) palladium(0) ($Pd(dba)_2$) or palladium acetate ($Pd(OAc)_2$).

Compounds of formula XXVI can be prepared from a compound of formula XXVII by reaction with a suitable halogenation reagent such as N-iodosuccinamide, N-chlorosuccinamide, phenyl trimethylammonium tribromide, N-bromosuccinamide, pyridinium bromide perbromide, iodine, $Br_2$ or $Br_2$—$Ph_3P$. The reaction may be carried out in a suitable solvent, such as methanol, ethanol, dichloromethane, chloroform, acidic acid, typically under acidic conditions in the presence of salts, such as sodium or potassium acetate.

Compounds of formula XXVII can be prepared by a coupling reaction from a compound of formula XVIII with a compound of the formula XXIX, wherein A is Cl, Br, I, or $OSO_3CF_3$, under conditions analogous to those for coupling of compounds XXVI and XXV.

Similarly, compounds of formula VIf can be prepared by a coupling reaction from a suitable organometallic reagent of the formula XXX, wherein M is $B(OR)_2$, $B(OH)_2$, $SnR_3$, ZnA, MgA, Li with a compound of formula XXIX, in the presence of a suitable palladium (0) or nickel (0) catalyst, and a suitable solvent, or mixture of solvents, at a temperature at or above 22° C. Depending on the nature of XXIX and XXX, use of various ligands for palladium (0) or nickel (0) may be needed to affect the aforementioned transformations efficiently. Suitable ligands (e.g. triaryl phosphine ligand, tri(t-butyl)phosphine, 1,1-bis(diphenylphosphanyl)ferrocene (DPPF), 2,2'-bis(diphenylphosphanyl)-1,1'-binaphthyl (BINAP), tri(ortho-tolyl)phosphine, or PHANEPHOS) and/or palladium (0) or nickel (0) complexes include, but is not limited to, tris(dibenzylidene acetone)dipalladium(0) ($Pd_2(dba)_3$), di(dibenzylidene acetone) palladium(0) ($Pd(dba)_2$) or palladium acetate ($Pd(OAc)_2$).

Compounds of the formula XXIX, XXV, XVIII, and XXX are commercially available or can be made by methods well know those so skilled in the art. Organometallic reagents XXVIII, XXV, and XXX are either commercially available or can be prepared from an appropriate heteroaryl halide by well known methods dependent on the nature of such organometallic reagents.

Scheme 9 refers to an alternative preparation of a compound of formula VI (VIg), wherein J is halogen, $CHR_2OR'''$ or $CO_2R''$, $R'''$ is H or an appropriate protecting group and $R''$ is H, t-butyl, methyl or ethyl, which can be converted to a compound of formula I according to the method of Scheme 1. Referring to Scheme 9, a compound of formula VIg, wherein W is O, S, or N, Y is C or N and Z is C or N can be prepared by a coupling reaction from a suitable organometallic reagent of the formula XXXI

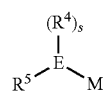

XXXI wherein M is $B(OR)_2$, $B(OH)_2$, $SnR_3$, ZnA, MgA, Li with a compound of formula XXXII, wherein L is Cl, Br or I, in the presence of a suitable palladium (0) or nickel (0) catalyst, and a suitable solvent, or mixture of solvents, at a temperature at or above 22° C. Depending on the nature of XXXII and XXXI, use of various ligands for palladium (0) or nickel (0) may be needed to affect the aforementioned transformations efficiently. Suitable ligands (e.g. triaryl phosphine ligand, tri(t-butyl)phosphine, 1,1-bis(diphenylphosphanyl)ferrocene (DPPF), 2,2'-bis(diphenylphosphanyl)-1,1'-binaphthyl (BINAP), tri(ortho-tolyl)phosphine, or PHANEPHOS) and/or palladium (0) or nickel (0) complexes include, but is not limited to, tris(dibenzylidene acetone)dipalladium(0) (Pd$_2$(dba)$_3$), di(dibenzylidene acetone) palladium(0) (Pd(dba)$_2$) or palladium acetate (Pd(OAc)$_2$).

Compounds of formula XXXII can be prepared from a compound of formula XXXIII by reaction with a suitable halogenation reagent such as N-iodosuccinamide, N-chloropsuccinamide, phenyl trimethylammonium tribromide, N-bromosuccinamide, pyridinium bromide perbromide, iodine, Br$_2$ or Br$_2$—Ph$_3$P. The reaction may be carried out in a suitable solvent, such as methanol, ethanol, dichloromethane, chloroform, acidic acid, typically under acidic conditions in the presence of salts, such as sodium or potassium acetate.

Compounds of formula XXXIII can be prepared by a coupling reaction from a compound of formula XXXIV with a compound of the formula XXXV,

XXXV wherein A is Cl, Br, I, or OSO$_3$CF$_3$, under conditions analogous to those for coupling of compounds XXXII and XXXI.

Compounds of the formula XXXV, XXXIV and XXXI are commercially available or can be made by methods well know those so skilled in the art. Organometallic reagents XXXIV and XXXI are either commercially available or can be prepared from an appropriate heteroaryl halide by well known methods dependent on the nature of such organometallic reagents. Similarly, XXXV is commercially available or can be made by methods well know those so skilled in the art.

Scheme 10 refers to a preparation of a compound of formula VI (VIh), which can be converted to a compound of formula I according to the method of Scheme 1. Referring to Scheme 10, compounds of formula VIh can be prepared by N-arylating a compound of the formula XXXVII with a boronic acid of the formula XXXVI

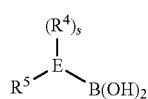

XXXVI in the presence of a suitable Cu(II) catalyst (e.g. Cu(OAc)$_2$), a suitable base and a suitable solvent, or mixture of solvents at a temperature at or above 22° C. Suitable bases include triethylamine, 4-dimethylaminopyridine, pyridine, and cesium carbonate. Suitable solvents include dichloromethane, acetonitrile, chloroform and methanol.

Compounds of formula XXXVII can be prepared by treating a nitrile of formula XXXVIII with sodium azide and a zinc salt (e.g. ZnBr$_2$) with a suitable solvent, or mixture of solvents (e.g. H$_2$O, iPrOH), as demonstrated by Sharpless (*J. Org. Chem.* 2001 66, 7945-7950) to generate 5-substituted tetrazoles.

Compounds of the formula XXXVIII are commercially available or can be made by methods well know those so skilled in the art.

Scheme 11 refers to a preparation of a compound of formula VI (VIi), which can be converted to a compound of formula I according to the method of Scheme 1. Referring to Scheme 11, compounds of formula VIi can be prepared by coupling a compound of the formula XXXX with a boronic acid of the formula XXXIX

XXXIX in the presence of a suitable Cu(II) catalyst (e.g. Cu(OAc)$_2$), a suitable base and a suitable solvent, or mixture of solvents at a temperature at or above 22° C., as described previously for the coupling of XXXVII and XXXVI.

Compounds of formula XXXX can be prepared by coupling a compound of formula XXXXII, wherein Ph is optionally substituted phenyl and ZnI refers to iodo zinc with a compound of formula XXXXI,

XXXXI in the presence of a suitable palladium (0) or nickel (0) catalyst, and a suitable solvent, or mixture of solvents, at a temperature at or above 22° C. Depending on the nature of XXXXII and XXXXI, use of various ligands for palladium (0) or nickel (0) may be needed to affect the aforementioned transformations efficiently. Suitable ligands (e.g. triaryl phosphine ligand, tri(t-butyl)phosphine, 1,1-bis(diphenylphosphanyl)ferrocene (DPPF), 2,2'-bis(diphenylphosphanyl)-1,1'-binaphthyl (BINAP), tri(ortho-tolyl)phosphine, or PHANEPHOS) and/or palladium (0) or nickel (0) complexes include, but is not limited to, tris(dibenzylidene acetone) dipalladium(0) (Pd$_2$(dba)$_3$), di(dibenzylidene acetone) palladium(0) (Pd(dba)$_2$) or palladium acetate (Pd(OAc)$_2$).

Compounds of the formula XXXXII, XXXIX and XXXXI are commercially available or can be made by methods well know those so skilled in the art.

Scheme 12 refers to a preparation of a compound of formula II (IIa-e) by treating a compound of formula III(a-e) with an appropriate alkylating or acylating agent in the presence of a suitable base, such as triethylamine, diisopropylethylamine or pyridine, and a suitable solvent or mixture of solvents, such as dichloromethane, THF or DMF, at a temperature at or above 22° C.

Compounds of formula IIa can be prepared with a suitable alkylating agent (e.g. alkyl halide, dimethylsulfate). Alternatively, a compound of formula IIa can be prepared by a reductive amination using the compounds of formula IIIa with an appropriate aldehyde (e.g. formaldehyde) and an appropriate reducing agent in the presence of a suitable solvent or mixture of solvents at a temperature of about −10° C. to about 40° C., preferably 22° C. Suitable reducing agents include sodium cyanoborohydride, sodium triacetoxyborohydride, and sodium borohydride. Sodium triacetoxyborohydride is preferred. Suitable solvents include methanol, ethanol, dichloroethane, THF, methylene chloride and mixtures thereof, optionally in the presence of an acid or base, such as acetic acid or triethylamine, respectively. Compounds of formula IIIb-e can be prepared with a suitable sulfonating or acylating agent (e.g. $R_7SO_2C_1$, $R_7COCl$, $R_7NCO$ and $R_7OCOCl$ respectively), which are commercially available or can be made by methods well know those so skilled in the art.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The compounds of Formula I that are basic in nature are capable of forming a wide variety of different salts with various inorganic and organic acids. Although such salts must be pharmaceutically acceptable for administration to animals, it is often desirable in practice to initially isolate the compound of Formula I from the reaction mixture as a pharmaceutically unacceptable salt and then simply convert the later back to the free-base compound by treatment with an alkaline reagent and subsequently convert the latter free base to a pharmaceutically acceptable acid addition salt. The acid addition salt of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of Formula I that are acidic in nature are capable of forming base salts with various pharmacologically-acceptable cations. Examples of such salts include the alkali metal or alkaline-earth metal salts and particularly, the sodium and potassium salts. These salts are all prepared by conventional techniques. The chemical bases, which are used as reagents to prepare the pharmaceutically acceptable base salts of this invention, are those which form non-toxic, base salts with the acidic compounds of Formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of reaction and maximum yields of the desired final product.

The compounds of the present invention are modulators of the S1P1 receptor, which is involved in angiogenesis/vasculogenesis, oncogenic and protooncogenic signal transduction and cell cycle regulations. As such, the compounds of the present invention are useful in the prevention and treatment of a variety of human hyperproliferative disorders, such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions, such as benign hyperplasia of the prostate (e.g., BPH). It is, in addition, expected that a compound of the present invention may possess activity against a range of leukemias and lymphoid malignancies.

Further, it is expected that a compound of the present invention may possess activity in diseases or consitions such as autoimmune diseases, rheumatoid arthritis, juvenile arthritis, type I diabetes, lupus, systemic lupus erythematosus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, chronic obstructive pulmonary disease, infection associated with inflammation, viral inflammation, influenza, hepatitis, Guillian-Barre syndrome, chronic bronchitis, xeno-transplantation, transplantation tissue rejection (chronic and acute), organ transplant rejection (chronic and acute), atherosclerosis, restenosis, granulomatous diseases, sarcoidosis, leprosy, scleroderma, ulcerative colitis, Crohn's disease, and Alzheimer's disease.

Further, the present invention may have therapeutic utility in conditions or diseases associated with allergy/respiratory, cardiovascular, diabetes, endocrine care, frailty, obesity, neurodegeneration, dermatology, pain management, urology and sexual health, which may involve the S1P1 receptor that may be mediated by the compounds of this invention.

The activity of the compounds of the invention for the various disorders, diseases or conditions described above can be determined according to one or more of the following assays. All of the compounds of the invention, that were tested, had an inhibition greater than 40% at 9 μM in the S1P1 binding in vitro assay. In addition, all of the compounds of the invention, that were tested, had agonist activity greater than 40% at 9 μM in the GTPγ35S in vitro assay and/or agonist activity greater than 40% at 9 μM in the cAMP in vitro assay. Further, all of the compounds of the invention, that were tested, had and an $ED_{50}$ of less than 100 mg/kg in the in vivo studies mentioned below.

In addition, the compounds of the present invention may be evaluated for differential activity amongst the S1P receptor family members by the GTPγ35S method.

The in vitro activity of the compounds of Formula I and Ia in inhibiting the binding of S1P to the S1P1 receptor may be determined by the following procedure.

S1P1 Binding Assay

S1P1 binding may be measured using the following assay. Twenty microliters of buffer composed of 20 mM HEPES, pH 7.6, 5 mM $MgCl_2$, 1 mM $CaCl_2$, fatty acid free BSA (8 mg/ml) and protease inhibitor cocktail (Boehringer Ingelheim, 63360-92) are added to each well of a Millipore 384-well filter plate.

CHO-S1P1 full-length transfected cells are prepared in ~0.5×10$^5$ cells/well. CHO cells are plated into each well of a 6-well plate in 2 ml of growth media (OptiMEM, Invitrogen). Two micrograms receptor plasmid DNA and 1 ug of chimeric Giq plasmid are mixed in 200 ul OptiMEM, and combined with 6 ul Lipofectamine (2000-9, Invitrogen). The mixture is added drop wise to 2 ml of growth media covering the cells in each well. The cells are allowed to transfect for 8-18 hours at room temperature. The OptiMEM transfection medium is replaced with 2 ml fresh serum-containing medium an incubated for 48 hours. The cells are diluted 1:10 in selection media (OptiMEM, Invitrogen) containing 0.8 mg/ml G418 in 10 cm dishes. Colonies are allowed to form (~1-2 weeks), and 12 colonies from each dish are independently harvested with cloning disks and placed into 24-well plates.

Cell membranes from CHO-S1P1 transfected cells are prepared in the same buffer and are diluted to 12.5 mg/ml (mixed with Polytron for 60 sec.). The cell membranes are then added at a final concentration of 250 μg/well in a total volume of 20 μl per well. The test compounds are dissolved in DMSO to final concentrations of about 9 nm to 0.0005 mM, and 2 μl are added to the buffer and the membranes. Control wells then receive 2 μl of unlabelled sphingosine-1-phosphate while test wells received 20 μl $^{33}$P sphingosine-1-phosphate, final assay concentration of 50 pM. Plates are incubated at room temperature for 1.5 hours, followed by vacuum filtration, washed twice with 20 μl of binding buffer composed of 20 mM HEPES, pH 7.6, 5 mM $MgCl_2$, 1 mM $CaCl_2$, fatty acid free BSA (8 mg/ml), and allowed to air-dry overnight. The bottom of the plate is sealed and then 15 microliters of Perkin Elmer Optiphase Super-mix scintillant is added to each well and allowed to equilibrate. The plate is then read using a Microbeta Trilux. A computerized algorithm gave the concentration of test compound needed to inhibit activity greater than 40% at 9 μM.

GTPγ$^{35}$S Binding Assay

GTPγ$^{35}$S binding assays may be used to evaluate compound mediated S1P receptor agonism. Cell membranes, prepared from 500×10$^5$ CHO cells transfected with S1P1, are dissolved to 11 ml of labeled assay buffer, composed of 20 mM HEPES, pH 7.4, 100 mM NaCl, 10 mM $MgCl_2$, 0.1% fatty acid free BSA, and 5 μM GDP.

To each well of a 96-well flash plate, 50 μl of test compound dissolved in labeled assay buffer, 100 μl of membrane (5×10$^5$ cells/well final concentration), and 50 μl of labeled assay buffer, composed of 6 μl GTPγ$^{35}$S (1000 Ci/mmol), 120 μl 1 mM GDP (200×), 1× assay 5.5 ml are added. The plate is incubated at room temperature for 2 hours and 10 minutes then centrifuged for 20 min @ 1000 g. The plate is read using a Microbeta Trilux. A computerized algorithm gave the concentration of test compound that provided agonist activity greater than 40% at 9 μM.

Whole Cell cAMP Flashplate Assay for Determining Functional Agonism:

The Perkin Elmer [FP]2 cAMPfire assay kit (Catalog #FPA20B040KT) is used to determine agonist potencies for S1P1 in whole cells.

1×cAMP antibody solution and 1×Alexa-Fluor is prepared as described in the cAMPfire assay protocol. The test compounds are dissolved in DMSO and then diluted to final concentrations about 9 nm to 0.0005 mM in the assay buffer, composed of 2 mg/ml FAF-BSA (final 1 mg/ml), 1 mM $CaCl_2$ (0.5 mM final), 5 mM $MgCl_2$ (2.5 mM final) in PBS. Ten microliters of the test compound dilutions are placed into 384-well assay plates. Ten microliters of buffer are placed in control wells. CHO-S1P1 transfected cells (90-100% confluent) are harvested using cell dissociation buffer (GIBCO, 13151-014). The cells are centrifuged, washed with PBS, counted, and resuspended in 1×cAMP antibody solution to achieve a final cell concentration of 3×10$^6$ cells/well. Fifty-five mM of 11× forskolin solution (Sigma #F6886) in assay buffer is prepared. Ten microliters cells in 1×cAMP antibody are added to all applicable wells in 384-well assay plate. Two microliters of 55 μM forskolin (5 μM final in concentration) is added to all applicable wells in 384-well assay plate. Plates are incubated at room temperature for 30 minutes. Twenty microliters of 1× Alexa-Fluor are added to all wells followed by incubation for 60 minutes. Fluorescence polarization is read on Envison, (Perkin Elmer). A computerized algorithm gave the concentration of test compound that provided agonist activity greater than 40% at 9 μM.

The in vivo activity of the compounds of Formula I and Ia for inhibiting the S1P1 receptor may be determined by the following procedure.

Induction of Lymphopenia in Mice

S1P1 is expressed on the surface of T- and B-cells, and is necessary for S1P1/S1P mediated lymphocyte migration from secondary lymphoid tissue for release into peripheral circulation. Agonism of S1P1 results in S1P1 internalization, inhibiting lymphocyte egress into circulation, and is clinically presented as lymphopenia (Chiba, Pharmacology & Therapeutics 2005; 108, 308-319, 2005). The following protocol may be used to assess the potential induction of lymphopenia for the test compounds when administered as a single oral dose to CD1 mice.

A suspension of 5% Gelucire may be used as the vehicle to prepare dosing formulations and to dose vehicle control animals. Test compound is weighed and transferred to a 15 mL Falcon tube or equivalent to make stock formulations. The appropriate amount of 5% Gelucire vehicle is then added to the tube. The resulting formulation is sonicated with a probe sonicator until no obvious particulate matter is apparent. About 500 mL Gelucire (Gattefosse, St-Priest, Cedex, France) is melted in a 1000 W microwave oven set for 3 minutes on high power. The appropriate amount of Gelucire is added to deionized water to form 5% (vol/vol) aqueous Gelucire.

Blood samples (~0.6-0.8 mL) may be collected via intracardiac puncture at appropriate time points. The mice are anesthetized by carbon dioxide and euthanized via exanguination by intracardiac puncture. Blood samples are obtained and placed in tubes containing EDTA. Lymphocytes (L, %) count is measured with Abbott Cell-Dyn 3700 automated analyzer.

Induction of lymphopenia is calculated as a percent of the control count (% T/C), the ratio of the mean lymphocyte counts between treated mice and control mice. Based on the above, the $ED_{50}$ (the dose therapeutically effective in 50 percent of the population) can be determined by standard therapeutic procedures.

Inhibition of Growth Factor Induced Angiogenesis in Mice

The following protocol may be used to assess the potential inhibition of growth factor induced angiogenesis for the test compounds when administered as a single oral dose to CD1 mice.

A suspension of 5% Gelucire may be used as the vehicle to prepare dosing formulations and to dose vehicle control animals. Compound is weighed and transferred to a 15 mL Falcon tube or equivalent to make stock formulations. The appropriate amount of 5% Gelucire vehicle is then added to the tube. The resulting formulation is sonicated with a probe sonicator until no obvious particulate matter is apparent. About 500 mL Gelucire (Gattefosse, St-Priest, Cedex, France) is melted in a 1000 W microwave oven set for 3 minutes on high power. The appropriate amount of Gelucire is added to deionized water to form 5% (vol/vol) aqueous Gelucire.

Sterile porous Gelfrom absorbable gelatin sponges are cut to 3×3 mm pieces and filled with BD Matrigel Matrix (basement membrane preparation without phenol red from BD Bioscience Bedford Mass. #356237) with or without growth factor bFGF (recombinant bFGF 1 µg/plug; R&D Systems, Minneapolis, Minn.) and allowed to equilibrate for 2 hours. The sponges are implanted subcutaneous on the dorsal flank of mice. Animals are treated with the compounds of the present invention after sponge implantation and then once daily for a further 5 days. On the seventh day after implantation, animals are sacrificed, and the vascularized sponges are removed.

The sponge samples are harvested and ground with 200 µL sterile water and centrifuged for 10 minutes at 14,000 RPM. One hundred microliters of sample is removed and placed into a 96-well flat-bottom Falcon plate from BD Bioscience Bedford, Mass. One hundred microliters of TMB substrate (SureBlue TMB Microwell peroxidase substrate, KPL Gaithersburg, Md.) is added to all wells and allowed to incubate for 5 minutes. Fifty microliters of Stop solution ($1NH_2SO_4$) is added to all wells and absorbance is read at 450 nm with 750 nm correction on a VersaMax visible plate reader (Molecular Devices, Sunnyvale, Calif.).

Inhibition of angiogenesis is calculated as a percent of the control absorbance (% T/C), ratio of the mean absorbance between treated mice and control mice. Based on the above, the $ED_{50}$ can be determined by standard therapeutic procedures.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disease, disorder or condition, the rate of administration and the judgment of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-(N-(3,4-dihydro-2-methyl-4-oxoquinazolin-6-ylm-ethyl)-N-methylamino]-2-thenoyl)-L-glutamic acid; growth factor inhibitor; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex (4'-cyano-3-(4-fluorophe-nylsulphonyl)-2-hydroxy-2-methyl-3'-trifluoromethyl)pro-pionanilide). Such conjoint treatment may be achieved by way of simultaneous, sequential or separate dosing of the individual components of the treatment.

The pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like.

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula I may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

Methods of preparing various pharmaceutical compositions with a specific amounts of an active compound are known, or will be apparent to those skilled n this art. For example, see Remington's Pharmaceutical Sciences, Mack Publishing Company, Easter, Pa., 15$^{th}$ Edition (1975).

The examples and preparations provided below further illustrate and exemplify the compounds of the present invention and methods of preparing such compounds. It is to be understood that the scope of the present invention is not limited in any way by the scope of the following examples and preparations.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula I in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The examples and preparations provided below further illustrate and exemplify the compounds of the present invention and methods of preparing such compounds. Alternative routes will be easily discernible to practitioners in the field. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Those molecules with geometric isomers, unless otherwise noted, exist as a mixture of isomers (e.g. cis/trans). Single enantiomers/diastereomers/isomers may be obtained by methods known to those skilled in the art.

General

The following examples are put forth so as to provide those of ordinary skill in the art with a disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient or room temperature (20-25° C.) and pressure is at or near atmospheric. Commercial reagents were utilized without further purification. Conventional flash chromatography was carried out on silica gel (230-400 mesh) and executed under nitrogen or air pressure conditions. Flash chromatography was also carried out using a Combi Flash Chromatography apparatus (Teledyne Isco Tech. Corp.) on silica gel (75-150 uM) in pre-packed cartridges. Particle Beam Mass Spectra were recorded on either a Hewlett Packard 5989®, utilizing chemical ionization (ammonium), or a Fisons (or MicroMass) Atmospheric Pressure Chemical Ionization (APCI) platform which uses a 50/50 mixture of acetonitrile/water. NMR spectra were obtained using a Unity Inova Varian, 400 or 500 MHz, unless otherwise indicated. Chemical shifts are reported in parts per million (ppm) and coupling constants (J) in hertz (Hz). All non-aqueous reactions were run under a nitrogen atmosphere for convenience and to maximize yields. Concentration in vacuo means that a rotary evaporator under reduced pressure was used.

Abbreviations: ethyl acetate (EtOAc), tetrahydrofuran (THF), dimethylformamide (DMF), tetrabutylammonium fluoride (TBAF), 1,1,1-tris(acetyloxy)-1,1-dihydro-1,2-benziodoxol-3-(1H)-one [Dess Martin reagent (periodinane)], methanol (MeOH), ethanol (EtOH), ethyl (Et), acetyl (Ac), methyl (Me), and butyl (Bu).

Detailed analytical and preparative HPLC chromatography methods referred to in the preparations and examples below are outlined as follows:

Analytical HPLC method 1, 2 and 3: Gilson HPLC equipped with a diode array detector and a MetaChem Polaris 5 um C18-A 20×2.0 mm column; peak detection reported usually in total intensity chromatogram and 210 nm wavelength; solvent A: water with 2% acetonitrile and 0.01% formic acid, solvent B: acetonitrile with 0.05% formic acid; flow rate at 1 mL/min.

Method 1 gradient: 5% to 20% solvent B in 1 minute, ramp up to 100% solvent B at 2.25 minutes, stay at 100% B until 2.5 minutes, and back to 5% B at 3.75 minutes.

Method 2 gradient: 5% to 20% solvent B in 1.25 minutes, ramp up to 50% at 2.5 minutes, and up to 100% B at 3.25 minutes, stay at 100% B until 4.25 minutes, and back to 5% B at 4.5 minutes.

Method 3 gradient: stay at 0% solvent B until 1.0 minutes, ramp up to 20% at 2.0 minutes, up to 100% B at 3.5 minutes, back to 0% B at 3.75 minutes.

Analytical HPLC method 4: Hewlett Packard-1050 equipped with a diode array detector and a 150×4 mm Hewlett Packard ODS Hypersil column; peak detection reported at 254 and 300 nm wavelength; solvent A: water with ammonium acetate/acetic acid buffer (0.2 M), solvent B: acetonitrile; flow rate at 3 mL/min.

Method 4 gradient: 0% to 100% B in 10 minutes, hold at 100% B for 1.5 minutes.

Analytical HPLC method 5: Waters 2795 HPLC equipped with a Waters 996 diode array detector, and Sedex 75 evaporative light scattering detector, Waters ZQ mass spectrometer and a Waters Symmetry C8 4.6×50 mm column. Peak detection is usually reported in total intensity chromatogram and 210 nm wavelength; solvent A: water containing 0.01% trifluoroacetic acid, solvent B: acetonitrile containing 0.01% trifluoroacetic acid; flow rate at 2.0 mL/min;

Method 5 gradient: 95% A, 5% B, ramp to 5% A, 95% B in 3.5 minutes, hold at 100% B for 0.5 minutes.

Preparative HPLC method: Shimadzu HPLC equipped with a diode array detector and a Waters Symmetry or Extera C8 column, 19×50 mm or 30×50 mm; peak detection reported usually at 210 nm wavelength; solvent A: water with 2% acetonitrile and 0.1% formic acid, solvent B: acetonitrile with 0.1% formic acid; flow rate between 18 to 40 mL/min. General preparative HPLC gradient methods are usually a linear 0 to 5% B to 100% B over 10 to 25 minutes. Special gradient methods with a narrower gradient window, customized using methods familiar to those skilled in the art, are used for some compounds.

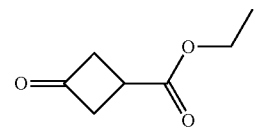

1A. 3-Oxo-cyclobutanecarboxylic acid ethyl ester

A solution of 3-oxo-cyclobutanecarboxylic acid (6.0 g, 52.4 mmol; *J. Org. Chem.* 1988 53, 3841-3843), triethylorthoacetate (28.8 mL, 157 mmol) and toluene (120 mL) was heated at 110° C. for 5 hours. The reaction mixture was cooled to room temperature and quenched with 1.0 N HCl (120 mL). The organic phase was separated, washed with a saturated NaHCO$_3$ and brine, dried (Na$_2$SO$_4$), filtered and concentrated in vacuo to provide the title compound (6.5 g, 80% yield) as an oil.

$^1$H NMR (400 MHz, DMSO-d$_4$) δ 1.23 (t, 3H), 3.30 (m, 5H), 4.14 (q, 2H).

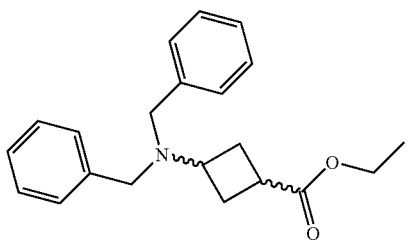

1B. 3-Dibenzylamino-cyclobutanecarboxylic acid ethyl ester

Dibenzyl amine (0.150 g, 0.77 mmol) and sodium triacetoxyborohydride (0.300 g, 1.4 mmol) were added to a solution of 3-oxo-cyclobutanecarboxylic acid ethyl ester (0.100 g, 0.700 mmol) and acetic acid/THF (10%, 4.4 mL), stirred at room temperature for 72 hours and concentrated in vacuo. The resulting residue was dissolved in dichloromethane, washed with water, saturated NaHCO$_3$ and brine, dried (Na$_2$SO$_4$) and concentrated in vacuo to give crude product. Purification by flash chromatography (silica, 1:9-3:7 EtOAc:hexanes) provided the title compound (0.180 g, 73% yield, 10:1 cis:trans ratio) as a solid.

$^1$H NMR (400 MHz, CD$_3$OD) δ 1.22 (t, 3H), 2.08 (m, 2H), 2.20 (m, 2H), 2.70 (m, 1H), 3.11 (m, 1H), 3.50 (s, 4H), 4.09 (q, 2H), 7.30 (m, 10H); ESI-MS: 323 (MH$^+$).

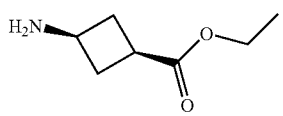

1C. Cis-3-amino-cyclobutanecarboxylic acid ethyl ester, hydrochloride

Pd/C (10% by wt, 0.50 g, 0.30 mmol) was added to a solution of 3-dibenzylamino-cyclobutanecarboxylic acid ethyl ester (1.0 g, 3.09 mmol), ethanol (48.0 mL), water (3.0 mL) and acetic acid (0.20 mL, 3.09 mmol) in a Parr shaker bottle. The reaction mixture was pressurized to 45 psi with H$_2$ and agitated at room temperature for 12 hours. The reaction mixture was filtered and the filtrate was concentrated in vacuo. The resulting residue was taken up in ethanol (2.0 mL) and HCl (2 M in diethyl ether, 0.77 mL) was added. The slurry was filtered to provide a crude solid (0.30 g). The solid was recrystallized from isopropyl alcohol (4.0 mL) to provide the title compound (0.100 g, 45% yield).

$^1$H NMR (400 MHz, CD$_3$OD) δ 1.23 (t, 3H), 2.31 (m, 2H), 2.57 (m, 2H), 3.03 (m, 1H), 4.12 (q, 2H); ESI-MS: 144 (MH$^+$).

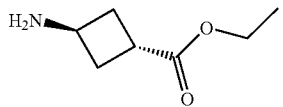

1D. Trans-3-amino-cylcobutanecarboxylic acid ethyl ester, hydrochloride

3-Dibenzylamino-cyclobutanecarboxylic acid ethyl ester (mixture of cis/trans) was loaded on a 2×25 cm Chiralpak AD-H preparatory HPLC column (UV detection @ 210 nM) using a 85:15 (vol:vol) mixture of heptane:ethanol as the mobile phase at a rate of 10 mL/min. The eluent containing the faster-eluting (Rf: 19.74 min) isomer was concentrated in vacuo. The residue was treated with Pd/C by procedures analogous to those described in Preparation 1C for the preparation of cis-3-amino-cylcobutanecarboxylic acid ethyl ester, hydrochloride to provide the title compound.

$^1$H NMR (400 MHz, CD$_3$OD) δ 4.13 (q, J=0.83 Hz, 2H), 3.74-3.68 (m, 1H), 3.04-3.00 (m, 1H), 2.62-2.55 (m, 2H), 2.36-2.29 (m, 2H), 1.24 (t, J=0.83 Hz, 3H); ESI-MS: 144 (MH$^+$).

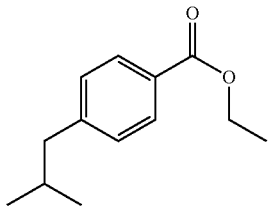

2A. Ethyl 4-isobutylbenzoate

Triethylorthoacetate (15.4 mL, 84.2 mmol) was added slowly to a solution of isobutyl benzoic acid (5.0 g, 28.1 mmol) and toluene (60 mL) at room temperature. The resulting heterogeneous solution was heated to 115° C. and stirred for 24 hours. The reaction mixture was cooled to room temperature and quenched with 1N HCl (60 mL). The organic layer was separated, washed with saturated NaHCO$_3$ (1×30 mL) and brine (1×30 mL), dried (MgSO$_4$), filtered and concentrated in vacuo to obtain the title compound (5.59 g, 97% yield) as a clear oil.

ESI-MS: 207.3 (MH$^+$); HPLC R$_f$: 2.9 minutes (HPLC method 1); HPLC purity: 95%.

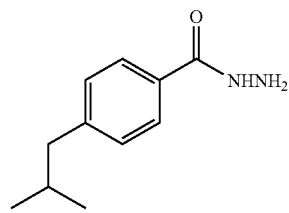

2B. 4-Isobutylbenzohydrazide

Hydrazine monohydrate (2.43 g, 48.5 mmol) was added slowly to a heterogeneous solution of ethyl 4-isobutylbenzoate (5.0 g, 24.2 mmol) and H$_2$O and stirred at reflux for 12 hours. The reaction mixture was cooled to room temperature and filtered. The yellow solid was washed with cold water (1×20 mL) and dried to provide the title compound (3.33 g, 78% yield) as a yellow solid.

ESI-MS: 177.1 (MH$^+$); HPLC R$_f$: 0.8 minutes (HPLC method 1); HPLC purity: 95%.

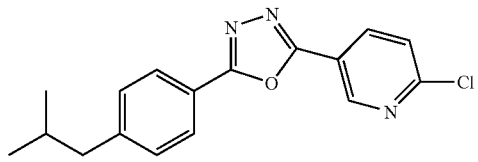

2C. 2-Chloro-5-[5-(4-isobutylphenyl)-1,3,4-oxadiazol-2-yl]pyridine

N,N-Dimethyl(chlorosulphonyl)methaniminium chloride (1.57 g, 0.01 mol) was added to a solution of 6-chloronicotinic acid (1.58 g, 0.01 mol) and dichloromethane (20 mL) at 0° C. and stirred for 10 minutes. 4-isobutylbenzohydrazide (5.29 g, 0.03 mol) was added to the reaction mixture, followed by the dropwise addition of a solution of triethylamine (12.3 mL, 0.09 mol) in dichloromethane (30 mL). The resulting mixture was stirred at room temperature for 12 hours, quenched with water (50 mL) and extracted with dichloromethane (2×50 mL). The combined organic extracts were washed with water (50 mL), dried (Na$_2$SO$_4$) and concentrated in vacuo. The resulting residue was recrystallized from methanol:acetone (10:1) to give the title compound (2.57 g, 82% yield) as a white solid.

ESI-MS: 314.1 (MH$^+$); HPLC R$_f$: 3.4 minutes (HPLC method 1); HPLC purity: 100%.

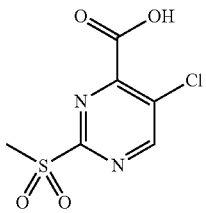

3A.
5-Chloro-2-(methylsulfonyl)pyrimidine-4-carboxylic acid

A stirred mixture of 5-chloro-2-(methylthio)pyrimidine-4-carboxylic acid (8.0 g, 39 mmol) and acetic acid (30 mL) was treated dropwise with 25% aqueous hydrogen peroxide (11.5 mL, 85 mmol) over 1 hour and stirred at room temperature for four days. The reaction mixture was filtered and the solid was washed with cold water (2×50 mL) and dried to afford the title compound (5.8 g, 63% yield) as a white solid.

$^1$H NMR (400 MHz, CDCl$_3$) δ 8.57 (s, 1H), 2.71 (s, 3H).

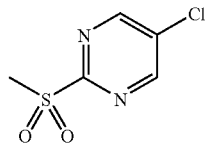

3B. 5-Chloro-2-(methylsulfonyl)pyrimidine

5-Chloro-2-(methylsulfonyl)pyrimidine-4-carboxylic acid (5.7 g, 24 mmol) was refluxed in anisole (8 mL) until the evolution of carbon dioxide ceased. The reaction mixture was cooled to room temperature and filtered. The solid was washed with light petroleum ether (1×50 mL) and dried to obtain the title compound (4.10 g, 88% yield) as a light orange solid.

ESI-MS: 193.5 (MH$^+$); HPLC R$_f$: 1.8 minutes (HPLC method 1); HPLC purity: 100%.

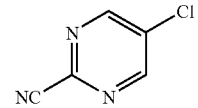

3C. 5-Chloropyrimidine-2-carbonitrile

A solution of 5-chloro-2-(methylsulfonyl)pyrimidine (3.5 g, 18.1 mmol) in dimethyl sulfoxide (10 mL) was treated portion wise at 10° C. over 10 minutes with sodium cyanide (0.9 g, 18.4 mmol). The reaction mixture was stirred for another 10 minutes diluted with cold water (30 mL) and filtered. The solid was washed with cold water (1×30 mL) and dried to obtain (2.05 g, 81% yield) as a pale yellow solid.

ESI-MS: 139 (MH$^+$).

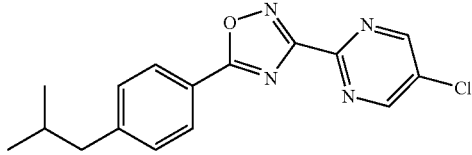

3D. 5-Chloro-2-[5-(4-isobutyl-phenyl)-[1,2,4]oxadiazol-3-yl]-pyrimidine

The title compound was prepared from 5-chloropyrimidine-2-carbonitrile by procedures analogous to those described in Example 4A-4B for the preparation of 2-Chloro-5-[5-(4-isobutylphenyl)-1,2,4-oxadiazol-3-yl]pyridine.

ESI-MS: 315.7 (MH$^+$); HPLC R$_f$: 3.4 minutes (HPLC method 1); HPLC purity: 100%.

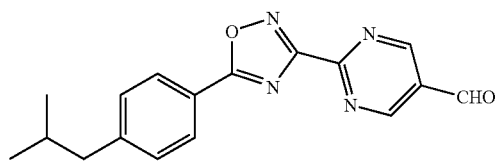

3E. 2-[5-(4-Isobutyl-phenyl)-[1,2,4]oxadiazol-3-yl]-pyrimidine-5-carbaldehyde n-Butyllithium (4.77 mL, 7.16 mmol) was added to a solution of 5-chloro-2-[5-(4-isobutyl-phenyl)-[1,2,4]oxadiazol-3-yl]-pyrimidine (1.5 g, 4.77 mmol) and THF (50 mL) at –78° C. and stirred for 7 hours DMF (3 mL) was added to the reaction mixture, warmed to 0° C. and stirred for 2 hours. The reaction mixture was quenched with saturated aqueous ammonium chloride (15 mL) and stirred at room temperature for 12 hours. The reaction mixture was diluted with EtOAc (25 mL) and the organic layer was separated and washed with water (3×25 mL) and brine (1×25 mL) and concentrated in vacuo to provide the title compound (1.13 g, 76% yield) as an orange solid.

ESI-MS: 309.5 (MH⁺); HPLC R$_f$: 3.0 minutes (HPLC method 1); HPLC purity: 87%.

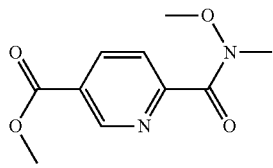

4A. 6-(Methoxy-methyl-carbamoyl)-nicotinic acid methyl ester

A solution of pyridine-2,5-dicarboxylic acid-5-methyl ester (1.0 g, 5.52 mmol), 1,1'-carbonyldiimidazole (0.984 g, 6.07 mmol), 1,2-dichloroethane (30.0 mL) and DMF (8.0 mL) was stirred at room temperature for 1 hour. To the reaction mixture was added N,O-dimethylhydroxylamine hydrochloride (0.535 g, 5.52 mmol) and triethylamine (1.15 mL, 8.28 mmol) and stirred at room temperature for 12 hours. The reaction was diluted with dichloromethane (20.0 mL) and washed with water, 0.5N HCl and saturated NaHCO₃, dried (Na₂SO₄), filtered and concentrated in vacuo to afford the title compound (1.0 g, 81% yield).

¹H NMR (400 MHz, CDCl₃) δ 2.82 (s, 3H), 3.34 (s, 3H), 3.92 (s, 3H), 8.17 (d, 1H), 8.41 (d, 1H), 9.15 (s, 1H).

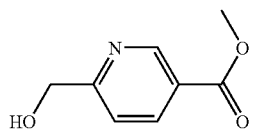

4B. 6-Hydroxymethyl-nicotinic acid methyl ester

Diisobutylaluminum hydride (1.5 M solution in toluene, 9.82 mL) was added dropwise to a solution of 6-(methoxy-methyl-carbamoyl)-nicotinic acid methyl ester (1.1 g, 4.91 mmol) in THF (50 mL) at −78° C. over 10 minutes. The reaction mixture was stirred for 2 hours at −78° C., quenched with 5% HCl/ethanol and warmed to room temperature. The reaction mixture was concentrated in vacuo and the resulting residue was taken up in saturated K₂CO₃ and extracted with ethyl acetate (2×). The combined organic extracts were washed with brine, dried (Na₂SO₄), filtered and concentrated in vacuo. MeOH (15.0 mL) was added to the crude reaction mixture and cooled to 0° C. Sodium borohydride (0.280 g, 7.20 mmol) was added in two portions to the reaction mixture and stirred at 0° C. for 30 minutes. Additional sodium borohydride (0.136 g, 3.6 mmol) was added to the reaction mixture, warmed to room temperature and stirred for 2 hours. The reaction mixture was diluted with dichloromethane (75.0 mL), washed with water and saturated NaHCO₃, dried (Na₂SO₄), filtered and evaporated to yield 6-hydroxymethyl-nicotinic acid methyl ester (0.400 g, 49% yield) as a solid.

¹H NMR (400 MHz, CDCl₃) δ3.94 (s, 3H), 4.81 (s, 2H), 7.34 (d, 1H), 8.29 (d, 2H), 9.14 (s, 1H).

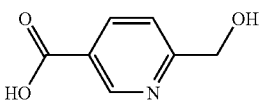

4C. 6-Hydroxymethyl-nicotinic acid

A solution of 6-hydroxymethyl-nicotinic acid methyl ester (0.400 g, 2.38 mmol) in 1.0 N NaOH (25.0 mL) and methanol (10.0 mL) was heated at 80° C. for 1 hour. The reaction mixture was cooled to room temperature and the pH was adjusted to 7.0 with 1.0 N HCl. The reaction mixture was concentrated in vacuo and the resulting salt was slurried in DMF and filtered to provide the title compound.

ESI-MS: 154 (MH⁺).

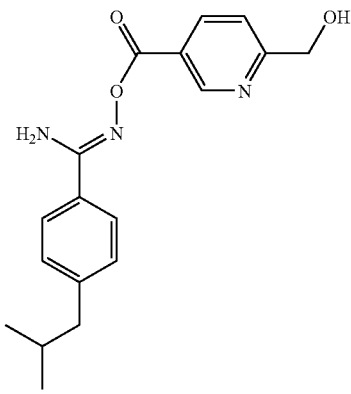

4D. O-(6-Hyroxymethyl-nicotinyl)-N-Hydroxy-4-isobutyl-benzamidine 1,1'-Carbonyldiimidizole (0.385 g, 2.38 mmol) and triethylamine (0.660 mL, 8.94 mmol) was added to a solution of 6-hydroxymethyl-nicotinic acid (0.365 g, 2.38 mmol) and DMF (25.0 mL) and stirred at room temperature for 30 minutes. N-Hydroxy-4-isobutyl-benzamidine (0.457 g, 2.38 mmol) was added to the reaction mixture and stirring continued at room temperature for 12 hours. The reaction mixture was diluted with ethyl acetate (125.0 mL), washed with water, brine, dried (Na₂SO₄), filtered and concentrated in vacuo to yield the title compound (0.052 g, 6.7% yield) as a solid.

¹H NMR (400 MHz, CDCl₃) δ 0.81 (d, 6H), 1.95 (m, 1H), 2.38 (d, 2H), 4.79 (s, 2H), 7.06 (d, 2H), 7.24 (d, 1H), 7.45 (d, 2H), 7.60 (d, 1H), 7.91 (s, 1H).

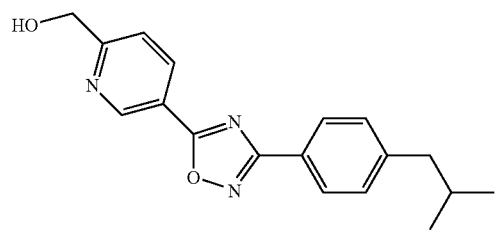

4E. {5-[3-(4-Isobutyl-phenyl)-[1,2,4]oxadiazol-5-yl]-pyridin-2-yl}-methanol

Tetrabutylammonium fluoride (1.0 M in THF, 3.5 mL) was added to a solution of O-(6-hyroxymethyl-nicotinyl)-N-Hydroxy-4-isobutyl-benzamidine (0.778 g, 2.38 mmol) and THF (10.0 mL) and stirred at room temperature for 12 hours. The reaction mixture was diluted with water (50.0 mL) and extracted with dichloromethane. The combined organic layers were washed with brine, dried (Na$_2$SO$_4$), filtered and concentrated in vacuo. Purification by flash chromatography (silica, 1:9-1:1 EtOAc:hexanes) provided the title compound (0.05 g, 6.7% yield) as a solid.

$^1$H NMR (400 MHz, CDCl$_3$) δ 0.91 (d, 6H), 1.90 (m, 1H), 2.54 (d, 2 h), 4.90 (s, 2H), 7.28 (d, 2H), 7.54 (d, 1H), 8.05 (d, 2H), 8.51 (d, 1H), 9.38 (s, 1H); ESI-MS: 310 (MH$^+$).

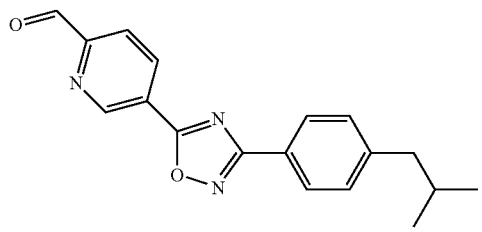

4F. 5-[3-(4-Isobutyl-phenyl)-[1,2,4]oxadiazol-5-yl]-pyridine-2-carbaldehyde

A solution of {5-[5-(4-Isobutyl-phenyl)-[1,2,4]oxadiazol-3-yl]-pyridin-2-yl}-methanol (0.050 g, 0.161 mmol), Dess Martin reagent (0.3 M in CH$_2$Cl$_2$, 0.56 mL, 0.169 mmol) and dichloromethane (0.5 mL) was stirred at room temperature for 30 minutes. Additional Dess Martin reagent (0.3 M in CH$_2$Cl$_2$, 0.28 mL, 0.084 mmol) was added and continued stirring for 30 minutes. The reaction mixture was quenched with 1N NaOH (2.0 mL) and diethyl ether (2.0 mL) and stirred vigorously for 30 minutes. The organic phase was separated, washed with 1.0 N NaOH and brine, dried (Na$_2$SO$_4$), filtered and concentrated in vacuo to yield the title compound (0.060 g) as a crude white solid.

$^1$H NMR (400 MHz, CDCl$_3$) δ 0.90 (d, 6H), 1.92 (m, 1H), 2.54 (d, 2 h), 7.28 (d, 2H), 8.07 (d, 2H), 8.12 (d, 1H), 8.65 (d, 1H), 9.59 (s, 1H) 10.2 (s, 1H); ESI-MS: 308 (MH$^+$).

Preparation 5

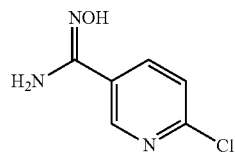

5A. 6-Chloro-N'-hydroxypyridine-3-carboximidamide

Triethylamine (68 mL, 498 mmol) was added to a solution of 6-chloronicotinonitrile (30.0 g, 217 mmol), hydroxylamine hydrochloride (33.0 g, 476 mmol) and ethanol (325 mL) and stirred for 12 hours at 75° C. The reaction mixture was cooled to room temperature, quenched with H$_2$O (400 mL) and the partially concentrated in vacuo. The resulting slurry was filtered and dried to provide the title compound as a crude white solid (37.5 g).

HPLC R$_f$: 2.46 minutes (HPLC method 4); HPLC purity: 100%.

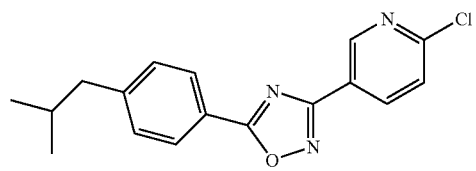

5B. 2-Chloro-5-[5-(4-isobutylphenyl)-1,2,4-oxadiazol-3-yl]pyridine

A solution of 4-isobutylbenzoic acid (19.5 g, 110 mmol), PyBOP (57.6 g, 111 mmol), diisopropylethyl amine (19 mL, 111 mmol) and dichloromethane (1.0 L) was stirred at room temperature for 15 minutes and 6-chloro-N'-hydroxypyridine-3-carboximidamide (19.0 g, 111 mmol) was added. The reaction mixture was stirred at room temperature for 12 hours and filtered. The white solid (35.0 g) was treated with TBAF (1M in THF, 159 mL, 158 mmol) and stirred at room temperature for 12 hours. The reaction mixture was concentrated in vacuo, taken up in H$_2$O (1.0 L) and filtered to provide the title compound (29.6 g, 87% yield) as a white solid.

ESI-MS: 314.2 (MH$^+$); HPLC R$_f$: 3.6 minutes (HPLC method 1); HPLC purity: 100%.

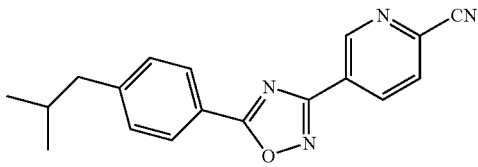

5C. 5-[5-(4-Isobutylphenyl)-1,2,4-oxadiazol-3-yl]pyridine-2-carbonitrile

A solution of 2-chloro-5-[5-(4-isobutylphenyl)-1,2,4-oxadiazol-3-yl]pyridine (5.0 g, 16.0 mmol), zinc cyamide (1.13 g, 9.58 mmol), tetrakis(triphenylphosphine) palladium (0) (0.74 g, 0.64 mmol) and DMF (16 mL) was stirred at 80° C. for 24 hours. The reaction mixture was cooled to room temperature, quenched with H$_2$O (10 mL), and extracted with EtOAc (3×100 mL). The combined organic extracts were washed with H$_2$O (2×100 mL) and brine (2×100 mL), dried (MgSO$_4$), filtered and concentrated in vacuo. Purification by flash chromatography (silica, 2:8 EtOAc:hexanes) provided the title compound (2.87 g, 59% yield) as a solid.

ESI-MS: 305.2 (MH⁺); HPLC $R_f$: 3.2 minutes (HPLC method 1); HPLC purity: 100%.

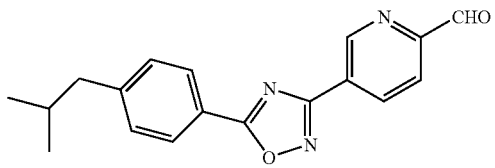

5D. 5-[5-(4-Isobutylphenyl)-1,2,4-oxadiazol-3-yl]pyridine-2-carbaldehyde

Diisobutylaluminum hydride (1.5 M solution in toluene, 6.36 mL) was added dropwise to a cold (−78° C.) solution of 5-[5-(4-isobutylphenyl)-1,2,4-oxadiazol-3-yl]pyridine-2-carbonitrile (2.87 g, 9.44 mmol) in CH₂Cl₂ (60 mL) and stirred for 3 hours at −78° C., with additional diisobutylaluminum hydride (1.5 M solution in toluene, 2×1.57 mL) added at 0.5 hours and 1 hour. The reaction mixture was quenched at −78° C. with 1N HCl (20 mL), warmed to room temperature and stirred for 1.5 hours. The organic layer was separated and the aqueous phase was basified with solid NaHCO₃ (pH=12), filtered and extracted with CH₂Cl₂ (3×100 mL). The combined organic layers were washed with brine, dried (Na₂SO₄), filtered and concentrated in vacuo to provide the title compound (2.79 g, 95% yield) as an orange solid.

ESI-MS: 308.2 (MH⁺); HPLC $R_f$: 9.34 minutes (HPLC method 4); HPLC purity: 95%.

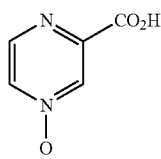

6A. 4-Oxy-pyrazine-2-carboxylic acid

Water (35 mL) was added to a solution of hydrogen peroxide (30% wt. in H₂O, 9.14 mL, 80.6 mmol) and NaW₂Ox2H₂O (0.67 g, 2.0 mmol) and the reaction mixture was adjusted to a pH=2 with sulfuric acid (diluted with 15 mL H₂O). Pyrazine-2-carboxylic acid (10.0 g, 80.6 mmol) was added to the reaction mixture, stirred for 2 hours at 80° C. and 12 hours at room temperature. The reaction slurry was filtered, washed with cold H₂O (35 mL) and dried to give the title compound (8.3 g, 75%) as a white solid.

¹H NMR (400 MHz, DMSO-d₄) δ 14.0 (br. s, 1H), 8.61-8.59 (m, 2H), 8.48 (dd, J=4.0, 1.9 Hz, 1H).

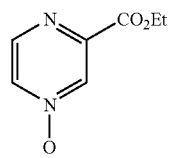

6B. 4-Oxy-pyrazine-2-carboxylic acid ethyl ester

HCl gas was bubbled through a solution of 4-oxy-pyrazine-2-carboxylic acid (20.0 g, 143 mmol) and EtOH (300 mL) for 30 minutes and stirred at 80° C. for 2 hours. The reaction mixture was cooled to room temperature, stirred for 2 hours and filtered to give the title compound (15.0 g, 63%) as a brown solid.

HPLC $R_f$: 2.45 minutes (HPLC method 4); HPLC purity: 98%.

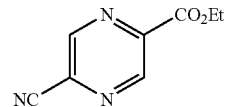

6C. 5-Cyano-pyrazine-2-carboxylic acid ethyl ester

A mixture of 4-oxy-pyrazine-2-carboxylic acid ethyl ester (1.0 g, 5.95 mmol), triethylamine (4.06 mL, 29.8 mmol) and acetonitrile (40 mL) was stirred for 5 minutes and diethyl cyanophosphonate (3.15 mL, 20.8 mmol) was slowly added. The reaction mixture was stirred at 80° C. for 18 hours in a sealed tube, cooled to room temperature and concentrated in vacuo. The resulting residue was re-dissolved in EtOH (10 mL), stirred for 3 hours and concentrated in vacuo. Purification by flash chromatography (silica, 1:9 EtOAc:hexanes) provided the title compound (0.65 g, 63%) as a yellow solid.

HPLC $R_f$: 1.0 minute (HPLC method 1); HPLC purity: 100%.

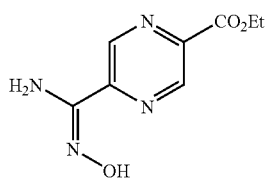

6D. Ethyl 5-[amino(hydroxyimino)methyl]pyrazine-2-carboxylate

Triethylamine (7.08 mL, 51.9 mmol) was added to a solution of 5-cyano-pyrazine-2-carboxylic acid ethyl ester (4.0 g, 22.6 mmol), hydroxylamine hydrochloride (3.45 g, 49.7 mmol) and EtOH (32 mL) and stirred at 80° C. for 12 hours. The reaction mixture was cooled to room temperature, concentrated in vacuo and dissolved in H₂O (30 mL). The aqueous solution was extracted with CHCl₃ (3×30 mL) and the combined organic extracts were dried (Na₂SO₄), filtered and concentrated in vacuo to yield the title compound (2.95 g, 62%) as a yellow solid.

ESI-MS: 211.3 (MH⁺); HPLC $R_f$: 3.28 minutes (HPLC method 4); HPLC purity: 100%.

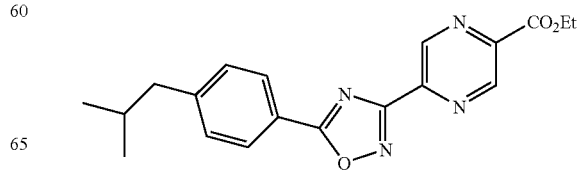

6E. Ethyl 5-[5-(4-isobutylphenyl)-1,2,4-oxadiazol-3-yl]pyrazine-2-carboxylate A mixture of 4-isobutylbenzoic acid (0.28 g, 1.59 mmol), 1-hydroxybenzotriazole (0.042 g, 0.31 mmol), N-[(1H-1,2,3-benzotriazol-1-yloxy)(dimethylamino)methylene]-N-methylmethanaminium tetrafluoroborate (0.51 g, 1.59 mmol), diisopropylethylamine (1.4 mL, 7.86 mmol) and dioxane (4 mL) was stirred at room temperature for 1 hour. Ethyl 5-[amino(hydroxyimino)methyl]pyrazine-2-carboxylate (0.33 g, 1.57 mmol) was added to the reaction mixture, stirred for 1.5 hours at room temperature and 6 hours at 100° C. The reaction mixture was cooled to room temperature, quenched with H$_2$O (10 mL) and filtered. The precipitate was dissolved in EtOAc (10 mL), washed with 1N NaOH (3×10 mL) and brine (2×10 mL), dried (Na$_2$SO$_4$), filtered and concentrated in vacuo to yield the title compound (0.15 g, 27%) as a white solid.

ESI-MS: 353.2 (MH$^+$); HPLC R$_f$: 8.76 minutes (HPLC method 4); HPLC purity: 100%.

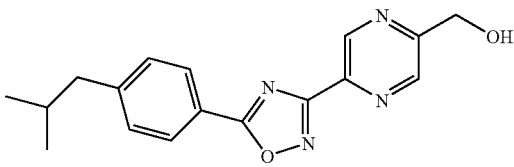

6F. {5-[5-(4-Isobutylphenyl)-1,2,4-oxadiazol-3-yl]pyrazin-2-yl}methanol

Diisobutylaluminum hydride (1.5 M solution in toluene, 2.12 mL) was added dropwise to a cold (−78° C.) solution of ethyl 5-[5-(4-isobutylphenyl)-1,2,4-oxadiazol-3-yl]pyrazine-2-carboxylate (0.51 g, 1.45 mmol) in toluene (10 mL) and stirred for 0.5 hours at −78° C. The reaction mixture was warmed to 0° C., quenched with 1N HCl (10 mL) and extracted with EtOAc (3×10 mL). The combined organic extracts were dried (Na$_2$SO$_4$), filtered and concentrated in vacuo to provide the title compound (0.50 g) as a crude orange oil.

ESI-MS: 311.4 (MH$^+$); HPLC R$_f$: 2.7 minutes (HPLC method 1); HPLC purity: 100%.

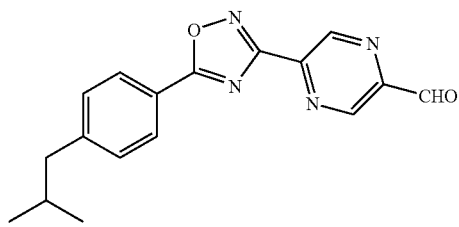

6G. 5-[5-(4-Isobutylphenyl)-1,2,4-oxadiazol-3-yl]pyrazine-2-carbaldehyde

The title compound was prepared from {5-[5-(4-isobutylphenyl)-1,2,4-oxadiazol-3-yl]pyrazin-2-yl}methanol by procedures analogous to those described in Preparation 4F for the preparation of 5-[3-(4-isobutyl-phenyl)-[1,2,4]oxadiazol-5-yl]-pyridine-2-carbaldehyde.

ESI-MS: 310.3 (MH$^+$); HPLC R$_f$: 2.8 minutes (HPLC method 1); HPLC purity: 100%.

Preparation 7

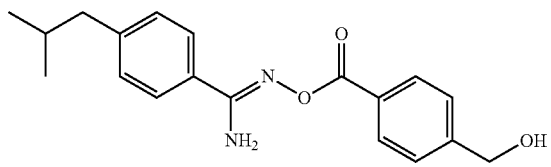

7A: N'-{[4-(Hydroxymethyl)benzoyl]oxy}-4-isobutylbenzenecarboximidamide 1,1'-Carbonyldiimidazole (2.37 g, 14.6 mmol) was added to a solution of 4-hydroxymethylbenzoic acid (2.00 g, 13.1 mmol) and DMF (50 mL) and stirred at room temperature for 1 hour. N'-Hydroxy-4-isobutylbenzamidine (2.54 g, 13.2 mmol) was added and stirred for 16 hours. The reaction mixture was diluted with water, causing a white solid to precipitate, filtered, washed with water, and dried to give the title compound (3.08 g, 72% yield) as a crude white solid.

ESI-MS: 327 (MH$^+$); HPLC R$_f$: 2.8 min. (HPLC method 5).

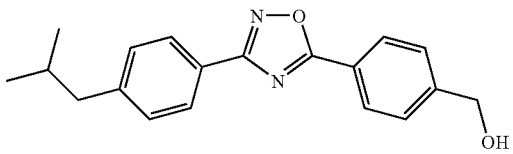

7B: {4-[3-(4-Isobutylphenyl)-1,2,4-oxadiazol-5-yl]phenyl}methanol

Tetrabutylammonium fluoride (1.0 M solution in THF, 10 mL) was added to a solution of N'-{[4-(hydroxymethyl)benzoyl]oxy}-4-isobutylbenzenecarboximidamide (3.07 g, 9.42 mmol) and THF (50 mL) and stirred at room temperature for 20 hours. The reaction mixture was diluted with ethyl acetate, washed with water and brine, dried over Na$_2$SO$_4$, filtered and concentrated in vacuo to give the title compound (1.33 g, 46% yield) as a crude solid.

$^1$H NMR (400 MHz, CDCl$_3$) δ 0.92 (m, 6H), 1.89 (m, 1H), 2.35 (m, 2H), 2.53 (m, 2H), 4.81 (s, 2H), 7.28 (d, 2H), 7.61 (m, 2H), 8.06 (d, 2H), 8.20 (d, 2H).

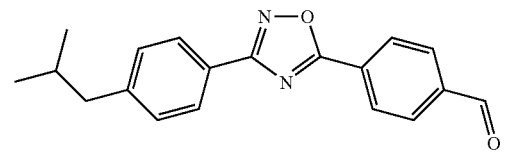

7C: 4-[3-(4-Isobutylphenyl)-1,2,4-oxadiazol-5-yl]benzaldehyde

A solution of {4-[3-(4-isobutylphenyl)-1,2,4-oxadiazol-5-yl]phenyl}methanol (1.30 g, 4.21 mmol) and dichloromethane (20 mL) was added to a solution of Dess-Martin periodinane (2.25 g, 5.30 mmol) and dichloromethane (20 mL) and stirred at room temperature for 2 hours. The reaction mixture was diluted with dichloromethene, washed with 1 N NaOH (2×) and brine, dried over $Na_2SO_4$, filtered and concentrated in vacuo to give the title compound (0.333 g, 26% yield) as a white solid.

$^1$H NMR (400 MHz, $CDCl_3$) δ 0.92 (d, 6H), 1.91 (m, 1H), 2.55 (d, 2H), 7.29 (d, 2H), 8.06 (m, 4H), 8.39 (d, 2H).

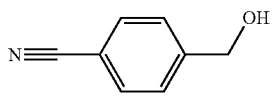

8A. 4-Hydroxymethyl-benzonitrile

Boron trifluoride diethyl etherate (0.85 mL, 6.8 mmol) was added to a solution of 4-cyanobenzoic acid (1.0 g, 6.8 mmol) and THF (10 mL). At room temperature, borane-tetrahydrofuran complex (1.0 M, 13.6 mL) was added to the reaction mixture drop-wise with no observed exotherm. The reaction mixture was stirred at room temperature for 2 hours and concentrated in vacuo. The resulting residue was taken up in ethyl acetate (50 mL), washed with saturated $NaHCO_3$ and brine, dried ($Na_2SO_4$), filtered and concentrated in vacuo to give the title compound (0.900 g, 95% yield) as a solid.

$^1$H NMR (400 MHz, $CDCl_3$) δ 4.65 (s, 2H), 7.38 (d, 2H), 7.53 (d, 2H).

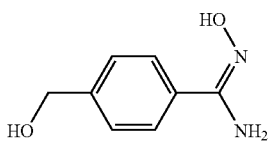

8B. N-Hydroxy-4-hydroxymethyl-benzamidine

Hydroxylamine hydrochloride (5.17 g, 75.0 mmol) and sodium bicarbonate (12.6 g, 150 mmol) were added to a solution of 4-hydroxymethyl-benzonitrile (5.0 g, 37.5 mmol) and methanol (65.0 mL). The reaction was heated to reflux for 12 hours. The reaction mixture was cooled to room temperature and the resulting slurry was filtered. The filtrate was concentrated in vacuo to give of the title compound (6.0 g, 48% yield) as an oily solid.

$^1$H NMR (400 MHz, $CD_3OD$) δ 4.60 (s, 2H), 7.36 (d, 2H), 7.59 (d, 2H).

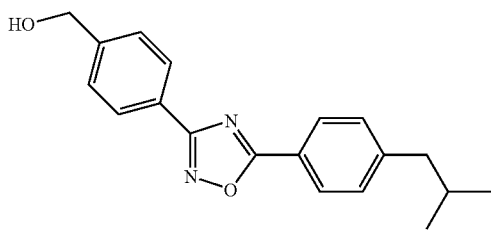

8C. {4-[5-(4-Isobutyl-phenyl)-[1,2,4]oxadiazol-3-yl]-phenyl}-methanol

A solution of 4-isobutyl-benzoic acid (451 mg, 2.53 mmol) and 1,1'-carbonyldiimidazole (491 mg, 3.03 mmol) in DMF (10 mL) was stirred at room temperature for 2 hours. N-hydroxy-4-hydroxymethyl-benzamidine (420 mg, 2.53 mmol) was added to the reaction mixture, stirred at room temperature for 18 hours and diluted with ethyl acetate. The reaction mixture was washed with aqueous sodium hydroxide (0.25 N), water and brine, dried ($MgSO_4$), filtered and concentrated in vacuo. The resulting residue was treated with a solution of tetrabutylammonium fluoride (1.0 M in THF, 2.78 mL) and THF (6 mL) and stirred at room temperature for 12 hours. The reaction mixture was quenched with brine and extracted with ethyl acetate. The combined organic layers were concentrated in vacuo. Purification by flash chromatography (silica, 1:9 to 2:3 EtOAc:hexanes) provided the title compound (193 mg, 29% yield) as a solid.

$^1$H NMR (400 MHz, $CDCl_3$) δ0.91 (d, 6H), 1.91 (m, 1H), 2.55 (d, 2H), 4.77 (s, 2H), 7.30 (d, 2H), 7.49 (d, 2H), 8.11 (d, 2H), 8.14 (d, 2H); ESI-MS: 309 ($MH^+$).

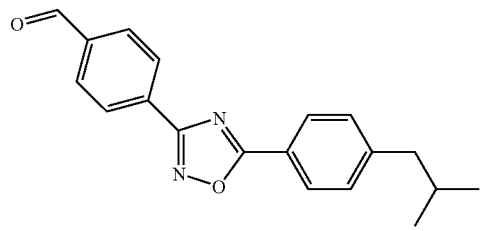

8D. 4-[5-(4-Isobutyl-phenyl)-[1,2,4]oxadiazol-3-yl]-benzaldehyde

A solution of methylene chloride (10.4 mL) was cooled to −78° C. To this was added dimethyl sulfoxide (416 uL) and oxalyl chloride (340 uL) and the solution was stirred for 5 minutes. {4-[5-(4-Isobutyl-phenyl)-[1,2,4]oxadiazol-3-yl]-phenyl}-methanol (574 mg, 1.86 mmol) and diisopropyl ethyl amine (2.7 mL) were added to the reaction mixture and stirred at −78° C. for 30 minutes. The reaction mixture was warmed to room temperature, concentrated in vacuo and diluted with ethyl acetate. The mixture was washed with 1N HCl, saturated aqueous sodium bicarbonate and brine. The organic layer was dried ($MgSO_4$), filtered and concentrated in vacuo to provide a crude residue. This residue was slurried in hexanes (10 mL) and heated to reflux. The solution was allowed to cool to ambient temperature and the resulting slurry was stirred for 1 hour and filtered. The solid was washed with minimal cold hexanes and dried in vacuo to give the title compound (183 mg, 32% yield) as a solid.

¹H NMR (400 MHz, CDCl₃) δ 0.90 (d, 6H), 1.91 (m, 1H), 2.56 (d, 2H), 7.32 (d, 2H), 8.00 (d, 2H), 8.12 (d, 2H), 8.34 (d, 2H), 10.1 (s, 1H); ESI-MS: 307.4 (MH⁺).

Preparation 9

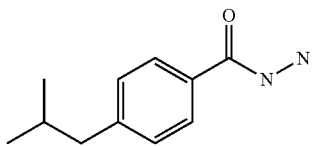

9A: 4-Isobutylbenzohydrazide

A solution isobutylbenzoic acid (2.00 g, 11.2 mmol) in DMF (10 ml) was treated with HBTU (4.25 g, 11.2 mmol), diisopropylethylamine (7.24 g, 56.0 mmol), then hydrazine (1.80 g, 56.0 mmol) and stirred at room temperature for 12 hours. The reaction was diluted with ethyl acetate (150 mL), washed with 5% NaHCO₃ (aq.) and brine, dried (MgSO₄), filtered and concentrated in vacuo to give the title compound (2.10 g, 91%) as a white solid.

ESI-MS: 193 (MH⁺).

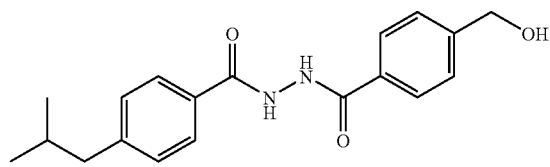

9B: 4-(Hydroxymethyl)-N'-(4-isobutylbenzoyl)benzohydrazide

4-Isobutylbenzohydrazide (2.10 g, 10.9 mmol) was added to a stirred solution of 4-hydroxymethylbenzoic acid (1.66 g, 11.2 mmol), HBTU (4.25 g, 11.2 mmol), diisopropylethylamine (1.45 g, 11.2 mmol) and DMF (50 mL) and stirred at room temperature for 12 hours. The reaction was diluted with ethyl acetate (200 mL), washed with 5% NaHCO₃ (aq.) and brine, dried (MgSO₄), filtered and concentrated in vacuo to give a white solid. The solid was triturated with ethyl acetate and filtered to give the title compound (2.01 g, 56% yield).

¹H NMR (400 MHz, CDCl₃) δ 0.78 (d, 6H), 1.77 (m, 1H), 2.42 (d, 2H), 4.58 (s, 2H), 7.13 (d, 2H), 7.33 (d, 2H), 7.70 (d, 2H), 7.76 (d, 2H); ESI-MS: 327 (MH⁺).

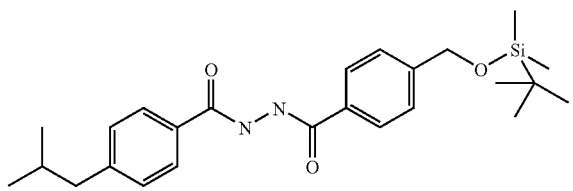

9C: 4-(tert-Butyl-dimethyl-silanyloxymethyl)-benzoic acid N'-(4-isobutyl-benzoyl)-hydrazide t-Butyldimethylsilyl chloride (0.220 g, 1.33 mmol) was added to a stirred solution of 4-(hydroxymethyl)-N'-(4-isobutylbenzoyl)benzohydrazide (0.326 g, 1.16 mmol) and imidazole (0.090 g, 1.33 mmol) and DMF (5 mL) and stirred at room temperature for 72 hours. The reaction mixture was diluted with ethyl acetate, washed with water and concentrated in vacuo to yield a white solid. The solid was triturated with ethyl acetate to give the title compound (0.50 g, 97% yield) as a white solid.

¹H NMR (400 MHz, CDCl₃) δ 0.10 (s, 6H), 0.78 (d, 6H), 0.95 (s, 9H), 1.77 (m, 1H), 2.51 (d, 2H), 4.78 (s, 2H), 7.16 (s, 1H), 7.25 (d, 2H), 7.43 (d, 2H), 7.73 (s, 1H), 7.81 (d, 2H), 7.87 (d, 2H); ESI-MS: 441 (MH⁺).

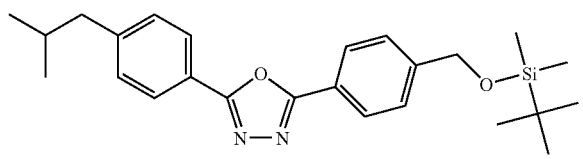

9D: 2-[4-({[tert-Butyl(dimethyl)silyl]oxy}methyl) phenyl]-5-(4-isobutylphenyl)-1,3,4-oxadiazole 4-(tert-Butyl-dimethyl-silanyloxymethyl)-benzoic acid N'-(4-isobutyl-benzoyl)-hydrazide (0.513 g, 1.16 mmol) was added to a solution of (methoxycarbonylsulfamoyl)triethylammonium hydroxide (1.39 g, 5.82 mmol), DMF (2 mL) and THF (23 mL) and stirred at 110° C. for 16 hours in a sealed vial. The reaction mixture was diluted with dichloromethane (100 mL), washed with water (3×), dried (Na₂SO₄), filtered and concentrated in vacuo to give the title compound (0.50 g, 100% yield) as a crude white solid.

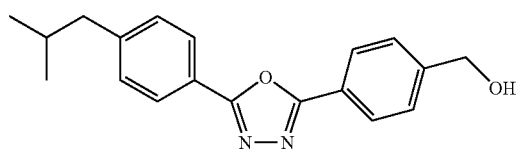

9E: {4-[5-(4-Isobutylphenyl)-1,3,4-oxadiazol-2-yl] phenyl}methanol

Tetrabutylammonium fluoride (1.0 M in THF, 2.0 mL) was added to a solution of 2-[4-({[tert-butyl(dimethyl)silyl] oxy}methyl)phenyl]-5-(4-isobutylphenyl)-1,3,4-oxadiazole (0.50 g, 1.18 mmol) and THF (10 mL) and stirred at room temperature for 16 hours. The reaction mixture was diluted with ethyl acetate (100 mL), washed with water and brine, dried (Na₂SO₄,), filtered and concentrated in vacuo to give the title compound (0.322 g, 88% yield) as a white solid.

¹H NMR (400 MHz, CDCl₃) δ 0.94 (d, 6H), 1.93 (m, 2H), 2.60 (d, 2H), 4.85 (d, 2H), 7.35 (2, 2H), 7.58 (d, 2H), 8.08 (d, 2H), 8.17 (d, 2H).

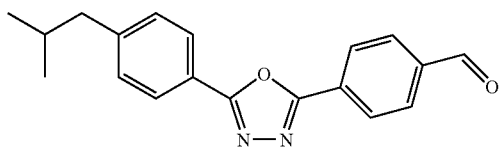

9F: 4-[5-(4-Isobutylphenyl)-1,3,4-oxadiazol-2-yl]benzaldehyde

Dess-Martin periodinane (0.576 g, 21.4 mmol) was added to a solution of {4-[5-(4-isobutylphenyl)-1,3,4-oxadiazol-2-yl]phenyl}methanol (0.322 g, 1.04 mmol) and dichloromethane (10 mL) and stirred at room temperature for 1 hour. The reaction mixture was quenched with 1M NaOH (10 mL), stirred for 15 minutes then additional 1N NaOH (5 mL) was added. The layers were separated and the aqueous phase was extracted with ethyl acetate (3×). The combined organic layers were washed with brine, dried over $Na_2SO_4$, filtered and concentrated in vacuo to give the title compound (0.322 g, 88% yield) as a white solid.

$^1$H NMR (400 MHz, $CDCl_3$) δ 0.91 (d, 6H), 1.91 (m, 1H), 2.56 (d, 2H), 7.32 (d, 2H), 8.06 (m, 4H), 8.32 (d, 2H), 10.1 (s, 1H).

Preparation 10

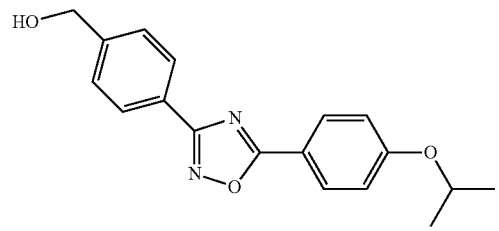

10A: 4-[5-(4-Isopropoxy-phenyl)-[1,2,4]oxadiazol-3-yl]-phenylmethanol

A solution of 4-iso-propoxybenzoic acid (2.0 g, 11.1 mmol), 1-(3-dimethylaminopropyl)-3-ethylcarbodiimide hydrochloride (2.13 g, 11 mmol), 1-hydroxybenzotriazole hydrate (1.50 g, 11.1 mmol) and DMF (14 mL) was stirred at room temperature for 30 minutes. N-hydroxyl-4-(hydroxylmethyl)benzamidine (1.84 g, 11.1 mmol) was added to the reaction mixture and stirred at 140° C. for 2 hours. The reaction mixture was cooled to room temperature, quenched with water (20 mL) and the aqueous layer was extracted with EtOAc (100 mL). The combined organic layers were washed with 1N HCl and sat. $NaHCO_3$, dried ($Na_2SO_4$), filtered and concentrated in vacuo to provide the title compound (2.0 g, 58% yield) as a pale yellow solid.

$^1$H NMR (400 MHz, $CD_3OD$) δ 1.35 (d, 6H), 4.67 (s, 2H), 4.73 (m, 1H), 7.09 (d, 2H), 8.10 (m, 4H); ESI-MS: 310 ($MH^+$).

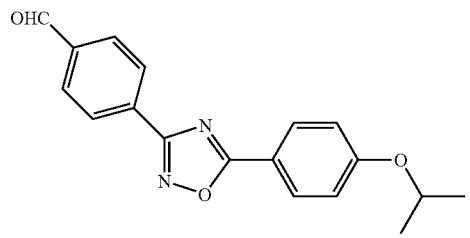

10B. 4-[5-(4-isopropoxy-phenyl)-1,2,4-oxadiazol-3-yl]benzaldehyde

The title compound was prepared from 4-[5-(4-isopropoxy-phenyl)-[1,2,4]oxadiazol-3-yl]-phenylmethanol by procedures analogous to those described in Preparation 4F for the preparation of 5-[3-(4-isobutyl-phenyl)-[1,2,4]oxadiazol-5-yl]-pyridine-2-carbaldehyde.

Preparation 11

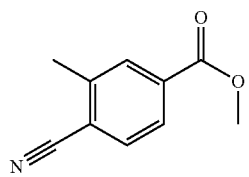

11A: 4-Cyano-3-methyl-benzoic acid methyl ester

Zinc cyamide (6.2 g, 52 mmol) and tetrakis(triphenylphosphine) palladium (0) (4 g, 3 mmol) was added to a solution of 4-bromo-3-methyl-benzoic acid methyl ester (20 g, 87 mmol) and DMF (100 mL) and stirred for 4 hours at 120° C. The reaction mixture was cooled to room temperature, diluted with EtOAc (700 mL), washed with water and brine, dried ($Na_2SO_4$), filtered and concentrated in vacuo. Purification by flash chromatography (silica, 1:3 EtOAc:hexanes) provided the title compound (12.3 g, 39.8% yield) as a solid.

$^1$H NMR (400 MHz, $CDCl_3$) δ 2.59 (s, 3H), 3.93 (s, 3H), 7.66 (d, 1H), 7.90 (d, 1H), 7.97 (d, 1H).

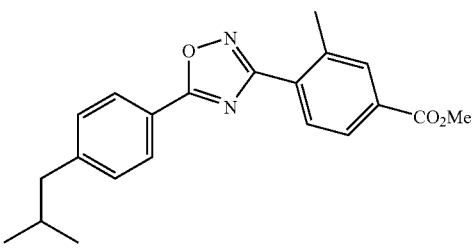

11B: 4-[5-(4-Isobutyl-phenyl)-[1,2,4]oxadiazol-3-yl]-3-methyl-benzoic acid methyl ester The title compound was prepared from 4-cyano-3-methyl-benzoic acid methyl ester and 4-isobutyl-benzoic acid by procedures analogous to those described in Preparations 8B and 10A for the preparation of N-hydroxy-4-hydroxymethyl-benzamidine and 4-[5-(4-isopropoxy-phenyl)-[1,2,4]oxadiazol-3-yl]-phenylmethanol, respectively.

$^1$H NMR (400 MHz, CDCl$_3$) δ 0.92 (d, 6H), 1.93 (m, 1H), 2.57 (d, 2H), 2.72 (s, 3H), 3.94 (s, 3H), 7.32 (d, 2H), 7.97 (t, 2H), 8.14 (m, 3H).

Preparation 12

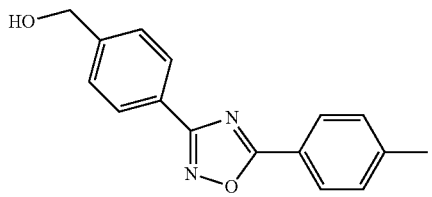

12A. {4-[5-(4-Methylphenyl)-1,2,4-oxadiazol-3-yl]phenyl}methanol

The title compound was prepared from 4-methylbenzoic acid by procedures analogous to those described in Preparations (8A-8C) for the preparation of {4-[5-(4-isobutyl-phenyl)-[1,2,4]oxadiazol-3-yl]-phenyl}-methanol.

ESI-MS: 267.3 (MH$^+$); HPLC R$_f$: 2.71 minutes (HPLC method 1); HPLC purity: >90%.

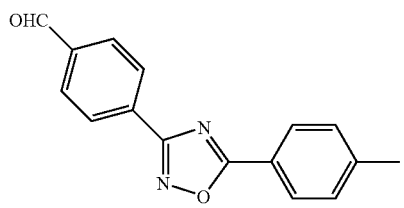

12B. 4-[5-(4-Methylphenyl)-1,2,4-oxadiazol-3-yl]benzaldehyde

Florosil (250 mg) and PCC (121.5 mg, 0.564 mmol) was added to a solution of {4-[5-(4-methylphenyl)-1,2,4-oxadiazol-3-yl]phenyl}methanol (75.1 mg, 0.282 mmol) and CH$_2$Cl$_2$ (1.5 mL) and stirred at room temperature for 3 hours. The reaction mixture was diluted with CH$_2$Cl$_2$ and filtered through a pad of silica gel. The pad was eluted with CH$_2$Cl$_2$ and 1:1 ethyl acetate:hexanes and the combined eluents were concentrated in vacuo to provide the title compound as a crude residue.

ESI-MS: 265.1 (MH$^+$); HPLC R$_f$: 3.11 minutes (HPLC method 1); HPLC purity: >90%.

Preparation 13

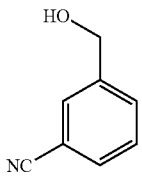

13A. 3-(hydroxymethyl)benzonitrile

3-Cyanobenzoic acid (5 g, 34.0 mmol) was dissolved in THF (50 mL) at ambient temperature. To this solution was added borane/THF complex (1M in THF, 68 mL, 68.0 mmol) in three portions and borane trifluoride/diethyl etherate complex (4.3 mL, 34.0 mmol). The reaction mixture was stirred at ambient temperature for 2 hours, quenched with methanol and stirred for 10 minutes. The solution was diluted with ethyl acetate and washed with saturated NaHCO$_3$ (3×). The organic layer was separated, dried (MgSO$_4$), filtered and concentrated in vacuo to give the title compound (2.19 g, 48% yield) as a solid.

H NMR (400 MHz, CD$_3$OD) ▢▢ ▢ (s, 2H), 7.48 (t, 1H), 7.58 (d, 1H), 7.61 (d, 1H), 7.67 (s, 1H)

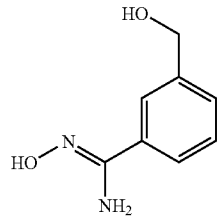

13B. N'-Hydroxy-3-(hydroxymethyl)benzenecarboximidamide

Hydroxyl amine hydrochloride (2.29 g, 32.9 mmol) and sodium bicarbonate (5.52 g, 65.8 mmol) were added to 3-(hydroxymethyl)benzonitrile (2.19 g, 16.4 mmol) and methanol (30 mL) and stirred at reflux for 18 hours. The reaction mixture was cooled to ambient temperature and filtered. The filtrate was concentrated in vacuo to give the title compound (2.88 g, 100% yield) as a solid.

ESI-MS: 167.1 (MH$^+$)

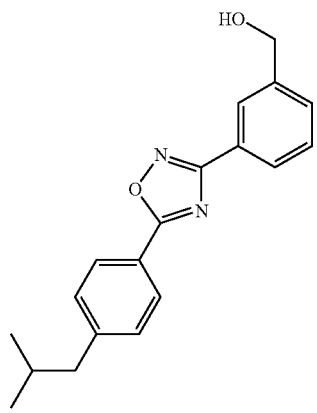

13C. {3-[5-(4-isobutylphenyl)-1,2,4-oxadiazol-3-yl]phenyl}methanol

Carbonyl diimidazole (421 mg, 2.60 mmol) was added to a solution of 4-isobutyl benzoic acid (386 mg, 2.17 mmol) and DMF (10 mL) and stirred for 2 hours at room temperature. N'-hydroxy-3-(hydroxymethyl)benzenecarboximidamide (360 mg, 2.17 mmol) was added to the reaction mixture and stirred for 18 hours at ambient temperature. The reaction was diluted with water and extracted with ethyl acetate (2×) and the combined organic extracts were washed with 0.25 N sodium hydroxide, water and brine. The organic layer was dried (MgSO$_4$), filtered and concentrated in vacuo to give a crude residue. The crude residue was dissolved in THF (6 mL) and treated with tetrabutyl ammonium fluoride (1M in THF, 2.4 mL, 2.38 mmol). The solution was stirred at ambient temperature for 18 hours, diluted with brine and extracted with ethyl acetate. The combined organic layers were concentrated in vacuo. Purification by flash chromatography (silica, 1:9 to 2:3 EtOAc:hexanes) provided the title compound (193 mg, 29% yield) as a solid.

ESI-MS: 309.2 (MH$^+$)

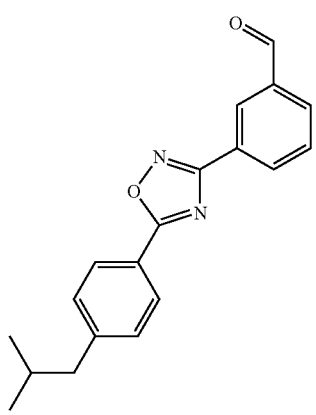

13D. 3-[5-(4-isobutylphenyl)-1,2,4-oxadiazol-3-yl]benzaldehyde

Florosil (400 mg) and pyridinium chlorochromate (195 mg, 0.903 mmol) were added to a solution of {3-[5-(4-isobutylphenyl)-1,2,4-oxadiazol-3-yl]phenyl}methanol (139 mg, 0.451 mmol) and methylene chloride (2.5 mL) and stirred at ambient temperature for 3 hours. The reaction mixture was filtered through a pad of silica gel. The pad was rinsed with methylene chloride (2×) and 1:1 ethyl acetate:hexanes (2×). The filtrate was concentrated in vacuo to give the desired compound as a crude residue.

ESI-MS: 307.2 (MH$^+$)

Example 1

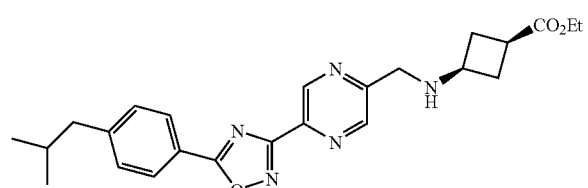

1A. 3-({5-[5-(4-Isobutyl-phenyl)-[1,2,4]oxadiazol-3-yl]-pyrazin-2-ylmethyl}-amino)-cyclobutanecarboxylic acid ethyl ester A solution of 5-[5-(4-isobutylphenyl)-1,2,4-oxadiazol-3-yl]pyrazine-2-carbaldehyde (0.100 g, 0.32 mmol), cis-3-amino-cyclobutanecarboxylic acid ethyl ester (0.056 g, 0.388 mmol), sodium triacetoxyborohydride (0.082 g, 0.388 mmol) and dichloroethane (5.0 mL) was stirred at room temperature for 12 hours. The reaction mixture was quenched with 1N NaOH (10 mL) and the organic layer was isolated, washed with H$_2$O (2×10 mL) and brine (10 mL), dried (Na$_2$SO$_4$), filtered and concentrated in vacuo to yield the title compound as a crude solid.

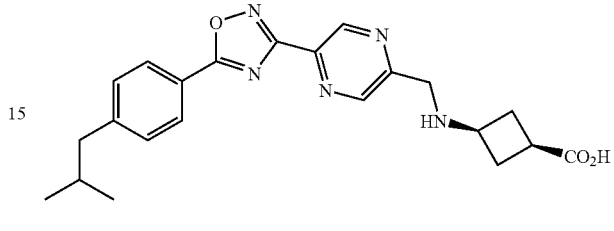

1B. 3-({5-[5-(4-Isobutyl-phenyl)-[1,2,4]oxadiazol-3-yl]-pyrazin-2-ylmethyl}-amino)-cis-cyclobutanecarboxylic acid A solution of 3-({5-[5-(4-isobutyl-phenyl)-[1,2,4]oxadiazol-3-yl]-pyrazin-2-ylmethyl}-amino)-cyclobutanecarboxylic acid ethyl ester, 2.0 N NaOH (1.0 mL) and ethanol (3.0 mL) was heated in a sealed vial in a microwave to 150° C. for 10 minutes. The reaction mixture was cooled to room temperature and concentrated in vacuo to afford the title compound (0.047 g, 36% yield over 2 steps) as a white solid.

ESI-MS: 408.5 (MH$^+$); HPLC R$_f$: 2.2 minutes. (HPLC method 3); HPLC purity: 95%.

Example 2

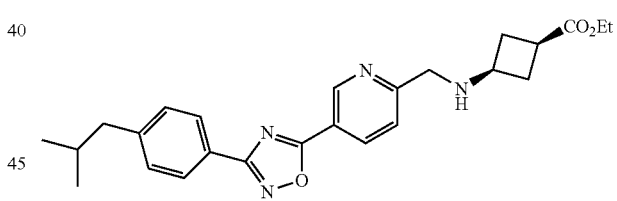

2A. 3-({5-[3-(4-Isobutyl-phenyl)-[1,2,4]oxadiazole-5-yl]-pyridin-2-ylmethyl}-amino)-cis-cyclobutanecarboxylic acid ethyl ester A solution of 5-[5-(4-isobutyl-phenyl)-[1,2,4]oxadiazol-3-yl]-pyridine-2-carbaldehyde (0.059 g, 0.192 mmol), cis-3-amino-cyclobutanecarboxylic acid ethyl ester (0.034 g, 0.192 mmol) and acetic acid/THF (10%, 3.2 mL) was stirred at room temperature for 1 hour. Sodium triacetoxyborohydride (0.081 g, 0.384 mmol) was added to the reaction mixture, stirred at room temperature for 12 hours, quenched with methanol and concentrated in vacuo. The resulting residue was taken up in dichloromethane, washed with water, saturated NaHCO$_3$ and brine, dried (Na$_2$SO$_4$), filtered and concentrated in vacuo to provide the title compound (0.075 g, 90% yield) as a solid.

$^1$H NMR (400 MHz, CDCl$_3$) δ 0.91 (d, 6H), 1.29 (t, 3H), 1.91 (m, 1H), 2.12 (m, 2H), 2.52 (m, 2H), 2.53 (d, 2 h), 2.76

(m, 1H), 3.40 (m, 1H), 4.04 (s, 2H), 4.11 (q, 2H), 7.28 (d, 2H), 7.57 (d, 1H), 8.05 (d, 2H), 8.44 (d, 2H), 9.35 (s, 1H); ESI-MS: 435 (MH$^+$).

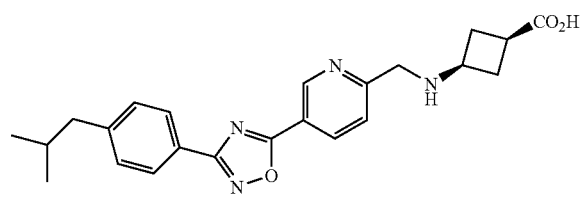

2B. 3-({5-[3-(4-Isobutyl-phenyl)-[1,2,4]oxadiazole-5-yl]-pyridin-2-ylmethyl}-amino)-cis-cyclobutanecarboxylic acid, hydrochloride salt A solution of 3-({5-[5-(4-Isobutyl-phenyl)-[1,2,4]oxadiazole-3-yl]-pyridin-2-ylmethyl}-amino)-cis-cyclobutanecarboxylic acid ethyl ester (0.075 g, 0.172 mmol), 1.0 N NaOH (0.864 mL) and ethanol (0.216 mL) was heated in a sealed vial in a microwave to 100° C. for 5 minutes. The reaction mixture was cooled to room temperature, neutralized to pH of 7.0 with 1.0 N HCl and extracted with ethyl acetate. HCl (2.0 M in diethyl ether, 0.10 mL) was added to the combined organic extracts and the mixture was concentrated in vacuo to afford the title compound (0.046 g, 66% yield) as a solid.

$^1$H NMR (400 MHz, DMSO-d$_4$) δ0.85 (d, 6H), 1.93 (m, 1H), 2.46 (m, 4H), 2.49 (d, 2H), 3.33 (m, 1H), 4.34 (s, 2H), 7.37 (d, 2H), 7.81 (d, 1 h), 8.00 (d, 2H), 8.62 (d, 2H), 9.33 (s, 1H), 9.74 (br.s, 1H); ESI-MS: 407 (MH$^+$).

Example 3

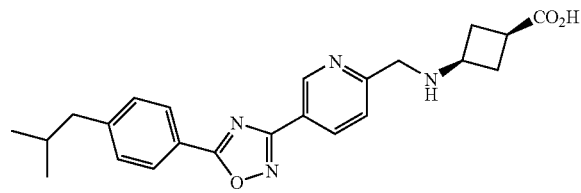

3A. 3-({5-[5-(4-Isobutyl-phenyl)-[1,2,4]oxadiazol-3-yl]-pyridin-2-ylmethyl}-amino)-cis-cyclobutanecarboxylic acid The title compound was prepared from 5-[5-(4-isobutylphenyl)-1,2,4-oxadiazol-3-yl]pyridine-2-carbaldehyde by procedures analogous to those described in Examples (1A-1B) for the preparation of 3-({5-[5-(4-isobutyl-phenyl)-[1,2,4]oxadiazol-3-yl]-pyrazin-2-ylmethyl}-amino)-cyclobutanecarboxylic acid.

ESI-MS: 407.3 (MH$^+$); HPLC R$_f$: 2.3 min. (HPLC method 1); HPLC purity: 94%.

Example 4

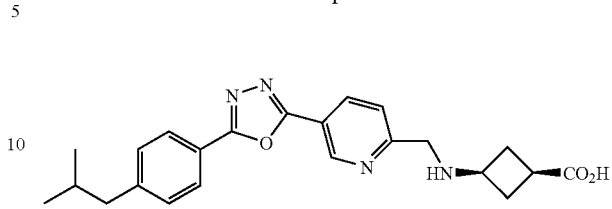

4A. 3-({5-[5-(4-Isobutyl-phenyl)-[1,3,4]oxadiazol-2-yl]-pyridin-2-ylmethyl}-amino)-cis-cyclobutanecarboxylic acid The title compound was prepared from 2-chloro-5-[5-(4-isobutylphenyl)-1,3,4-oxadiazol-2-yl]pyridine by procedures analogous to those described in Preparations (5C-5D) and Examples (1A-1B) for the preparation of 5-[5-(4-isobutylphenyl)-1,2,4-oxadiazol-3-yl]pyridine-2-carbaldehyde and 3-({5-[5-(4-isobutyl-phenyl)-[1,2,4]oxadiazol-3-yl]-pyrazin-2-ylmethyl}-amino)-cyclobutanecarboxylic acid, respectively.

ESI-MS: 407.3 (MH$^+$); HPLC R$_f$: 2.1 minutes (HPLC method 1); HPLC purity: 92%.

Example 5

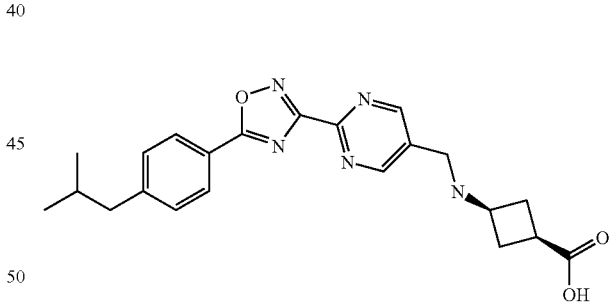

5A. 3-({2-[5-(4-Isobutyl-phenyl)-[1,2,4]oxadiazol-3-yl]-pyrimidin-5-ylmethyl}-amino)-cis-cyclobutanecarboxylic acid The title compound was prepared from 2-[5-(4-isobutyl-phenyl)-[1,2,4]oxadiazol-3-yl]-pyrimidine-5-carbaldehyde by procedures analogous to those described in Examples (1A-1B) for the preparation of 3-({5-[5-(4-isobutyl-phenyl)-[1,2,4]oxadiazol-3-yl]-pyrazin-2-ylmethyl}-amino)-cyclobutanecarboxylic acid.

ESI-MS: 408.3 (MH+); HPLC R$_f$: 2.1 minutes (HPLC method 1); HPLC purity: 100%.

Example 6

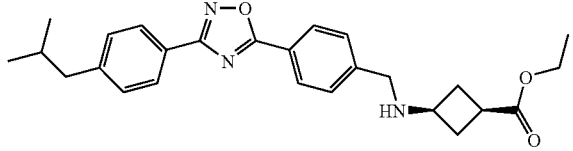

6A: Ethyl cis-3-({4-[3-(4-isobutylphenyl)-1,2,4-oxa-diazol-5-yl]benzyl}amino)cyclobutanecarboxylate cis-3-Amino-cyclobutanecarboxylic acid ethyl ester hydrochloride (0.193 g, 1.35 mmol) was added to a solution of 4-[3-(4-isobutylphenyl)-1,2,4-oxadiazol-5-yl]benzaldehyde (0.333 g, 1.08 mmol), acetic acid (2 mL) and THF (18 mL) and stirred for 30 minutes. Sodium triacetoxyborohydride (0.500 g, 2.36 mmol) was added to the reaction mixture, stirred at room temperature for 16 hours, and concentrated in vacuo to give a white solid. The solid was triturated with water, filtered and dried to give the title compound (0.260 g, 55% yield) as a white solid.

ESI-MS: 434 (MH+).

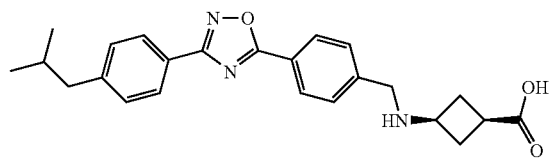

6B: cis-3-({4-[3-(4-Isobutylphenyl)-1,2,4-oxadiazol-5-yl]benzyl}amino)cyclobutanecarboxylic acid hydrochloride 1N NaOH (3.00 g, 3.00 mmol) was added to a solution of ethyl cis-3-({4-[3-(4-isobutylphenyl)-1,2,4-oxadiazol-5-yl]benzyl}amino)cyclobutanecarboxylate (0.260 g, 0.600 mmol) and ethanol (2 mL) and heated to 100° C. in a microwave for 5 minutes. The reaction mixture was adjusted to pH of 7 with 1N HCl causing a white precipitate to form. The reaction mixture was filtered and the solid was slurried in ethyl acetate and treated with 1 N HCl in ether. The slurry was filtered and washed with petroleum ether to give the title compound (0.100 g, 41% yield) as a white solid.

$^1$H NMR (400 MHz, CDCl$_3$) δ 0.87 (d, 6H), 1.87 (m, 1H), 2.35 (m, 2H), 2.53 (d, 2H), 2.88 (m, 1H), 3.63 (m, 1H), 4.15 (s, 1H), 7.38 (d, 2H), 7.78 (d, 2H), 7.99 (d, 2H), 8.23 (d, 2H).

Example 7

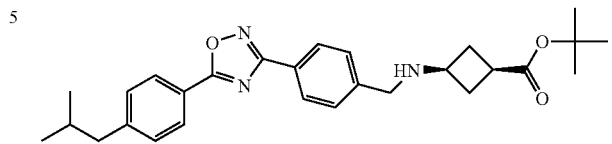

7A. 3-{4-[5(4-Isobutyl-phenyl)-[1,2,4]oxadiazole-3-yl]-benzylamino}-cis-cyclobutanecarboxylic acid tert-butyl ester A solution of 3-cis-amino-cylcobutanecarboxylic acid tert-butyl ester (3.78 g, 19.6 mmol), triethylamine (4.0 mL, 29.4 mmol) and THF (100 mL) was added to a solution of 4-[5-(4-isobutyl-phenyl)-[1,2,4]oxadiazol-3-yl]-benzaldehyde (6.0 g, 19.6 mmol) in acetic acid/THF (1:10, 100 mL) and stirred at room temperature for 1 hour. Sodium triacetoxyborohydride (8.06 g, 39.2 mmol) was added to the reaction mixture, stirred at room temperature for 12 hours, treated with methanol (50.0 mL) and concentrated in vacuo. The resulting residue was taken up in dichloromethane, washed sequentially with brine, saturated NaHCO$_3$ and brine, dried (Na$_2$SO$_4$), filtered and concentrated in vacuo. Purification by flash chromatography (silica, 1:9-1:1 EtOAc:hexanes) provided the title compound (4.0 g, 44% yield) as a solid.

$^1$H NMR (400 MHz, acetone-D$_6$) δ 0.92 (d, 6H), 1.39 (s, 9H), 1.88 (m, 1H), 1.91 (m, 2H), 2.36 (m, 2H), 2.60 (m, 1H), 2.61 (d, 2H), 3.17 (m, 1H), 3.79 (s, 2H), 7.46 (d, 2H), 7.55 (d, 2H), 8.10 (d, 2H), 8.14 (d, 2H); ESI-MS: 461 (MH+).

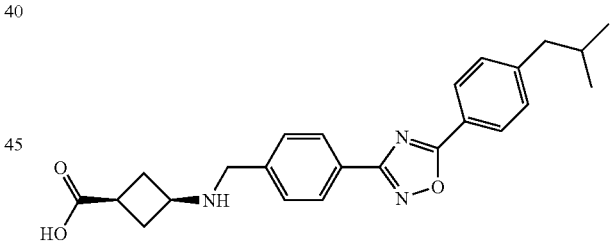

7B. 3-{4-[5-(4-Isobutyl-phenyl)-[1,2,4]oxadiazole-3-yl]-benzylamino}-cis-cyclobutanecarboxylic acid, hydrochloride salt HCl (4.0 M in dioxane, 21.6 mL) and water (3.6 mL) was added to a solution of 3-{4-[5-(4-isobutyl-phenyl)-[1,2,4]oxadiazole-3-yl]-benzylamino}-cis-cyclobutanecarboxylic acid tert-butyl ester (4.0 g, 8.67 mmol) in dioxane (20.0 mL) and stirred at room temperature for 1 hour. Diethyl ether (50.0 mL) was added to the reaction mixture and the resulting slurry was stirred for 2 hours and filtered to yield the title compound (2.8 g, 79% yield) as a solid.

$^1$H NMR (400 MHz, CD$_3$OD) δ 0.92 (d, 6H), 1.93 (m, 1H), 2.42 (m, 2H), 2.62 (m, 2H), 2.62 (d, 2H), 3.00 (m, 1H), 3.79

(m, 1H), 4.21 (s, 2H), 7.40 (d, 2H), 7.66 (d, 2H), 8.11 (d, 2H), 8.22 (d, 2H); ESI-MS: 405 (MH+).

Example 8

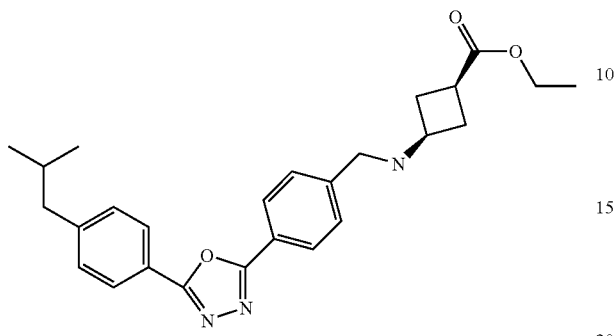

8A: Ethyl cis-3-({4-[5-(4-isobutylphenyl)-1,3,4-oxadiazol-2-yl]benzyl}amino)cyclobutanecarboxylate A mixture of cis-3-amino-cyclobutanecarboxylic acid ethyl ester hydrochloride (0.181 g, 1.01 mmol), triethylamine (0.10 mL, 0.72 mmol) and dichloromethane (8 mL) was stirred at room temperature for 30 minutes. 4-[5-(4-isobutylphenyl)-1,3,4-oxadiazol-2-yl]benzaldehyde (0.181 mg, 1.04 mmol) was added to the reaction mixture and stirred for 2 hours. Sodium triacetoxyborohydride (0.213 g, 1.01 mmol) was added to the reaction mixture and stirred for 16 hours. Additional cis-3-amino-cyclobutanecarboxylic acid ethyl ester hydrochloride (0.100 mg, 0.773 mmol) and sodium triacetoxyborohydride (0.213 g, 1.01 mmol) was added to the reaction mixture and stirred for 72 hours. The reaction mixture was concentrated in vacuo and the resulting residue was triturated with water, filtered and dried to provide the title compound (0.303 g, 88% yield) as a white solid.

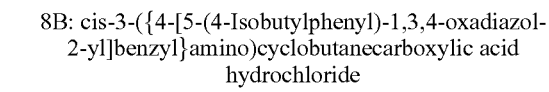

8B: cis-3-({4-[5-(4-Isobutylphenyl)-1,3,4-oxadiazol-2-yl]benzyl}amino)cyclobutanecarboxylic acid hydrochloride A solution of ethyl cis-3-({4-[5-(4-isobutylphenyl)-1,3,4-oxadiazol-2-yl]benzyl}amino)cyclobutane carboxylate (0.300 g, 0.692 mmol), 1N NaOH (6.0 mL), and methanol (5 mL) was heated in a microwave oven at 100° C. for 3 minutes. The reaction mixture was cooled to room temperature and pH was adjusted to 7 with 1N HCl, causing a white solid to precipitate. The reaction mixture was filtered and the solid was washed with water, then treated with 1N HC in ether to give the title compound (0.170 g, 61% yield).

1H NMR (400 MHz, CD3OD) δ 0.91 (d, 6H), 1.90 (m, 1H), 2.41 (m, 2H), 2.61 (m, 2H), 3.06 (m, 1H), 3.28 (s, 2H), 3.83 (m, 1H), 4.87 (s, 2H), 7.39 (d, 2H), 7.71 (d, 2H), 8.05 (d, 2H), 8.23 (d, 2H).

Example 9

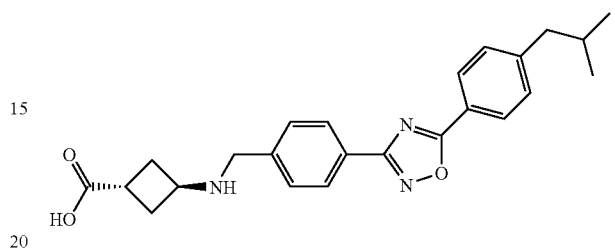

9A. 3-{4-[5-(4-Isobutyl-phenyl)-[1,2,4]oxadiazole-3-yl]-benzylamino}-trans-cyclobutanecarboxylic acid, hydrochloride salt The title compound was prepared from 4-[5-(4-isobutylphenyl)-[1,2,4]oxadiazol-3-yl]-benzaldehyde and 3-trans-amino-cylcobutanecarboxylic acid ethyl ester by procedures analogous to those described in Examples (1A-1B) for the preparation of 3-({5-[5-(4-isobutyl-phenyl)-[1,2,4]oxadiazol-3-yl]-pyrazin-2-ylmethyl}-amino)-cyclobutanecarboxylic acid.

ESI-MS: 406.3 (MH+); HPLC Rf: 2.2 minutes (HPLC method 1); HPLC purity: 100%.

Example 10

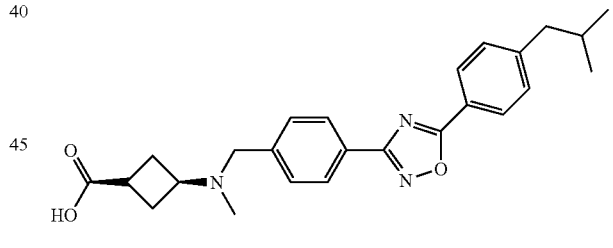

10A. 3-{methyl[4-(5-(4-Isobutyl-phenyl)-[1,2,4]oxadiazole-3-yl)-benzyl]amino}-cis-cyclobutanecarboxylic acid, hydrochloride salt A solution of 3-{4-[5(4-isobutyl-phenyl)-[1,2,4]oxadiazole-3-yl]-benzylamino}-cis-cyclobutanecarboxylic acid (0.100 g, 0.23 mmol), formaldehyde (37% wt. in water, 0.10 mL, 0.57 mmol) and acetic acid (10% in MeOH, 1.32 mL) was stirred at room temperature for 30 minutes. Sodium triacetoxyborohydride (0.047 g, 0.23 mmol) was added to the reaction mixture, stirred at room temperature for 12 hours, and concentrated in vacuo to remove the MeOH. The resulting residue was extracted with dichloromethane and the combined organic layers were washed with saturated NaHCO3, concentrated in vacuo and treated with HCl (2.0 M in diethyl ether, 0.10 mL). The slurry was filtered to afford the title compound (0.053 g, 55% yield).

$^1$H NMR (400 MHz, CD$_3$OD) δ 0.92 (d, 6H), 1.92 (m, 2H), 2.42 (m, 2H), 2.62 (m, 2H), 2.62 (d, 2H), 2.69 (s, 3H), 2.94 (m, 1H), 3.81 (m, 1H), 4.18 (s, 2H), 7.41 (d, 2H), 7.70 (d, 2H), 8.12 (d, 2H), 8.26 (d, 2H); ESI-MS: 420 (MH$^+$).

Example 11

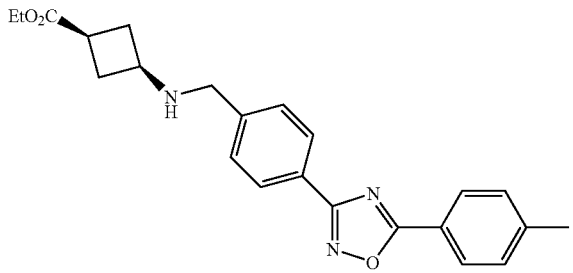

11A. 3-[4-(5-p-Tolyl-[1,2,4]oxadiazol-3-yl)-benzylamino]-cis-cyclobutanecarboxylic acid ethyl ester A mixture of cis-3-amino-cyclobutanecarboxylic acid ethyl ester hydrochloride (50.7 mg, 0.282 mmol), triethylamine (0.058 mL, 0.423 mmol) and THF (2.5 mL) was stirred at room temperature for 30 minutes. 4-[5-(4-Methylphenyl)-1,2,4-oxadiazol-3-yl]benzaldehyde (74.5 mg, 0.282 mmol) and AcOH (0.50 mL) were added to the reaction mixture and stirred for 30 minutes. Sodium cyanoborohydride (35.4 g, 0.563 mmol) was added to the reaction mixture, stirred for 18 hours, quenched with sat. NaHCO$_3$ and extracted with ethyl acetate. The organic phase was concentrated in vacuo. Purification by flash chromatography (silica, 2:8 EtOAc:hexanes) provided the title compound (43.6 g, 39.8% yield) as a solid.

ESI-MS: 392.2 (MH$^+$); HPLC R$_f$: 2.19 minutes (HPLC method 1); HPLC purity: >90%.

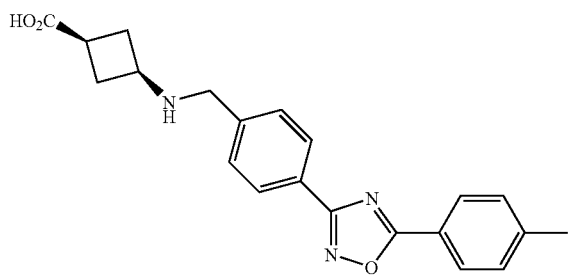

11B. 3-[4-(5-p-Tolyl-[1,2,4]oxadiazol-3-yl)-benzylamino]-cis-cyclobutanecarboxylic acid hydrochloride Water (0.50 mL) and 1N NaOH (0.11 mL) was added to a solution of 3-[4-(5-p-tolyl-[1,2,4]oxadiazol-3-yl)-benzylamino]-cyclobutanecarboxylic acid ethyl ester (43.8 mg, 0.112 mmol) and THF (0.50 mL) and stirred at room temperature for 18 hours. The reaction mixture was diluted with methanol and loaded onto a column (solid phase anionic exchange sorbent). The column was washed with water and THF and eluted with acetic acid (10% in THF). The eluent was concentrated in vacuo and the resulting residue was taken up in CH$_2$Cl$_2$ (3 mL) and HCl (sat. in ether, 2 mL) and stirred for 1 hour. The slurry was concentrated in vacuo to provide the title compound (22 mg, 49% yield) as a solid.

ESI-MS: 364.2 (MH$^+$); HPLC R$_f$: 2.0 minutes (HPLC method 1).

Examples 12-27

Examples 12-27 listed in the following table were prepared using procedures analogous to those described in Examples (11A-11B) for the preparation of 3-[4-(5-p-tolyl-[1,2,4]oxadiazol-3-yl)-benzylamino]-cis-cyclobutanecarboxylic acid.

| Example | Compound Name | MH+ | HPLC Rf (min) | HPLC method |
|---|---|---|---|---|
| 12 | 3-{4-[5-(4-Ethyl-phenyl)-[1,2,4]oxadiazol-3-yl]-benzylamino}-cis-cyclobutanecarboxylic acid | 378.2 | 2.1 | 1 |
| 13 | 3-{4-[5-(4-Propyl-phenyl)-[1,2,4]oxadiazol-3-yl]-benzylamino}-cis-cyclobutanecarboxylic acid | 392.2 | 2.4 | 1 |
| 14 | 3-{4-[5-(3-Ethyl-phenyl)-[1,2,4]oxadiazol-3-yl]-benzylamino}-cis-cyclobutanecarboxylic acid | 378.2 | 2.1 | 1 |
| 15 | 3-[4-(5-o-Tolyl-[1,2,4]oxadiazol-3-yl)-benzylamino]-cis-cyclobutanecarboxylic acid | 346.2 | 2.0 | 1 |
| 16 | 3-{4-[5-(2-Ethyl-phenyl)-[1,2,4]oxadiazol-3-yl]-benzylamino}-cis-cyclobutanecarboxylic acid | 378.2 | 2.0 | 1 |
| 17 | 3-{3-[5-(2-Ethyl-phenyl)-[1,2,4]oxadiazol-3-yl]-benzylamino}-cis-cyclobutanecarboxylic acid | 378.2 | 2.1 | 1 |
| 18 | 3-[3-(5-o-Tolyl-[1,2,4]oxadiazol-3-yl)-benzylamino]-cis-cyclobutanecarboxylic acid | 362.2 | 1.8 | 1 |
| 19 | 3-{3-[5-(3-Ethyl-phenyl)-[1,2,4]oxadiazol-3-yl]-benzylamino}-cis-cyclobutanecarboxylic acid | 378.2 | 2.0 | 1 |
| 20 | 3-{3-[5-(4-Isobutyl-phenyl)-[1,2,4]oxadiazol-3-yl]-benzylamino}-cis-cyclobutanecarboxylic acid | 406.2 | 2.3 | 1 |
| 21 | 3-{3-[5-(4-Propyl-phenyl)-[1,2,4]oxadiazol-3-yl]-benzylamino}-cis-cyclobutanecarboxylic acid | 392.2 | 2.3 | 1 |
| 22 | 3-{3-[5-(4-Ethyl-phenyl)-[1,2,4]oxadiazol-3-yl]-benzylamino}-cis-cyclobutanecarboxylic acid | 378.2 | 2.1 | 1 |
| 23 | 3-[3-(5-p-Tolyl-[1,2,4]oxadiazol-3-yl)-benzylamino]-cis-cyclobutanecarboxylic acid | 364.2 | 2.0 | 1 |
| 24 | 3-[2-(5-p-Tolyl-[1,2,4]oxadiazol-3-yl)-benzylamino]-cis-cyclobutanecarboxylic acid | 364.2 | 2.0 | 1 |
| 25 | 3-{2-[5-(4-Propyl-phenyl)-[1,2,4]oxadiazol-3-yl]-benzylamino}-cis-cyclobutanecarboxylic acid | 392.2 | 2.3 | 1 |

| | | | HPLC | |
|---|---|---|---|---|
| Example | Compound Name | MH+ | Rf (min) | method |
| 26 | 3-[2-(5-m-Tolyl-[1,2,4]oxadiazol-3-yl)-benzylamino]-cis-cyclobutanecarboxylic acid | 364.2 | 1.9 | 1 |
| 27 | 3-[2-(5-o-Tolyl-[1,2,4]oxadiazol-3-yl)-benzylamino]-cis-cyclobutanecarboxylic acid | 364.2 | 1.9 | 1 |

Example 28

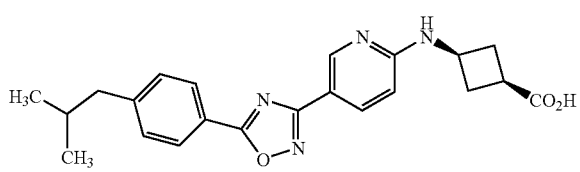

28A: 3-{5-[5-(4-Isobutyl-phenyl)-[1,2,4]oxadiazol-3-yl]-pyridin-2-ylamino}-cyclobutanecarboxylic acid hydrochloride A solution of 2-chloro-5-[5-(4-isobutylphenyl)-1,2,4-oxadiazol-3-yl]pyridine (50 mg, 0.16 mmol), cis-3-amino-cylcobutanecarboxylic acid ethyl ester, hydrochloride (57.1 mg, 0.319 mmol), potassium phosphate dibasic (58.3 mg, 0.335 mmol) and DMSO (5 mL) was stirred in a sealed tube in the microwave at 200° C. for 10 minutes. The reaction mixture was cooled to room temperature and concentrated in vacuo. The resulting residue was dissolved in EtOH (3 mL). NaOH (19 mg, 0.478 mmol) and water (2 mL) were added to the reaction mixture and stirred in a sealed tube in the microwave at 180° C. for 10 minutes. The reaction mixture was cooled to room temperature, acidified with 1N HCl (5 mL), filtered and dried to provide the title compound (59 mg, 86% yield) as a solid.

ESI-MS: 393.2 (MH+): HPLC $R_f$: 2.7 minutes. (HPLC method 1); HPLC purity: 100%.

Example 29

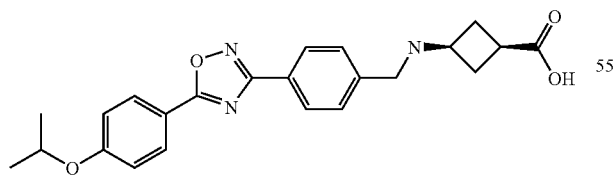

29: 3-{4-[5-(4-Isopropoxy-phenyl)-[1,2,4]oxadiazol-3-yl]-benzylamino}-cis-cyclobutanecarboxylic acid hydrochloride The title compound was prepared from 4-[5-(4-isopropoxy-phenyl)-[1,2,4]oxadiazol-3-yl]-benzaldehyde by procedures analogous to those described in Examples (1A-1B) for the preparation of 3-({5-[5-(4-isobutyl-phenyl)-[1,2,4]oxadiazol-3-yl]-pyrazin-2-ylmethyl}-amino)-cis-cyclobutanecarboxylic acid.

$^1$H NMR (400 MHz, DMSO-D$_6$) δ 1.28 (d, 6H), 2.35 (m, 4H), 2.85 (m, 1H), 3.38 (m, 1H), 3.62 (d, 1H), 4.12 (s, 2H), 4.78 (m, 1H), 7.14 (d, 2H), 7.68 (d, 2H), 8.11 (m, 4H); ESI-MS: 408.2 (MH+); HPLC $R_f$: 6.5 min. (HPLC method 4).

Examples 30-32

Examples 30-32 listed in the following table were prepared using procedures analogous to those described in Example 29 for the preparation of 3-{4-[5-(4-isopropoxy-phenyl)-[1,2,4]oxadiazol-3-yl]-benzylamino}-cyclobutanecarboxylic acid hydrochloride.

| | | | HPLC | |
|---|---|---|---|---|
| Example | Compound Name | MH+ | Rf (min) | method |
| 30 | 3-{4-[5-(4-Trifluoromethoxy-phenyl)-[1,2,4]oxadiazol-3-yl]-benzylamino}-cis-cyclobutanecarboxylic acid | 433.1 | 7.25 | 4 |
| 31 | 3-{4-[5-(6-Trifluoromethyl-pyridin-3-yl)-[1,2,4]oxadiazol-3-yl]-benzylamino}-cis-cyclobutanecarboxylic acid | 419.2 | 6.03 | 4 |
| 32 | 3-(4-{5-[6-(2,2,2-Trifluoro-ethoxy)-pyridin-3-yl]-[1,2,4]oxadiazol-3-yl}-benzylamino)-cis-cyclobutanecarboxylic acid | 449.2 | 6.82 | 4 |

Example 33

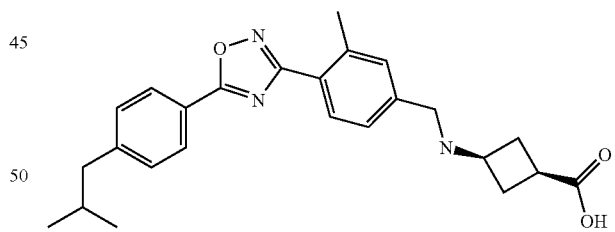

33A: 3-[({4-[5-(4-Isobutyl-phenyl)-[1,2,4]oxadiazol-3-yl]-3-methyl-phenyl}methyl)-amino]-cis-cyclobutanecarboxylic acid The title compound was prepared from 4-[5-(4-isobutyl-phenyl)-[1,2,4]oxadiazol-3-yl]-3-methyl-benzoic acid methyl ester by procedures analogous to those described in Preparations (6F-6G) and Examples (1A-1B) for the preparation of 5-[5-(4-isobutylphenyl)-1,2,4-oxadiazol-3-yl]pyrazine-2-carbaldehyde and 3-({5-[5-(4-isobutyl-phenyl)-[1,2,4]oxadiazol-3-yl]-pyrazin-2-ylmethyl}-amino)-cis-cyclobutanecarboxylic acid, respectively.

Example 34

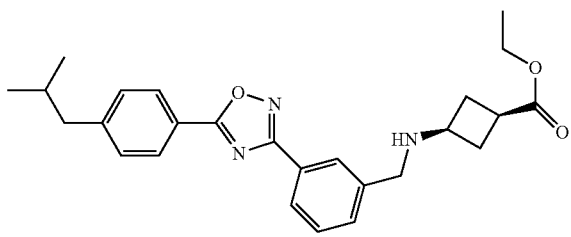

34A. 3-{3-[5(4-Isobutyl-phenyl)-[1,2,4]oxadiazole-3-yl]-benzylamino}-cis-cyclobutanecarboxylic acid ethyl ester A solution of cis-3-amino-cyclobutanecarboxylic acid ethyl ester hydrochloride (34 mg, 0.189 mmol), triethyl amine (39.5 uL, 0.284 mmol) and THF (1.7 mL) was stirred at ambient temperature for 30 minutes. Acetic acid (300 uL) and 3-[5-(4-isobutylphenyl)-1,2,4-oxadiazol-3-yl]benzaldehyde (58 mg, 0.189 mmol) were added to the reaction mixture and stirred for 30 minutes. Sodium triacetoxy borohydride (80 mg, 0.379 mmol) was added to the mixture and stirred for 18 hours. The reaction was diluted with ethyl acetate, washed with saturated sodium bicarbonate and the organic layer was separated and concentrated in vacuo. Purification by flash chromatography (silica, 1:99 to 1:9 MeOH:chloroform) provided the title compound (68 mg, 83% yield) as a solid.

ESI-MS: 434.3 (MH⁺).

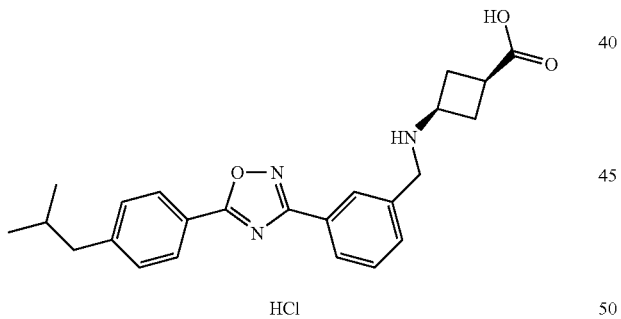

34B. 3-{3-[5-(4-Isobutyl-phenyl)-[1,2,4]oxadiazole-3-yl]-benzylamino}-cis-cyclobutanecarboxylic acid, hydrochloride Aqueous sodium hydroxide (1 M, 157 uL, 0.157 mmol) was added to a solution of 3-{3-[5(4-isobutyl-phenyl)-[1,2,4]oxadiazole-3-yl]-benzylamino}-cis-cyclobutanecarboxylic acid ethyl ester (68 mg, 0.157 mmol) and THF/water (1:1, 1 mL). The reaction mixture was stirred at ambient temperature for 18 hours, diluted with methanol and loaded directly onto a MAX column (solid phase anionic exchange sorbent). The column was rinsed with water (2×) and THF (2×) and then eluted with acetic acid (10% in THF). The eluent was concentrated in vacuo and the resulting residue was slurried in methylene chloride. A saturated ether/HCl solution was added to the slurry and the reaction mixture was concentrated in vacuo to give the title compound (30.7 mg, 48% yield) as a solid.

ESI-MS: 406.2 (MH⁺).

The following table illustrates compounds (Examples 35-42) that were not made but may be prepared by methods analogous to those described above and are expected to have the following data.

| Example | Molecular Structure | Compound name | MH+ |
|---|---|---|---|
| 35 | 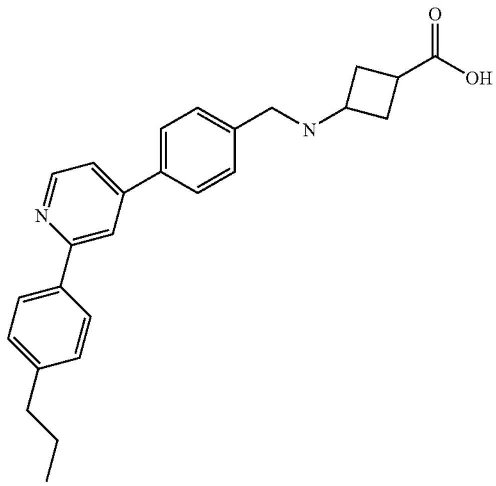 | 3-{4-[2-(4-Propyl-phenyl)-pyridin-4-yl]-benzylamino}-cyclobutanecarboxylic acid | 401 |
| 36 | 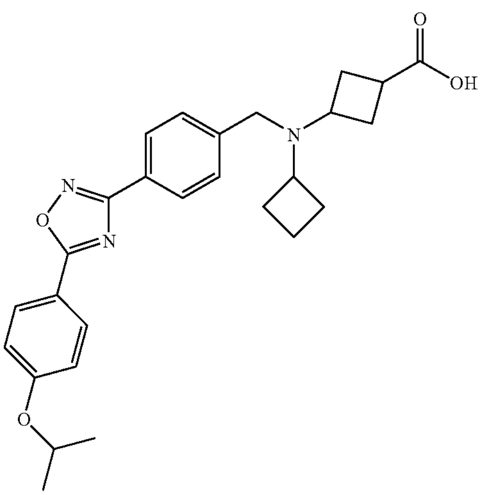 | 3-(Cyclobutyl-{4-[5-(4-isopropoxy-phenyl)-[1,2,4]oxadiazol-3-yl]-benzyl}-amino)-cyclobutanecarboxylic acid | 462 |
| 37 | 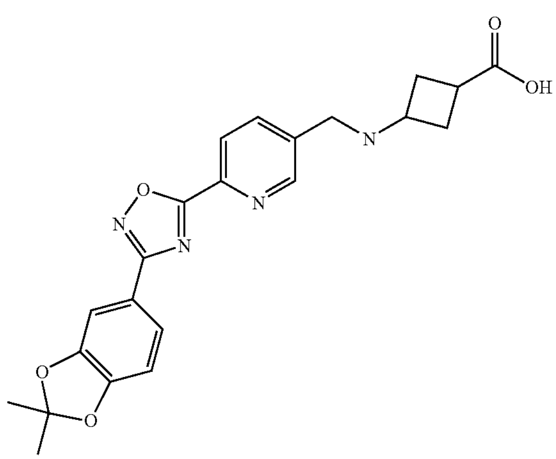 | 3-({6-[3-(2,2-Dimethyl-benzo[1,3]dioxol-5-yl)-[1,2,4]oxadiazol-5-yl]-pyridin-3-ylmethyl}-amino)-cyclobutanecarboxylic acid | 423 |

-continued

| Example | Molecular Structure | Compound name | MH+ |
|---|---|---|---|
| 38 | 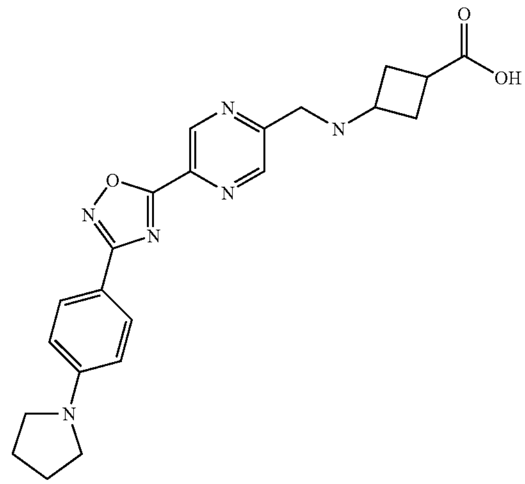 | 3-({5-[3-(4-Pyrrolidin-1-yl-phenyl)-[1,2,4]oxadiazol-5-yl]-pyrazin-2-ylmethyl}-amino)-cyclobutanecarboxylic acid | 421 |
| 39 | 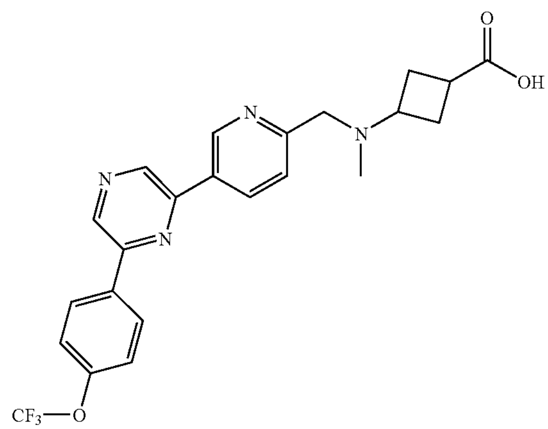 | 3-(Methyl-{5-[6-(4-trifluoromethoxy-phenyl)-pyrazin-2-yl]-pyridin-2-ylmethyl}-amino)-cyclobutanecarboxylic acid | 405 |
| 40 | 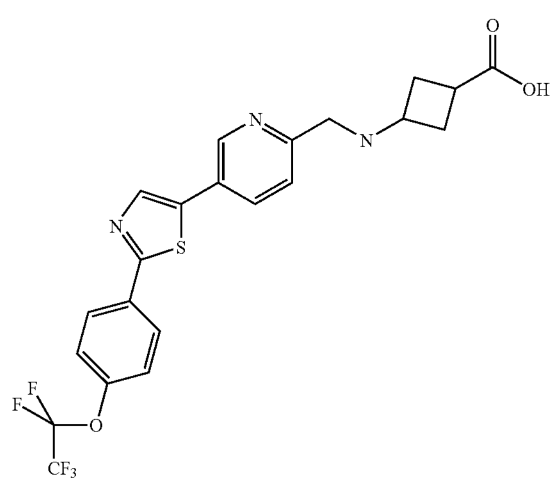 | 3-[(5-{2-[4-(1,1,2,2,2-Pentafluoro-ethoxy)-phenyl]-thiazol-5-yl}-pyridin-2-ylmethyl)-amino]-cyclobutanecarboxylic acid | 446 |

-continued

| Example | Molecular Structure | Compound name | MH+ |
|---|---|---|---|
| 41 | 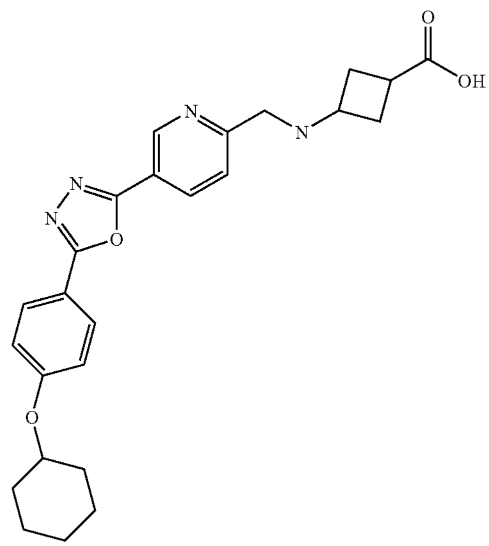 | 3-{4-[-(4-Cyclahexyloxy-phenyl)-[1,3,4]oxadiazol-2-yl]-benzylamino}-cyclobutanecarboxylic acid | 448 |
| 42 | 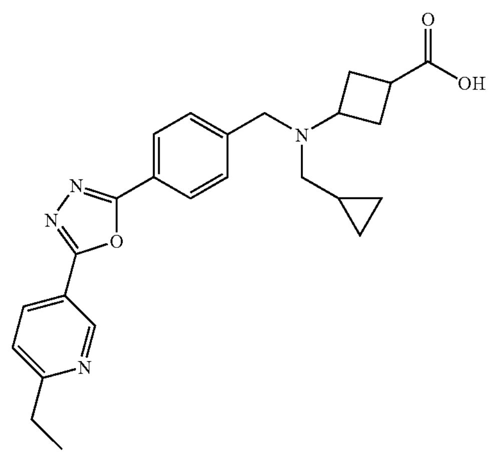 | 3-(Cyclopropylmethyl-{4-[5-(6-ethyl-pyridin-3-yl)-[1,3,4]oxadiazol-2-yl]-benzyl}-amino)-cyclobutanecarboxylic acid | 433 |

The invention claimed is:

1. A compound selected from the group consisting of:
   3-{4-[5-(4-isobutyl-phenyl)-[1,2,4]oxadiazole-3-yl]-benzylamino}-cis-cyclobutanecarboxylic acid; and
   3-{4-[5-(4-isobutyl-phenyl)-[1,2,4]oxadiazole-3-yl]-benzylamino}-trans-cyclobutanecarboxylic acid; or
   pharmaceutically acceptable salts of the aforementioned compounds.

2. The compound according to claim 1 wherein said compound is selected from the group consisting of:
   3-{4-[5-(4-isobutyl-phenyl)-[1,2,4]oxadiazole-3-yl]-benzylamino}-cis-cyclobutanecarboxylic acid hydrochloride; and
   3-{4-[5(4-isobutyl-phenyl)-[1,2,4]oxadiazole-3-yl]benzylamino}-trans-cyclobutanecarboxylic acid hydrochloride.

3. A compound which is 3-{4-[5-(4-isobutyl-phenyl)-[1,2,4]oxadiazole-3-yl]-benzylamino}-cis-cyclobutanecarboxylic acid or a pharmaceutically acceptable salt thereof.

4. A pharmaceutical composition comprising:
   a compound as defined in claim 1, or a pharmaceutically acceptable salt thereof; and
   a pharmaceutically acceptable carrier.

5. The pharmaceutical composition according to claim 4, wherein the compound is 3-{4-[5-(4-isobutyl-phenyl)-[1,2,4]oxadiazole-3-yl]-benzylamino}-cis-cyclobutanecarboxylic acid or a pharmaceutically acceptable salt thereof.

* * * * *